(12) United States Patent
Sun et al.

(10) Patent No.: US 8,119,808 B2
(45) Date of Patent: Feb. 21, 2012

(54) TETRAHYDROQUINOLINE DERIVATIVES AS CANNABINOID RECEPTOR MODULATORS

(75) Inventors: Chongqing Sun, East Windsor, NJ (US); Doree Sitkoff, Dresher, PA (US); William R. Ewing, Yardley, PA (US); Yanting Huang, Pennington, NJ (US); Bruce A. Ellsworth, Princeton, NJ (US); Richard B. Sulsky, West Trenton, NJ (US); Annapurna Pendri, Glastonbury, CT (US); Samuel Gerritz, Guilford, CT (US); Natesan Murugesan, Princeton Junction, NJ (US); Zhengxiang Gu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/984,628

(22) Filed: Jan. 5, 2011

(65) Prior Publication Data

US 2011/0104315 A1    May 5, 2011

Related U.S. Application Data

(60) Division of application No. 12/108,616, filed on Apr. 24, 2008, now Pat. No. 7,884,113, which is a continuation of application No. 10/889,274, filed on Jul. 12, 2004, now abandoned.

(60) Provisional application No. 60/486,774, filed on Jul. 11, 2003.

(51) Int. Cl.
C07D 215/38 (2006.01)
A61K 31/04 (2006.01)

(52) U.S. Cl. .......................... 546/159; 546/153; 514/312
(58) Field of Classification Search .................. 546/153, 546/159; 514/312
See application file for complete search history.

(56) References Cited

U.S. PATENT DOCUMENTS

| | | | |
|---|---|---|---|
| 2,554,737 A | 5/1951 | Haefliger et al. | |
| 4,371,720 A | 2/1983 | Johnson et al. | |
| 5,013,387 A | 5/1991 | Goodwin et al. | |
| 5,081,122 A | 1/1992 | Ward | |
| 5,292,736 A | 3/1994 | Kumar et al. | |
| 5,403,857 A | 4/1995 | Edwards et al. | |
| 5,773,203 A | 6/1998 | Kimura et al. | |
| 5,891,909 A | 4/1999 | Soll et al. | |
| 6,107,252 A | 8/2000 | Andree et al. | |
| 6,387,926 B1 * | 5/2002 | Bhide et al. ............ | 514/311 |
| 6,541,661 B1 | 4/2003 | Delorme et al. | |
| 6,559,144 B2 | 5/2003 | Diefenbach et al. | |
| 6,602,883 B1 * | 8/2003 | Bhide et al. ............ | 514/311 |
| 7,276,608 B2 | 10/2007 | Sher et al. | |
| 2001/0021709 A1 | 9/2001 | Diefenbach et al. | |
| 2003/0232804 A1 | 12/2003 | Pinto et al. | |
| 2004/0002495 A1 | 1/2004 | Sher et al. | |
| 2004/0082798 A1 | 4/2004 | Alonso-Alija et al. | |

FOREIGN PATENT DOCUMENTS

| | | |
|---|---|---|
| EP | 044451 | 9/1991 |
| EP | 0570920 | 11/1993 |
| EP | 1340500 | 9/2003 |
| FR | 2735774 | 12/1996 |
| GB | 2272439 | 5/1984 |
| WO | WO 94/12466 | 6/1994 |
| WO | WO 96/36596 | 11/1996 |
| WO | WO 97/29079 | 8/1997 |
| WO | WO 98/41519 | 9/1998 |
| WO | WO99/01434 | 1/1999 |
| WO | WO 99/02499 | 1/1999 |
| WO | WO 00/13508 | 3/2000 |
| WO | WO 01/79261 | 10/2001 |
| WO | WO 02/30357 | 4/2002 |
| WO | WO 02/070510 | 9/2002 |
| WO | WO 03/007887 | 1/2003 |
| WO | WO 03/020217 | 3/2003 |
| WO | WO 03/027069 | 4/2003 |
| WO | WO 03/027076 | 4/2003 |
| WO | WO 03/027114 | 4/2003 |
| WO | WO 03/035005 | 5/2003 |
| WO | WO 03/051850 | 6/2003 |
| WO | WO 03/051851 | 6/2003 |
| WO | WO 03/103677 | 12/2003 |
| WO | WO 2004/015130 | 2/2004 |

OTHER PUBLICATIONS

Trillou, Int J Obesity, vol. 28, pp. 640-648, 2004.* Tamura, S.Y. et el., "Novel Benzo-Fused Lactam Scaffolds es Factor Xa Inhibitors", Bioorganic & Medicinal Chemistry Letters, vol. 9 No. 17, pp. 2753-2758 (1999).
Huffman et al., Bioorg. Med. Chem., 13, 2005, pp. 89-112.
Bhide et al., Caplus an 1999: 48704.
Trillou, Int J. Obesity, vol. 28, 2004, pp. 640-748.

* cited by examiner

Primary Examiner — D M Seaman
(74) Attorney, Agent, or Firm — Ying Wang

(57) ABSTRACT

The invention provides for compounds of formula I

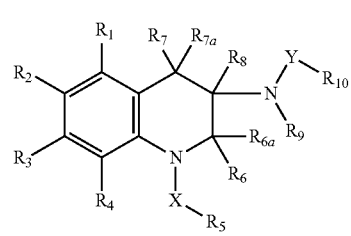

wherein the substituents are as described herein.
Further provided are methods of using such compounds for the treatment of eating disorders, metabolic disorders, obesity, cognitive disorders, neurological disorders, pain disorders, inflammation disorders, in the promotion of smoking cessation and for the treatment of other psychiatric disorders Also provided are pharmaceutical compositions containing such compounds and pharmaceutical combinations of the compounds of the invention with other therapeutic agents.

9 Claims, No Drawings

TETRAHYDROQUINOLINE DERIVATIVES AS CANNABINOID RECEPTOR MODULATORS

CROSS REFERENCE TO RELATED APPLICATIONS

This application is a divisional application of U.S. application Ser. No. 12/108,616 filed Apr. 24, 2008, which is a continuation of U.S. application Ser. No. 10/889,274 filed Jul. 12, 2004, which claims priority to U.S. Provisional Application Ser. No. 60/486,774, filed Jul. 11, 2003, the contents of which are herein incorporated by reference in their entirety.

FIELD OF THE INVENTION

The present invention relates to tetrahydroquinoline containing compounds and compositions, to processes for preparing such compounds and compositions, and to the use of such compounds and compositions in the treatment of eating disorders, metabolic disorders, obesity, cognitive disorders, neurological disorders, pain disorders, inflammation disorders, in the promotion of smoking cessation and for the treatment of other psychiatric disorders.

BACKGROUND OF THE INVENTION

Delta-9-tetrahydrocannabinol or Delta-9 THC, the principle active component of Cannabis sativa (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

Compounds that reportedly bind to the cannabinoid G-protein receptors are disclosed in European Patent Documents Nos. EP 0570920 and EP 0444451; International Publications Nos. WO 9729079, WO 9902499, WO 9841519, WO 9412466, WO 03007887, WO 03027069, WO 03027114, WO 03020217, WO 03027076, WO 03035005, WO 03051850, WO 03051851; U.S. Pat. Nos. 4,371,720, 5,081,122, 5,292,736, and 5,013,387; and French Patent No. FR 2,735,774, each of which is incorporated herein by reference.

SUMMARY OF THE INVENTION

In accordance with illustrative embodiments and demonstrating features of the present invention, compounds are provided which are capable of modulating the function of cannabinoid receptors. Preferably the compounds are cannabinoid-1 receptor (CB-1) modulators, and have the general formula I

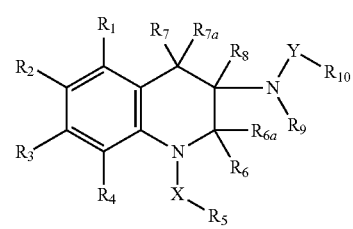

including all pharmaceutically acceptable salts and stereoisomers, wherein $R_1$, $R_2$, $R_3$, $R_4$, $R_5$, $R_6$, $R_{6a}$, $R_7$, $R_{7a}$, $R_8$, $R_9$, $R_{10}$, X and Y are described herein.

DETAILED DESCRIPTION OF THE INVENTION

Thus, in a first embodiment, the present invention provides for a compound of formula I

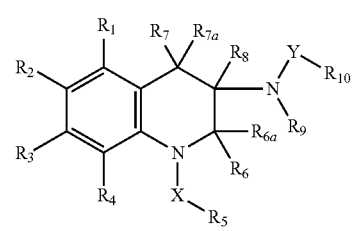

including all pharmaceutically acceptable salts and stereoisomers, wherein:

$R_1$ is selected from the group consisting of hydrogen, alkyl, halo and CN;

$R_2$ is selected from the group consisting of hydrogen, alkyl, alkenyl, alkynyl, cycloalkyl, cycloalkylalkyl, heterocyclyl, heterocycloalkyl, aryl, heteroaryl, arylalkyl, heteroarylalkyl, acyl, halo, $CF_3$, CN, nitro, $OR_{11}$, $NR_{12}R_{12a}$, $COOR_{12}$ and $CONR_{12}R_{12a}$;

$R_3$ is selected from the group consisting of hydrogen, alkyl, halo and CN;

$R_4$ is selected from the group consisting of hydrogen, alkyl, halo and CN;

$R_5$ is selected from the group consisting of alkyl, alkenyl, alkynyl, cycloalkyl, heterocyclyl, aryl, heteroaryl, $COOR_{13}$ and $CONR_{13}R_{13a}$;

$R_6$ and $R_{6a}$ are each independently selected from the group consisting of hydrogen, alkyl and cycloalkyl;

$R_7$ and $R_{7a}$ are each independently selected from the group consisting of hydrogen, alkyl and cycloalkyl;

$R_8$ is selected from the group consisting of hydrogen and alkyl;

$R_9$ is selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

$R_{10}$ is selected from the group consisting of alkyl, alkenyl, alkynyl, cycloalkyl, cycloalkylalkyl, heterocyclyl, heterocycloalkyl, aryl, heteroaryl, arylalkyl and heteroarylalkyl;

$R_{11}$ is selected from the group consisting of hydrogen, alkyl, alkenyl, alkynyl, cycloalkyl, cycloalkylalkyl, heterocyclyl, heterocycloalkyl, aryl, heteroaryl, arylalkyl, heteroarylalkyl, $CHF_2$ and $CF_3$;

$R_{12}$ and $R_{12a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{12}$ and $R_{12a}$ taken together can form cycloalkyl or heterocyclyl;

$R_{13}$ and $R_{13a}$ are each independently selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{13}$ and $R_{13a}$ taken together can form cycloalkyl or heterocyclyl;

X is selected from the group consisting of $(CR_{14}R_{14a})_n$, CO, COO, $S(O)_2$, $SO_2N(R_{12})$ and $CON(R_{12})$;

or $R_5$ and $R_{12}$ taken together can form cycloalkyl or heterocyclyl;

Y is selected from the group consisting of $S(O)_2$, $SO_2N(R_{15})$ and C(O)C(O);

$R_{14}$ and $R_{14a}$ are each independently selected from the group consisting of hydrogen, alkyl;

$R_{15}$ is selected from the group consisting of hydrogen, alkyl, alkenyl, alkynyl, cycloalkyl, cycloalkylalkyl, heterocyclyl, heterocycloalkyl, aryl, heteroaryl, arylalkyl and heteroarylalkyl;

or $R_{10}$ and $R_{15}$ taken together can form cycloalkyl or heterocyclyl;

n is an integer of 0, 1, or 2.

In a preferred embodiment, the present invention provides the compound of claim 1, including all pharmaceutically acceptable salts and stereoisomers, wherein:

$R_2$ is selected from the group consisting of alkyl, alkenyl, alkynyl, cycloalkyl, heterocyclyl, aryl, heteroaryl, arylalkyl, heteroarylalkyl, acyl, halo, CN;

$R_5$ is selected from the group consisting of alkenyl, cycloalkyl, heterocyclyl, aryl, and heteroaryl;

$R_6$ and $R_{6a}$ are each independently selected from the group consisting of hydrogen and alkyl;

$R_7$ and $R_{7a}$ are each independently selected from the group consisting of hydrogen and alkyl;

$R_8$ is hydrogen;

$R_9$ is hydrogen;

$R_{11}$ is selected from the group consisting of alkyl, cycloalkyl, heterocyclyl, aryl, heteroaryl, $CHF_2$ and $CF_3$;

X is $CH_2$;

Y is selected from the group consisting of $S(O)_2$, and $SO_2N(R_{15})$;

$R_{15}$ is selected from the group consisting of hydrogen, alkyl, cycloalkyl, cycloalkylalkyl, aryl, heteroaryl, arylalkyl and heteroarylalkyl;

or $R_{10}$ and $R_{15}$ taken together can form cycloalkyl or heterocyclyl;

n is an integer of 0, or 1.

In a more preferred embodiment, the present invention provides the compound of claim 1, including all pharmaceutically acceptable salts and stereoisomers, wherein:

$R_1$ is hydrogen;

$R_2$ is selected from the group consisting of alkyl, alkenyl, cycloalkyl, heterocyclyl, aryl, heteroaryl, halo and CN;

$R_3$ is hydrogen;

$R_4$ is hydrogen;

$R_5$ is selected from the group consisting of aryl and heteroaryl;

$R_6$ and $R_{6a}$ are each hydrogen;

$R_7$ and $R_{7a}$ are each hydrogen;

$R_{10}$ is selected from the group consisting of alkyl, cycloalkyl, cycloalkylalkyl, heterocyclyl, heterocycloalkyl, aryl, heteroaryl, arylalkyl and heteroarylalkyl;

$R_{15}$ is selected from the group consisting of hydrogen, alkyl;

or $R_{10}$ and $R_{15}$ taken together can form cycloalkyl or heterocyclyl;

n is an integer of 1.

In a second embodiment, the present invention provides a pharmaceutical composition comprising a compound of formula I and a pharmaceutically acceptable carrier or diluent.

In a third embodiment, the present invention provides a pharmaceutical combination comprising a compound of formula I and a therapeutic agent selected from anti-obesity agents; appetite suppressants; anti-diabetic agents; anti-hyperlipidemia agents; hypolipidemic agents; hypocholesterolemic agents; lipid-modulating agents; cholesterol-lowering agents; HDL-raising agents; lipid-lowering agents; anti-hypertensive agents; agents used to treat sleep disorders; agents used to treat substance abuse and addictive disorders; anti-anxiety agents; anti-depressants; anti-psychotic agents; cognition enhancing agents; agents used to treat cognitive disorders; agents used to treat attention deficit-disorders; agents used to treat Alzheimer's disease; agents used to treat Parkinson's disease; anti-inflammatory agents; agents used to treat neurodegeneration; agents used to treat arteriosclerosis; agents used to treat respiratory conditions; agents used to treat gastrointestinal disorders including bowel and motility disorders; cardiac glycosides; and anti-tumor agents.

In a preferred embodiment, the present invention provides a pharmaceutical combination of a compound of formula I and another therapeutic agent wherein the other therapeutic agent may be administered prior to, simultaneously with, or following the administration of the pharmaceutical composition comprising a compound of formula I.

In another preferred embodiment, the present invention provides a pharmaceutical combination of a compound of formula I and an anti-obesity agent wherein the anti-obesity agent is selected from melanocortin receptor (MC4R) agonists; melanin-concentrating hormone receptor (MCHR) antagonists; growth hormone secretagogue receptor (GHSR) antagonists; orexin antagonists; galanin receptor modulators, CCK agonists; GLP-1 agonists and other Pre-proglucagon-derived peptides; NPY1 or NPY5 antagonists; NPY2 and NPY4 modulators; corticotropin releasing factor agonists; histamine receptor-3 (H3) modulators; aP2 inhibitors; PPAR gamma modulators; PPAR delta modulators; acetyl-CoA carboxylase (ACC) inhibitors, adiponectin receptor modulators, 11 β-HSD inhibitors, beta 3 adrenergic agonists, including AJ9677, L750355 and CP331648 or other known beta 3 agonists; thyroid receptor beta modulator; lipase inhibitors, including orlistat and ATL-962; serotonin receptor agonists, including BVT-933; monoamine reuptake inhibitors or releasing agents, including fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol; anorectic agents, including topiramate; ciliary neurotrophic factor, including Axokine; brain-derived neurotrophic factor; leptin and leptin modulators; other cannabinoid-1 receptor antagonists, including SR-141716 and SLV-319.

In a fourth embodiment, the present invention provides a method for the treatment or prevention of diseases and disorders associated with G-protein coupled cannabinoid receptor activity, which comprises administering to a mammalian species in need of treatment a therapeutically effective amount of a compound of formula I.

In a preferred embodiment, the present invention provides a method for the treatment of diseases or disorders associated with the activity of the CB-1 receptor, which comprises administering to a mammalian species in need of treatment a therapeutically effective amount of a compound of formula I.

In another preferred embodiment, the present invention provides a method for the treatment of bulimia, obesity or any disease resulting in the patient becoming overweight, which comprises administering to a mammalian species in need of treatment a therapeutically effective amount of a compound of formula I.

In another preferred embodiment, the present invention provides a method for the treatment of metabolic disorders, eating disorders and appetitive disorders, including treatment of the conditions associated with those disorders, such as obesity, diabetes, arteriosclerosis, hypertension, polycystic ovary disease, cardiovascular disease, osteoarthritis, dermatological disorders, hypertension, insulin resistance, hypercholesterolemia, reduced HDL, hypertriglyceridemia, cholelithiasis and sleep disorders, hyperlipidemic conditions, bulimia nervosa and compulsive eating disorders, which comprises administering to a mammalian species in need of treatment a therapeutically effective amount of a compound of formula I.

In another preferred embodiment, the present invention provides a method for the treatment of obesity due to genetic or environmental causes, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure, which comprises administering to a mammalian species in need of treatment a therapeutically effective amount of a compound of formula I.

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, cyano, mercapto, alkylthio, heterocyclyl, aryl, heteroaryl, carboxyl, carbalkoyl, carboxamido, carbonyl, alkyl, alkenyl, alkynyl, nitro, amino, alkoxyl, aryloxyl, heteroaryloxyl, amido, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, mercapto, and alkylthio.

Unless otherwise indicated, the term "alkynyl" as used herein by itself or as part of another group refers to straight or branched chain radicals of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, mercapto, and alkylthio.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the rings and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

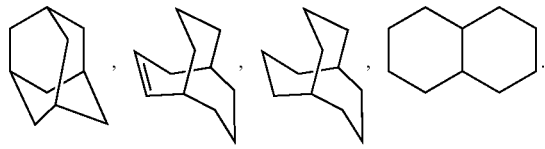

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, mercapto, and alkylthio.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl, 1-naphthyl and 2-naphthyl) and may optionally include one to three additional carbocyclic or heterocyclic fused rings, for example

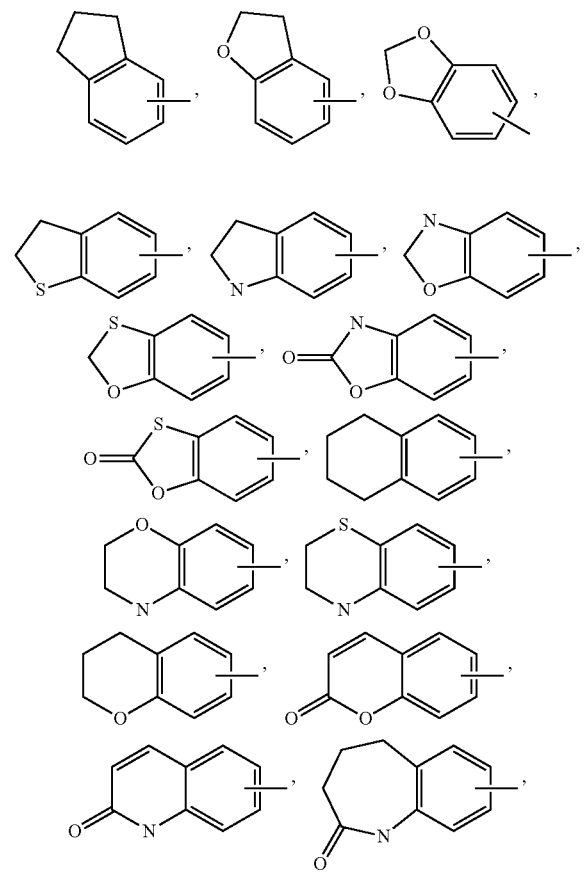

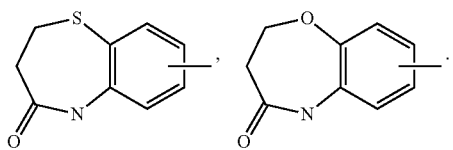

Further, "aryl", as defined herein, may optionally be substituted with one or more functional groups, such as halo, alkyl, alkenyl, alkynyl, cycloalkyl, cycloalkylalkyl, heterocyclyl, heterocycloalkyl, aryl, heteroaryl, arylalkyl, arylalkenyl, heteroarylalkyl, heteroarylalkenyl, haloalkyl, $CF_3$, hydroxy, alkoxy, haloalkoxy, $OCF_3$, $OCF_2H$, aryloxy, heteroaryloxy, arylalkoxy, alkylcarbonyloxy, arylcarbonyloxy, aryloxyalkyl, alkylcarbonyl, arylcarbonyl, alkoxycarbonyl, aminocarbonyl, alkylaminocarbonyl, arylaminocarbonyl, aminocarbonylaryl, heteroarylheteroaryl, nitro, cyano, arylazo, amino, substituted amino wherein the amino includes 1 or 2 substituents (which are alkyl or aryl), alkylcarbonylamino, arylcarbonylamino, alkylsulfonylamino, arylsulfonylamino, mercapto, alkylthio, arylthio, alkoxyarylthio, heteroarylthio, arylsulfinyl, alkylsulfonyl, arylsulfonyl, arylthioalkyl, arylsulfinylalkyl, arylsulfonylalkyl, alkylsulfonylalkyl, or arylsulfonaminocarbonyl.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur. Such rings may be fused to an aryl, cycloalkyl, heteroaryl or heterocyclyl group and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

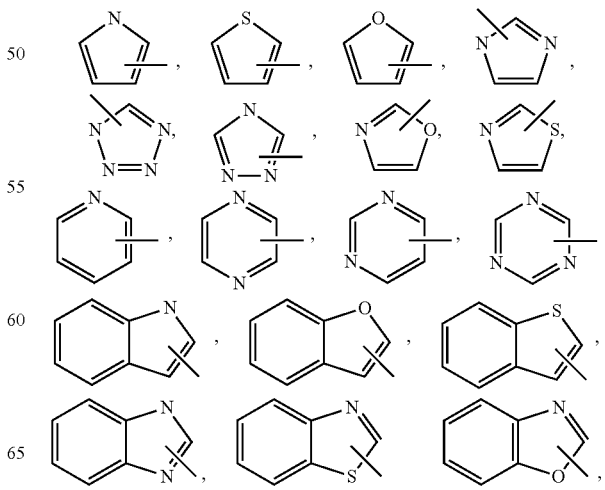

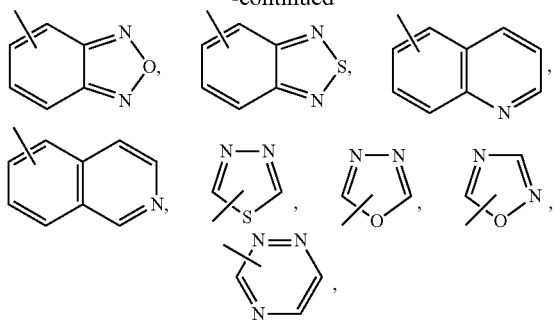

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable, 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups, respectively, as defined above having an aryl substituent as defined above. Representative examples of arylalkyl include, but are not limited to, benzyl, 2-phenylethyl, 3-phenylpropyl, benzhydryl and naphthylmethyl and the like.

The terms "alkoxy", "aryloxy", "heteroaryloxy", "arylalkyloxy" or "heteroarylalkyloxy" as employed herein alone or as part of another group include, respectively, alkyl, aryl, heteroaryl, arylalkyl and heteroarylalkyl groups as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein alone or as part of another group, refers to a —CN group.

The term "methylene," as used herein alone or as part of another group, refers to a —CH$_2$— group.

The term "nitro," as used herein alone or as part of another group, refers to a —NO$_2$ group.

The term "acyl", as employed herein alone or as part of another group includes, alkyl, aryl, heteroaryl, arylalkyl and heteroarylalkyl groups as defined above linked through a carbonyl group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by a halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid or lysine or arginine, or such as benzoic acid, or with organic sulfonic acids, such as ($C_1$-$C_4$) alkyl or arylsulfonic acids which are unsubstituted or substituted, for example by a halogen, for example methanesulfonic acid or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or tri-hydroxy(lower)alkylamine, for example mono, di or triethanolamine Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate and acetate salts.

Preferred salts of the compounds of formula I which contain an acid group include sodium, potassium and magnesium salts and pharmaceutically acceptable organic amine salts.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property or biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyl group of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives appears in:

*The Practice of Medicinal Chemistry*, Camille G. Wermuth et al., Ch 31, (Academic Press, 1996);

*Hydrolysis in Drug and Prodrug Metabolism*, Bernard Testa and Joachim M. Mayer, (Wiley-VCH, 2003);

*Design of Prodrugs*, edited by H. Bundgaard, (Elsevier, 1985);

*A Textbook of Drug Design and Development*, P. Krogsgaard-Larson and H. Bundgaard, eds. Ch 5, pp. 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including those within any of the R substituents. Consequently, compounds of formula I can exist in enantiomeric or diastereomeric forms or in mixtures thereof. The processes for preparation can utilize racemates, enantiomers or diastereomers as starting materials. In order to prepare diastereomeric or enantiomeric products, conventional methods for isomer separation may be employed. These include, for example, chromatographic techniques, chiral HPLC, fractional crystallization, and sequences of derivatization, separation and de-derivatization.

The compounds of formula I of the invention can be prepared as shown below in the following descriptions and reaction schemes, as well as by using relevant published literature procedures that may be used by one skilled in the art. Exemplary reagents and procedures for these reactions appear hereinafter and in the working Examples.

The following abbreviations may be employed in the descriptions, schemes, working Examples and elsewhere herein:

Ac=acetyl
AcCN or MeCN=acetonitrile
AcOH=acetic acid
Boc=tert-butoxycarbonyl
BINAP=2,2'-bis(diphenylphosphino)-1,1'-binaphthyl
Brine=saturated aqueous sodium chloride solution
Chiralpak®=Trademark of Chiral Technologies, Inc. Eaton, Pa.
DCE=1,2-dichloroethane
DCM=dichloromethane
DIPEA=N,N-diisopropylethylamine
DMF=N,N-dimethylformamide
EDAC=1-(3-Dimethylaminopropyl)-3-ethylcarbodiimide hydrochloride
EtOAc=ethyl acetate
$Et_3N$=triethylamine
$Et_2O$=diethyl ether
$Et_3SiH$=triethylsilane
HOBt=1-hydroxybenzotriazole hydrate
HPLC=high performance liquid chromatography
LAH=lithium aluminum hydride
LG=leaving group such as chloride, bromide, methanesulfonate or trifluoromethanesulfonate.
MeOH=methanol
MS or Mass Spec=mass spectrometry
$NaB(OAc)_3H$=sodium triacetoxyborohydride
NaOH=sodium hydroxide
NMM=N-methylmorpholine
PG=protecting group
PXPd=dichlorobis(chlorodi-tert-butylphosphine)palladium
RT=room temperature
SEM=2-(trimethylsilyl)ethoxymethyl
TFA=trifluoroacetic acid
THF=tetrahydrofuran
THQ=tetrahydroquinoline
mp=melting point
min=minute(s)
h=hour(s)
L=liter(s)
mL=milliliter(s)
µL=microliter(s)
g=gram(s)
mg=milligram(s)
mol=mole(s)
mmol=millimole(s)
nM=nanomolar Compounds of the present invention may be prepared by procedures illustrated in the accompanying schemes.

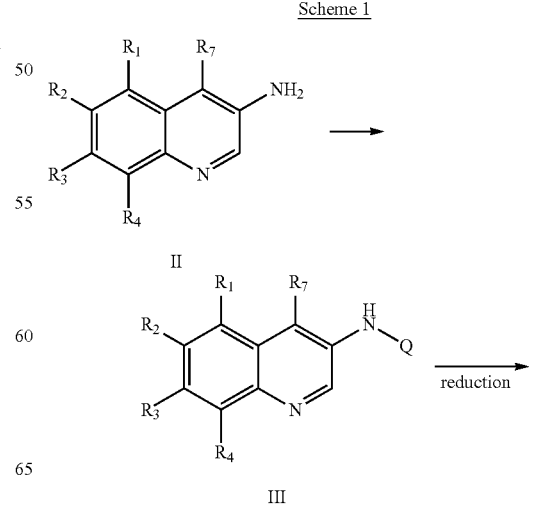

Scheme 1

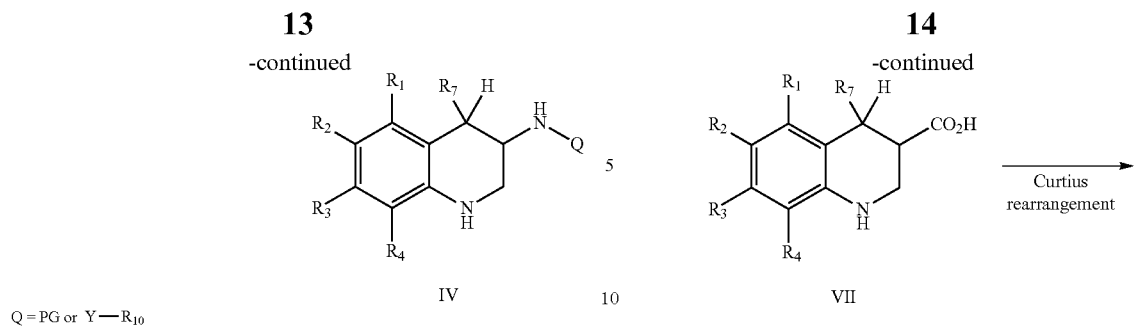

Q = PG or Y—R₁₀

As illustrated in Scheme 1, the amino group of compound II can be suitably protected by, for example, a tert-butyloxycarbonyl, or derivatized as in compound I with, for example, a arylsulfonyl group as shown in III. Compound II can be obtained commercially, or can be prepared by methods known in the literature, or can be readily prepared by one skilled in the art. Reduction of III via hydrogenation in the presence of a transition metal catalyst, such as platinum oxide, or palladium hydroxide on carbon affords intermediate IV.

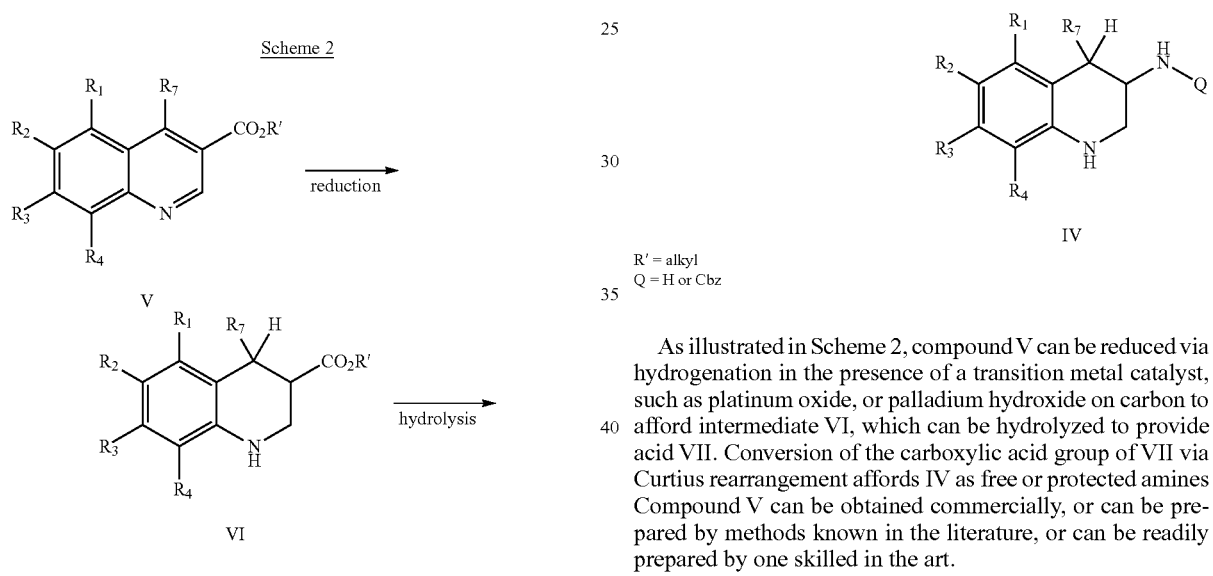

R' = alkyl
Q = H or Cbz

As illustrated in Scheme 2, compound V can be reduced via hydrogenation in the presence of a transition metal catalyst, such as platinum oxide, or palladium hydroxide on carbon to afford intermediate VI, which can be hydrolyzed to provide acid VII. Conversion of the carboxylic acid group of VII via Curtius rearrangement affords IV as free or protected amines Compound V can be obtained commercially, or can be prepared by methods known in the literature, or can be readily prepared by one skilled in the art.

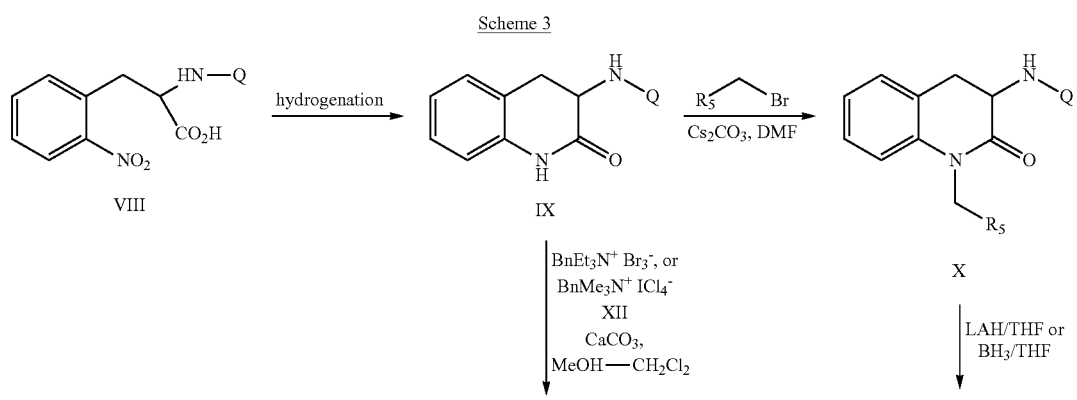

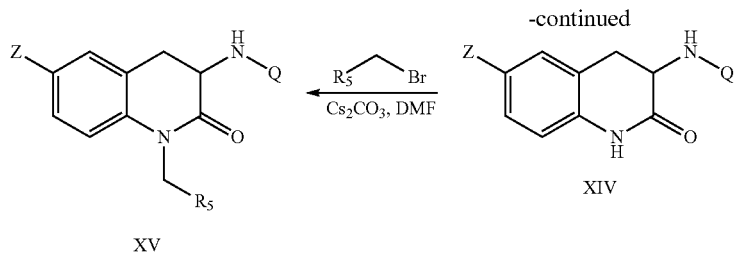
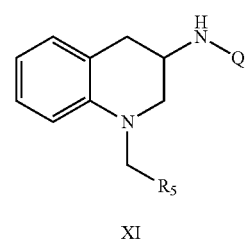

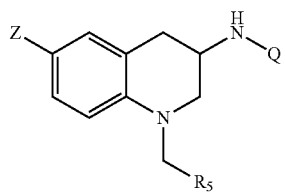

Q = PG or Y—R₁₀
Z = Br or Cl

As illustrated in Scheme 3, reduction of o-nitrophenylalanine derivative VIII via hydrogenation in the presence of a palladium catalyst in an alcoholic solvent, e.g. MeOH, affords cyclized compound IX. Compound VIII in either a racemic or a homochiral form can be obtained commercially, or can be prepared by methods known in the literature, or can be readily prepared by one skilled in the art. It is understood that non-aromatic carbons of the THQ ring system can optionally be substituted with $R_7$, $R_{7a}$, $R_8$ as specified in the general formula I. Reaction of IX with an alkylating reagent, such as a bromide in the presence of a base, e.g. cesium carbonate, provides compound X, which can be reduced to XI with a reducing agent, e.g. borane/THF complex. Treatment of XI with an appropriate bromination or chlorination reagent XII in the presence of a base provides compound XIII (Z=Br or Cl). Alternatively, treatment of intermediate IX with a halogenation reagent XII provides compound XIV, which can be converted, upon alkylation and reduction to compound XIII Bromination or clorination reagents XII can be obtained commercially, or can be prepared by methods known in the literature, or can be readily prepared by one skilled in the art. Compounds IX, X, XIV and XV may also be prepared following the procedures and methods disclosed in US 2004/002495 or references contained therein, or by analogy to the procedures and methods disclosed in US 2004/002495 or references contained therein.

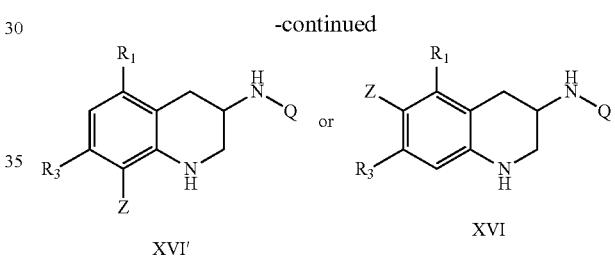

Q = PG or Y—R₁₀
Z = Cl, or Br

As illustrated in Scheme 4, halogenated XVI and XVI' can be prepared by treatment of intermediate IV (prepared as outlined in Scheme 1 and 2) with an appropriate bromination or clorination reagent XII. It is understood that each of the non-aromatic carbons of the THQ ring system can optionally be substituted with $R_6$, $R_{6a}$, $R_7$, $R_{7a}$, $R_8$ as specified in the general formula I.

Scheme 4

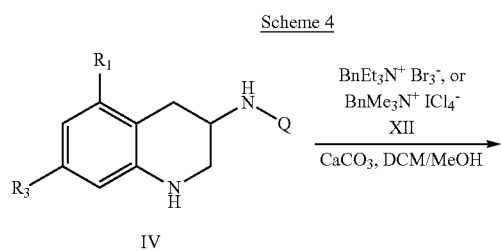

Scheme 5

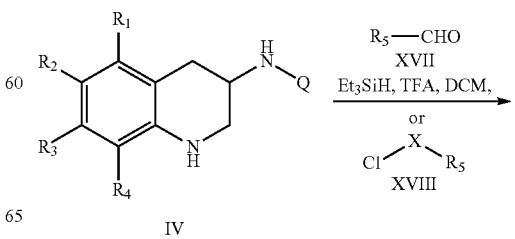

-continued

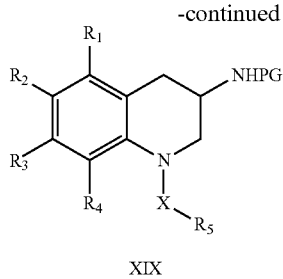

XIX

Scheme 6

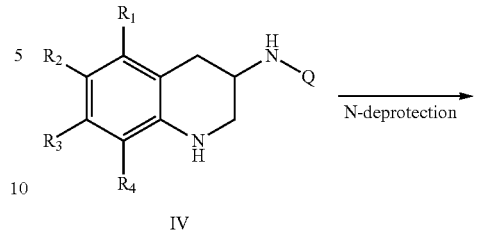

IV

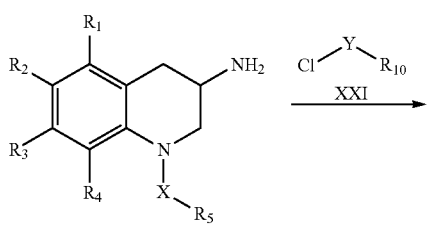

XX

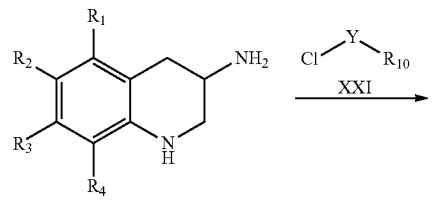

XXII

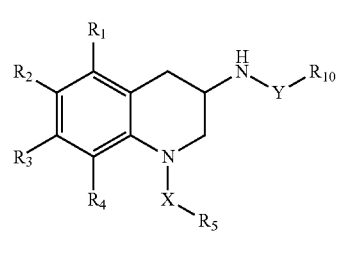

Ia

Q = PG
X = CH₂, CO, SO₂
Y = SO₂, COCO

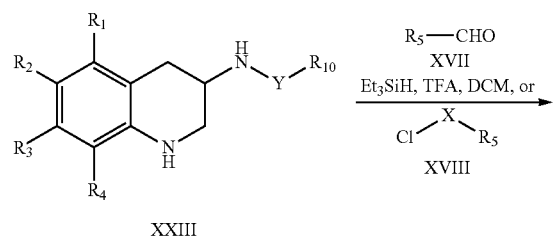

XXIII

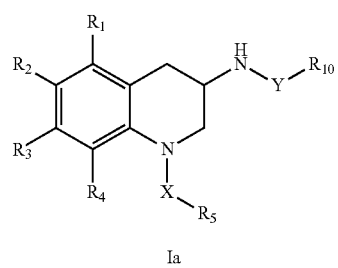

Ia

Q = PG
X = CH₂, CO, SO₂
Y = SO₂, COCO

As illustrated in Scheme 5, compounds of formula Ia can be prepared from intermediate IV (prepared as outlined in Scheme 1 and 2). It is understood that each of the non-aromatic carbons of the THQ ring system can optionally be substituted with $R_6$, $R_{6a}$, $R_7$, $R_{7a}$, $R_8$ as specified in the general formula I. Treatment of IV with aldehyde XVII in the presence of triethylsilane and trifluoroacetic acid, or sodium triacetoxyborohydride affords intermediate XIX (where X=CH₂). Alternatively, treatment of IV with reagent XVIII in the presence of a base provides intermediate XIX (for example, where X=SO₂, or CO, or COO). Removal of the N-protection group (e.g. Boc) can be achieved by treatment of XIX with an acid (e.g. hydrochloric acid in dioxane, or trifluoroacetic acid in methylene chloride) to provide intermediate XX. Treatment of XX with reagent XXI in the presence of a base provides compounds of formula Ia. Reagents XVII, XVIII and XXI can be obtained commercially, or can be prepared by methods known in the literature, or can be readily prepared by one skilled in the art.

Alternatively, compounds of formula Ia can be prepared as illustrated in Scheme 6. Removal of the N-protection group (e.g. Boc) of compound IV can be achieved by treatment with an acid (e.g. hydrochloric acid in dioxane, or trifluoroacetic acid in methylene chloride) to provide intermediate XXII. Treatment of XXII with a reagent XXI in the presence of a base provides intermediate XXIII. Treatment of XXIII with an aldehyde XVII in the presence of triethylsilane and trifluoroacetic acid, or sodium triacetoxyborohydride affords compound 1a (where X=CH₂). Alternatively, treatment of XXIII with a reagent XVIII in the presence of a base affords compound 1a (for example, where X=SO₂, or CO, or COO).

Scheme 7

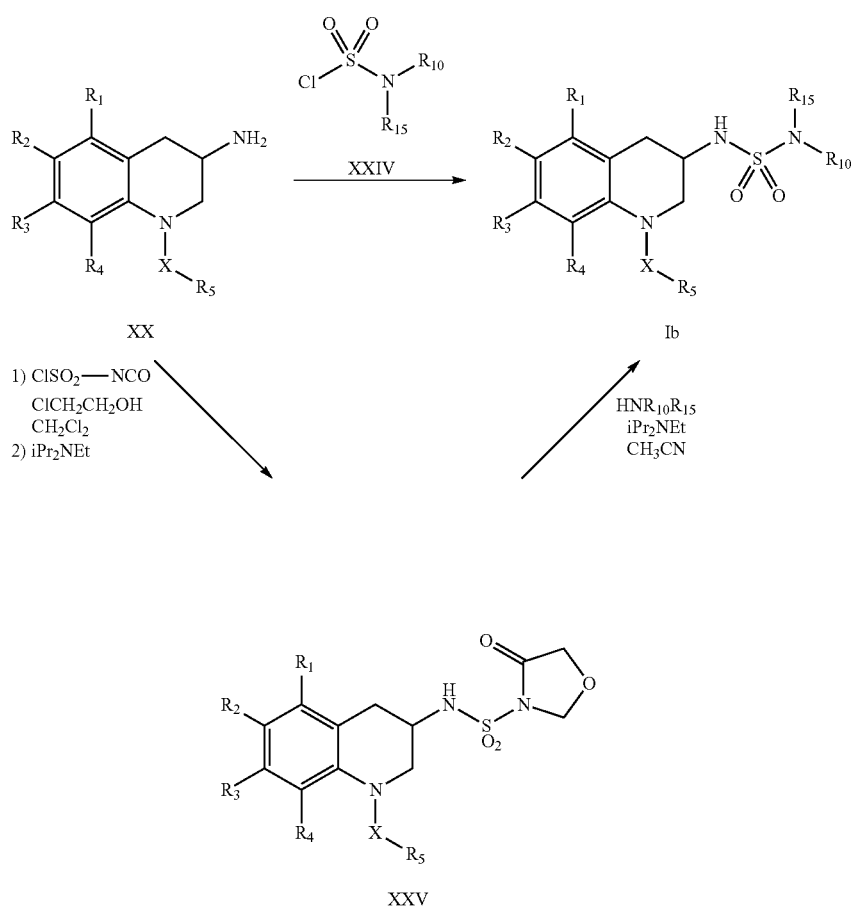

As illustrated in Scheme 7, compounds of formula Ib can be prepared from intermediate XX, which are prepared as outlined in Scheme 5. It is understood that each of the non-aromatic carbons of the THQ ring system can optionally be substituted with $R_6$, $R_{6a}$, $R_7$, $R_{7a}$, $R_8$ as specified in the general formula I. Treatment of XX with a reagent XXIV in the presence of a base provides compound Ib. Alternatively, Ib can also be prepared by reaction of intermediate XXV with a primary or a secondary amine in acetonitrile in the presence of a tertiary amine (e.g. diisopropylethylamine) Intermediate XXV can be prepared by treatment of intermediate XX with the reaction adduct of 2-chloroethanol and chlorosulfonyl isocyanate according to the procedures reported by L. Ducry, et. al. (*Helv. Chim. Acta.* 82, pp 2432-2447, (1999)).

Scheme 8

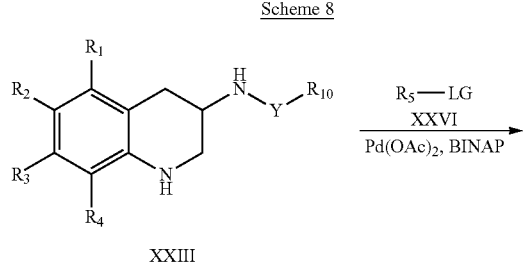

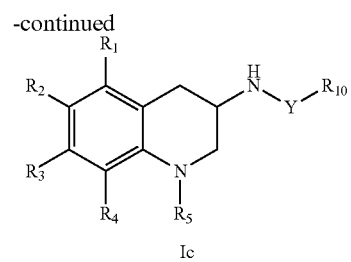

LG = Br, I, or OTf
$R_5$ = aryl, heteroaryl

As illustrated in Scheme 8, compounds of formula Ic can be prepared from intermediate XXIII (prepared as outlined in Scheme 6). It is understood that each of the non-aromatic carbons of the THQ ring system can optionally be substituted with $R_6$, $R_{6a}$, $R_7$, $R_{7a}$, $R_8$ as specified in the general formula I. Treatment of XXIII with a reagent XXVI in the presence of a palladium catalyst (e.g. Pd(OAc)$_2$ and a ligand (e.g. BINAP) provides compounds of formula Ic. Intermediate XXVI can be obtained commercially, or can be prepared by methods known in the literature, or can be readily prepared by one skilled in the art.

Scheme 9

R = Br, I, OTf
R' = aryl, heteroaryl or alkenyl
Y = N or O

As illustrated in Scheme 9, compounds of formula Ie can be prepared via C—C bond coupling by treatment of intermediate Id with an appropriate aryl or heteroaryl boronic acid, or an aryl or heteroaryl tin reagent of formula XXVII in the presence of a palladium catalyst. Compounds of formula If can be prepared via C—N or C—O bond coupling by treatment of intermediate Id with a heterocyclic (e.g. a lactam, pyridone, imidazole or pyrizole) or a hydroxyarene (e.g. phenol), or a hydroxyheteroarene of formula XXVIII in the presence of a copper catalyst. Compounds of formula Ig can be prepared by treatment of intermediate Id with zinc cyanide in the presence of a palladium catalyst, e.g. $Pd(Ph_3P)_4$. It is understood that each of the non-aromatic carbons of the THQ ring system can optionally be substituted with $R_6$, $R_{6a}$, $R_7$, $R_{7a}$, $R_8$ as specified in the general formula I. Reagents XXVII and XXVIII can be obtained commercially, or can be prepared by methods known in the literature, or can be readily prepared by one skilled in the art.

Scheme 10

LG = Br, or I

As illustrated in Scheme 10, compounds of formula Ih can be prepared by treatment of Ia with an alkylating reagent XXIX in the presence of a base. It is understood that each of the non-aromatic carbons of the THQ ring system can optionally be substituted with $R_6$, $R_{6a}$, $R_7$, $R_{7a}$, $R_8$ as specified in the general formula I. Reagent XXIX can be obtained commercially, or can be prepared by methods known in the literature, or can be readily prepared by one skilled in the art.

It is understood that the reagents mentioned throughout are example reagents, not meant to be limiting. Those skilled in the art will recognize that there are many acids (trifluoroacetic acid, hydrochloric acid, polyphosphoric acid, etc.), many bases (triethylamine, sodium hydride, potassium methoxide, etc.), many oxidants (hydrogen peroxide, 3-chloroperoxybenzoic acid, etc.), many hydrogenation catalysts (palladium, platinum oxide, Raney® Nickel, etc.), and so on that may be employed to synthesize the compounds of the invention. In some cases alternative reagents known to those skilled in the art will be superior to those specifically mentioned. Alternative reagents may be found in Reagents For Organic Synthesis (Fieser and Fieser, John Wiley & Sons) and Compendium of Organic Synthetic Methods (John Wiley & Sons).

In general, the interchange of functional groups within all the various R groups may be accomplished according to the methods and procedures described in Compendium of Organic Synthetic Methods (John Wiley & Sons) and Comprehensive Organic Transformations—A Guide To Functional Group Preparations (R. C. Larock, VCH Publishers, 1989). It is understood that during the course of manipulating any functional group within any of the various R groups, standard protecting groups, as described in Protective Groups in Organic Synthesis, may be employed to avoid undesired reaction of any other functional group.

Standard protecting groups may be used at any stage of synthesis, for example in manipulating a functional group to convert one compound of formula I to another compound of formula I, or in manipulating a functional group to convert one protected amine, for example, amine II to another protected amine II, or to avoid undesired reaction during the conversion of amines, for example amine XX to compounds of formula I, or during the sequence of steps leading to the formation of protected amine, for example amine II.

The following examples serve to better illustrate, but not limit, some of the preferred embodiments of the invention.

Example 1

(S)—N-(6-Cyano-1-thiazol-5-ylmethyl-1,2,3,4-tetrahydroquinolin-3-yl)-benzenesulfonamide

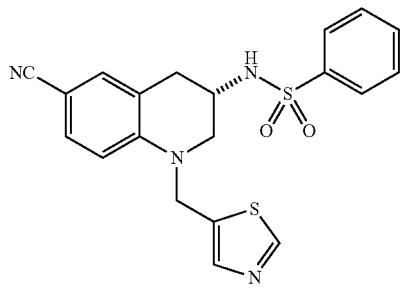

1A. tert-Butyl 1,2,3,4-tetrahydroquinolin-3-yl-carbamate

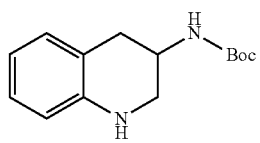

To a solution of 3-aminoquinoline (4.32 g, 30 mmol) in anhydrous THF (100 mL) under argon at RT was added dropwise sodium bis(trimethylsilyl)amide (1 M solution in THF, 63 mL, 63 mmol). The resulting dark brown mixture was treated with di-tert-butyl dicarbonate (7.2 g, 33 mmol). After stirring at RT for 2 h, the reaction was quenched with water (30 mL), and 1N aqueous HCl (45 mL). The aqueous layer was separated and extracted with EtOAc (2×70 mL). The combined organics were washed with brine, dried ($Na_2SO_4$) and concentrated. The residue was chromatographed (silica gel) eluting with EtOAc (0 to 50%) in hexane to give 3-quinolinylcarbamic acid, 1,1-dimethylethyl ester (6.5 g, 89% yield) as an off-white solid.

To a solution of 3-quinolinylcarbamic acid, 1,1-dimethylethyl ester (6.0 g, 24.56 mmol) in MeOH (150 mL) was added acetic acid (18 mL). The mixture was bubbled with argon for 15 min, then palladium hydroxide (20 weight % palladium on carbon) (1.2 g) was added. The resulting suspension was subjected to hydrogenation under 45 psi of pressure for 16 h., then filtered. The filtrate was concentrated and the residue taken in $CH_2Cl_2$. The resulting $CH_2Cl_2$ solution was washed with saturated aqueous $NaHCO_3$, brine, dried ($Na_2SO_4$) and concentrated. The residue was chromatographed (silica gel) eluting with EtOAc (0 to 50%) in hexane to give 1A (4.6 g, 75% yield) as a white solid.

1B. (6-Bromo-1,2,3,4-tetrahydroquinolin-3-yl)-carbamic acid tert-butyl ester

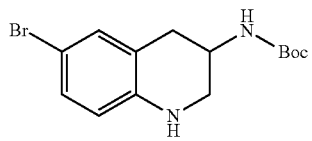

To a solution of 1A (2.7 g, 10.9 mmol) in THF (50 mL) at RT was added dropwise a solution of pyridinium tribromide (3.83 g, 0.41 mmol) in THF (50 mL). After addition, the reaction mixture was stirred for 15 min, then water (60 mL) and ether (60 mL) added. The aqueous layer was separated, and extracted with EtOAc (2×50 mL). The combined organics were washed with brine, dried ($Na_2SO_4$) and concentrated. The residue was chromatographed (silica gel) eluting with EtOAc (0 to 50%) in hexane to give the title compound (2.5 g, 70% yield) as a white solid.

1C. (6-Cyano-1,2,3,4-tetrahydroquinolin-3-yl)-carbamic acid tert-butyl ester

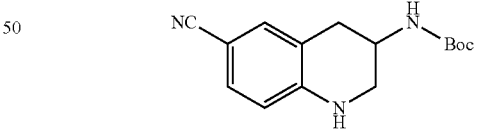

A solution of 1B (250 mg, 0.76 mmol) and zinc cyanide (88 mg, 0.75 mmol) in DMF (2.5 mL) was bubbled with argon for 10 min, then tetrakis-(triphenylphosphine)palladium(0) (65 mg, 0.057 mmol) was added and the solution was deoxygenated. The reaction mixture was then heated at 90° C. for 4 h, cooled to RT, and partitioned between EtOAc and water. The aqueous layer was separated and extracted with EtOAc (2×20 mL). The combined EtOAc extracts were washed with brine, dried ($Na_2SO_4$) and concentrated. The residue was chromatographed (silica gel) eluting with EtOAc (0 to 60%) in hexane to give the title compound (140 mg, 67% yield) as a white solid.

1D. 3-Amino-1,2,3,4-tetrahydroquinoline-6-carbonitrile, dihydrochloride

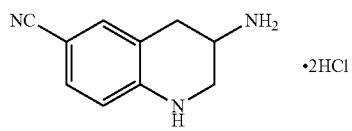

To a solution of 1C (546 mg, 2 mmol) in $CH_2Cl_2$ (5 mL) at 0° C. was added 4 M HCl in dioxane (4 mL, 16 mmol). After addition, the reaction mixture was stirred at RT for 2 h, then concentrated. The residue was stripped with ether (3×), and the resulting off-white solid dried in vacuo to afford the title compound (490 mg, 100%).

1E. (S)—N—((S)-6-Cyano-1,2,3,4-tetrahydroquinolin-3-yl)-2-hydroxy-2-phenylacetamide

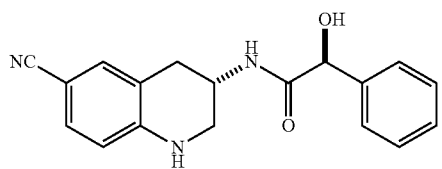

To a solution of 1D (10.03 g, 40.7 mmol) in DMF (100 mL) was added (S)-(+)-mandelic acid (7.45 g, 48.9 mmol), followed by EDAC (9.37 g, 48.9 mmol), HOBt (7.49 g, 48.9 mmol) and NMM (16.1 mL, 146.1 mmol). The reaction mixture was stirred at RT overnight, then diluted with EtOAc (200 mL), washed with water (50 mL×3), 1N aqueous HCl (50 mL), water (50 mL) and brine, dried ($Na_2SO_4$) and concentrated. The residue was chromatographed (silica gel) eluting with EtOAc/hexane (2:1), and the purified compound crystallized from acetone (3×) to give the title compound as the (S, S) diastereoisomer (2.54 g, 20% yield).

1F. (S)-3-Amino-1,2,3,4-tetrahydroquinoline-6-carbonitrile

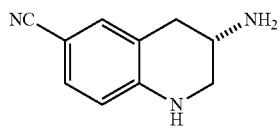

To a solution of 1E (2.5 g, 8.14 mmol) in EtOH (25 mL) was added 15% aqueous sulfuric acid (25 mL). The resulting mixture was refluxed overnight, then cooled to RT. After removal of most of the EtOH, the mixture was diluted with water (200 mL), extracted with $CH_2Cl_2$ (3×50 mL). The aqueous layer was basified with 4N NaOH to pH=10, then extracted with $CH_2Cl_2$ (3×50 mL). The combined organics were washed with brine, dried ($Na_2SO_4$) and concentrated. The residue was crystallized from EtOAc/hexane to afford the title compound (1.026 g, 73% yield).

1G. (S)—N-(6-Cyano-1,2,3,4-tetrahydro-quinolin-3-yl)-benzenesulfonamide

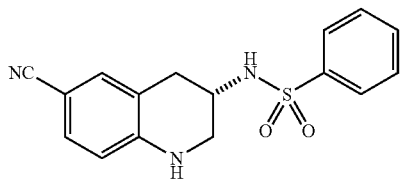

To a suspension of 1F (103.9 mg, 0.6 mmol) in $CH_3CN$ (3 mL) at RT under argon was added DIPEA (0.11 mL, 0.66 mmol), followed by dropwise addition of benzene sulfonylchloride (0.08 mL, 0.63 mmol). The reaction mixture was stirred at RT for 1.5 h, then concentrated under reduced pressure. The residue was taken into EtOAc, washed with water, brine, dried ($Na_2SO_4$), and concentrated. The resulting residue was chromatographed (silica gel) eluting with EtOAc (30-50%) in hexane to give the title compound (170 mg, 90%). HPLC: 99% at 5.2 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 314 $[M+H]^+$.

1H. (S)—N-(6-Cyano-1-thiazol-5-ylmethyl-1,2,3,4-tetrahydro-quinolin-3-yl)-benzenesulfonamide To a solution of 1G (94 mg, 0.3 mmol) and thiazole-5-carbaldehyde (67.9 mg, 0.6 mmol) (prepared following the procedures described in Alessandro Dondoni, et al, *Synthesis*, 11, 998-1001, (1987)) in a mixed solvents of TFA (0.75 mL) and $CH_2Cl_2$ (0.75 mL) was added $Et_3SiH$ (0.096 mL, 0.6 mmol). The resulting mixture was stirred at RT under argon for 18 h, then concentrated under reduced pressure. The residue was diluted with saturated aqueous $NaHCO_3$, then extracted with EtOAc (3×20 mL). The combined EtOAc extracts were washed with brine, dried ($Na_2SO_4$), and concentrated. The resulting residue was chromatographed (silica gel) eluting with EtOAc (50-90%) in hexane to give the title compound as an off-white solid (70 mg, 57%). HPLC: 99% at 5.43 min (retention time) (Conditions: Zorbax SB C18 (4.6× 75 mm); Eluted with 0% to 100% B, 8 min gradient (A=90% $H_2O$–10% MeOH–0.1% $H_3PO_4$ and B=10% $H_2O$–90% MeOH–0.1% $H_3PO_4$), Flow rate at 2.5 mL/min, UV detection at 220 nm). MS (ES): m/z 411 $[M+H]^+$; Chiral HPLC 100% e.e.; retention time=32.9 min; Conditions: AD (4.6× 250 mm); Eluted with 40% isopropanol in hexane for 50 min at 1 mL/min.

Example 2

(R)—N-(6-Cyano-1-thiazol-5-ylmethyl-1,2,3,4-tetrahydro-quinolin-3-yl)-benzenesulfonamide

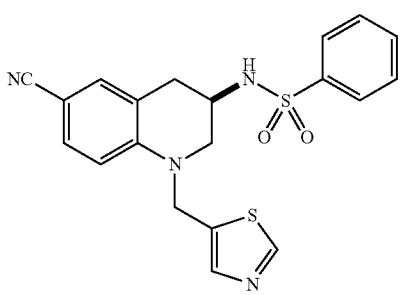

2A. (R)-3-Amino-1,2,3,4-tetrahydroquinoline-6-carbonitrile

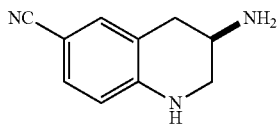

Compound 2A was prepared from the (S, R) diastereomer isolated in Example 1E by procedures analogous to those described in Example 1F.

2B. (R)—N-(6-Cyano-1,2,3,4-tetrahydroquinolin-3-yl)-benzenesulfonamide

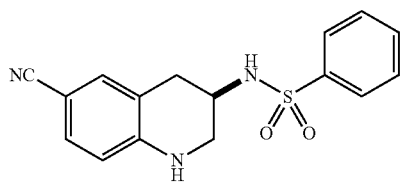

Compound 2B was prepared from 2A by procedures analogous to those described in Example 1G.

2C. (R)—N-(6-Cyano-1-thiazol-5-ylmethyl-1,2,3,4-tetrahydroquinolin-3-yl)-benzenesulfonamide The title compound was prepared from 2B by procedures analogous to those described in Example 1H. HPLC: 99% at 5.45 min (retention time) (Conditions: Zorbax SB C18 (4.6× 75 mm); Eluted with 0% to 100% B, 8 min gradient (A=90% $H_2O$–10% MeOH–0.1% $H_3PO_4$ and B=10% $H_2O$–90% MeOH–0.1% $H_3PO_4$), Flow rate at 2.5 mL/min, UV detection at 220 nm). MS (ES): m/z 411 $[M+H]^+$; Chiral HPLC 100% e.e.; retention time=29.4 min; Conditions: AD (4.6× 250 mm); Eluted with 40% isopropanol in hexane for 50 min at 1 mL/min.

Example 3

(S)—N-(6-Cyano-1-thiazol-5-ylmethyl-1,2,3,4-tetrahydroquinolin-3-yl)-N-methyl-benzenesulfonamide

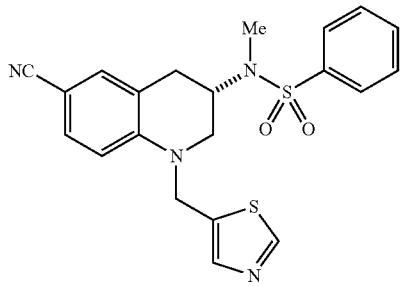

To a solution of 1G (50 mg, 0.12 mmol) in ethylene glycol dimethyl ether (1.5 mL) at RT was added NaH (5.1 mg, 0.13 mmol). The resulting mixture was heated at reflux under argon for 1 h, then cooled to RT, iodomethane (27 uL, 0.42 mmol) was added. The reaction was heated at reflux for 4 h. After cooling to RT, the reaction was quenched with water, then extracted with EtOAc (3×10 mL). The combined EtOAc extracts were washed with brine, dried ($Na_2SO_4$), and concentrated. The resulting residue was chromatographed (silica gel) eluting with EtOAc (50-80%) in hexane to give the title compound as a white foam (25 mg, 49%). HPLC: 98% at 5.8 min (retention time) (Conditions: Zorbax SB C18 (4.6×75 mm); Eluted with 0% to 100% B, 8 min gradient (A=90% $H_2O$–10% MeOH–0.1% $H_3PO_4$ and B=10% $H_2O$–90% MeOH–0.1% $H_3PO_4$); Flow rate at 2.5 mL/min, UV detection at 220 nm). MS (ES): m/z 425 $[M+1]^+$. Chiral HPLC 100% e.e.; retention time=39.2 min; Conditions: OD (4.6× 250 mm); Eluted with 40% isopropanol in hexane for 50 min at 1 mL/min.

Example 4

(R)—N-(6-Cyano-1-thiazol-5-ylmethyl-1,2,3,4-tetrahydroquinolin-3-yl)-N-methyl-benzenesulfonamide

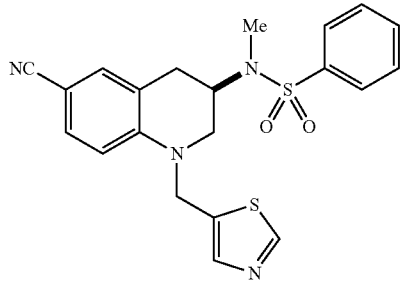

The title compound was prepared from 2C by procedures analogous to those described in Example 3. HPLC: 98% at 5.8 min (retention time) (Conditions: Zorbax SB C18 (4.6×75 mm); Eluted with 0% to 100% B, 8 min gradient (A=90% H$_2$O–10% MeOH–0.1% H$_3$PO$_4$ and B=10% H$_2$O–90% MeOH–0.1% H$_3$PO$_4$); Flow rate at 2.5 mL/min, UV detection at 220 nm). MS (ES): m/z 425 [M+1]$^+$. Chiral HPLC 100% e.e.; retention time=25.3 min; Conditions: OD (4.6× 250 mm); Eluted with 40% isopropanol in hexane for 50 min at 1 mL/min.

Example 5 to 14

Additional compounds of the present invention were prepared by procedures analogous to those described in Example 1. The compounds of Examples 5 to 14 have the following structure,

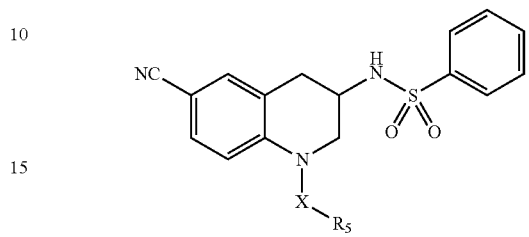

where the group XR$_5$, the stereochemistry, the compound name, retention time, molecular mass, and the procedure employed, are set forth in Table 1. The chromatography techniques used to determine the compound retention times of Table 1 are as follows: HPLC (purity) conditions: Zorbax SB C18 (4.6×75 mm); Eluted with 0% to 100% B, 8 min gradient (A=90% H$_2$O–10% MeOH–0.1% H$_3$PO$_4$ and B=10% H$_2$O–90% MeOH–0.1% H$_3$PO$_4$); Flow rate at 2.5 mL/min, UV detection at 220 nm). LC-MS conditions: Phenom. Luna C18 (4.6×50 mm eluting with 10-90% MeOH/H$_2$O over 4 minutes containing 0.1% TFA; 4 mL/min, monitoring at 220 nm. The molecular mass of the compounds listed in Table 1, where provided, were determined by MS (ES) by the formula m/z.

TABLE 1

| Ex. No. | XR$_5$ | Compound Name | Retention Time (min.)/m/z | See Ex. |
|---|---|---|---|---|
| 5a | —CH$_2$—phenyl | (S)-N-(1-Benzyl-6-cyano-1,2,3,4-tetrahydroquinolin-3-yl)-benzenesulfonamide | 6.87 LCMS/ 404 [M + H]$^+$ | 1H |
| 5b | —CH$_2$—phenyl | (R)-N-(1-Benzyl-6-cyano-1,2,3,4-tetrahydroquinolin-3-yl)-benzenesulfonamide | 6.90 LCMS/ 404 [M + H]$^+$ | 22A |
| 6 | —CH$_2$—(2-Cl-phenyl) | (S)-N-[1-(2-Chloro-benzyl)-6-cyano-1,2,3,4-tetrahydroquinolin-3-yl]-benzenesulfonamide | 7.27 LCMS/ 438 [M + H]$^+$ | 1H |
| 7a | —CH$_2$—(3-Cl-phenyl) | (S)-N-[1-(3-Chloro-benzyl)-6-cyano-1,2,3,4-tetrahydroquinolin-3-yl]-benzenesulfonamide | 7.12 LCMS/ 438 [M + H]$^+$ | 1H |
| 7b | —CH$_2$—(3-Cl-phenyl) | (R)-N-[1-(3-Chloro-benzyl)-6-cyano-1,2,3,4-tetrahydroquinolin-3-yl]-benzenesulfonamide | 7.20 LCMS/ 438 [M + H]$^+$ | 22A |

TABLE 1-continued

| Ex. No. | XR$_5$ | Compound Name | Retention Time (min.)/m/z | See Ex. |
|---|---|---|---|---|
| 8 | —CH$_2$—C$_6$H$_4$—Cl | (S)-N-[1-(4-Chloro-benzyl)-6-cyano-1,2,3,4-tetrahydroquinolin-3-yl]-benzenesulfonamide | 7.20 LCMS/ 438 [M + H]$^+$ | 1H |
| 9 | —CH$_2$-(pyridin-2-yl) | (S)-N-(6-Cyano-1-pyridin-2-ylmethyl-1,2,3,4-tetrahydroquinolin-3-yl)-benzenesulfonamide | 4.75 LCMS/ 405 [M + H]$^+$ | 1H |
| 10 | —CH$_2$-(pyridin-3-yl) | (S)-N-(6-Cyano-1-pyridin-3-ylmethyl-1,2,3,4-tetrahydroquinolin-3-yl)-benzenesulfonamide | 3.95 LCMS/ 405 [M + H]$^+$ | 1H |
| 11 | —CH$_2$-(pyridin-4-yl) | (S)-N-(6-Cyano-1-pyridin-4-ylmethyl-1,2,3,4-tetrahydroquinolin-3-yl)-benzenesulfonamide | 3.88 LCMS/ 405 [M + H]$^+$ | 1H |
| 12 | —CH(CH$_3$)—C$_6$H$_5$ | N-[6-Cyano-1-(1-phenylethyl)-1,2,3,4-tetrahydroquinolin-3-yl]-benzenesulfonamide | 7.04 LCMS/ 418 [M + H]$^+$ | 1H |
| 13 | —CH$_2$CH$_2$—C$_6$H$_5$ | N-(6-Cyano-1-phenethyl-1,2,3,4-tetrahydroquinolin-3-yl)-benzenesulfonamide | 7.23 LCMS/ 418 [M + H]$^+$ | 22A |
| 14 | —CH$_2$-cyclohexyl | (S)-N-(6-Cyano-1-cyclohexylmethyl-1,2,3,4-tetrahydroquinolin-3-yl)-benzenesulfonamide | 7.70 LCMS/ 410 [M + H]$^+$ | 22A |

Example 15 to 20

Additional compounds also prepared by procedures analogous to those described in Example 1. The compounds of Examples 15 to 20 have the following structure, where the group R$_{10}$, the stereochemistry, the compound name, retention time, molecular mass, and the procedure employed, are set forth in Table 2. The chromatography techniques used to determine the compound retention times of Table 2 are as follows: HPLC (purity) conditions: Zorbax SB C18 (4.6×75 mm); Eluted with 0% to 100% B, 8 min gradient (A=90% H$_2$O–10% MeOH–0.1% H$_3$PO$_4$ and B=10% H$_2$O–90% MeOH–0.1% H$_3$PO$_4$); Flow rate at 2.5 mL/min, UV detection at 220 nm). LC-MS conditions: Phenom. Luna C18 (4.6×50 mm eluting with 10-90% MeOH/H$_2$O over 4 minutes containing 0.1% TFA; 4 mL/min, monitoring at 220 nm. The molecular mass of the compounds listed in Table 2, where provided, were determined by MS (ES) by the formula m/z.

TABLE 2

| Ex. No. | R$_{10}$ | Compound Name | Retention Time (min.)/m/z | See Ex. |
|---|---|---|---|---|
| 15 | pyridin-3-yl | Pyridine-3-sulfonic acid[1-(3-chlorobenzyl)-6-cyano-1,2,3,4-tetrahydroquinolin-3-yl)-amide | 6.60 LCMS/ 439 [M + H]$^+$ | 1 |

TABLE 2-continued

| Ex. No. | R₁₀ | Compound Name | Retention Time (min.)/m/z | See Ex. |
|---|---|---|---|---|
| 16 | 2-pyridyl | Pyridine-2-sulfonic acid[1-(3-chlorobenzyl)-6-cyano-1,2,3,4-tetrahydroquinolin-3-yl)-amide | 6.60 LCMS/ 439 [M + H]⁺ | 1 |
| 17 | 2-thienyl | Thiophene-2-sulfonic acid[1-(3-chlorobenzyl)-6-cyano-1,2,3,4-tetrahydroquinolin-3-yl)-amide | 6.95 LCMS/ 444 [M + H]⁺ | 1 |
| 18 | 2-chlorophenyl | (S)-2-Chloro-N-[1-(3-chlorobenzyl)-6-cyano-1,2,3,4-tetrahydroquinolin-3-yl]-benzenesulfonamide | 7.23 LCMS/ 472 [M + H]⁺ | 1 |
| 19 | 3-chlorophenyl | (S)-3-Chloro-N-[1-(3-chlorobenzyl)-6-cyano-1,2,3,4-tetrahydroquinolin-3-yl]-benzenesulfonamide | 7.52 LCMS/ 472 [M + H]⁺ | 1 |
| 20 | 4-chlorophenyl | (S)-4-Chloro-N-[1-(3-chlorobenzyl)-6-cyano-1,2,3,4-tetrahydroquinolin-3-yl]-benzenesulfonamide | 7.54 LCMS/ 472 [M + H]⁺ | 1 |

Example 21

N-(6-chloro-1,2,3,4-tetrahydroquinolin-3-yl)benzenesulfonamide

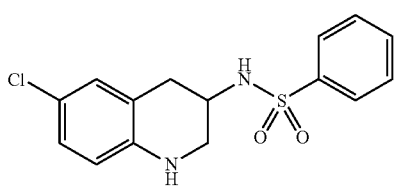

21A. tert-Butyl 6-chloro-1,2,3,4-tetrahydroquinolin-3-ylcarbamate

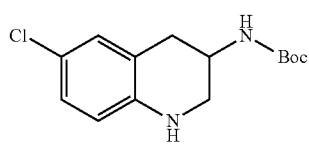

To a solution of 1A (28.3 g, 114 mmol) in acetonitrile (240 mL) at RT was added dropwise a solution of N-chlorosuccinimide (15.22 g, 114 mmol) in acetonitrile (240 mL). After addition, the reaction mixture was stirred for 6 h, then water (500 mL) added. The mixture was extracted with EtOAc (2×500 mL). The combined organics were washed with brine, dried (Na₂SO₄) and concentrated. The residue was chromatographed (silica gel) eluting with EtOAc/hexane 1:5 to give the title compound (10.6 g, 58% yield) as a white solid.

21B. N-(6-chloro-1,2,3,4-tetrahydroquinolin-3-yl)benzenesulfonamide

Compound 21B was prepared from 21A by procedures analogous to those described in Example 1D and 1G.

Example 22

1-Benzyl-6-chloro-1,2,3,4-tetrahydroquinolin-3-amine, dihydrochloride

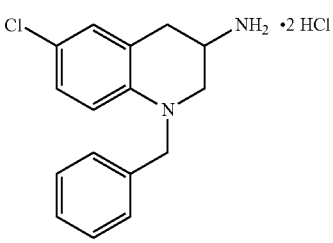

22A. tert-Butyl 1-benzyl-6-chloro-1,2,3,4-tetrahydroquinolin-3-ylcarbamate

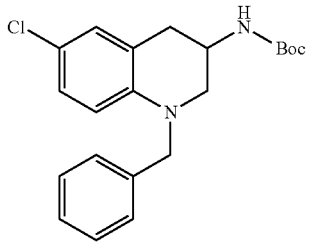

To a solution of 21A (310 mg, 1.096 mmol) in 1,2-dichloroethane (7 mL) was added benzaldehyde (235 mg, 2.193 mmol), followed by sodium triacetoxyboro-hydride (650 mg, 3.069 mmol) and AcOH (200 mg, 3.29 mmol). The reaction mixture was stirred at RT for 4 h, then diluted with EtOAc, washed with saturated aqueous NaHCO$_3$, water, brine, dried (Na$_2$SO$_4$) and concentrated. The resulting residue was chromatographed (silica gel) eluting with EtOAc/hexane 1:5 to give the title compound as light yellow foam (325 mg, 80%).

22B. 1-Benzyl-6-chloro-1,2,3,4-tetrahydroquinolin-3-amine, dihydrochloride

Compound 22B was prepared from 22A by procedures analogous to those described in Example 1D.

Example 23

N-(6-Chloro-1-(pyrazin-2-ylmethyl)-1,2,3,4-tetrahydroquinolin-3-yl)benzenesulfonamide

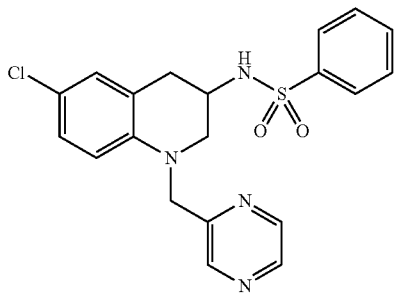

The title compound was synthesized as part of library using the following procedure in a parallel synthesis fashion using 48 well red and blue minireactors.

Typical procedure: To a solution of 21B (21 mg, 0.05 mmol) in DCE (1 mL) at RT was added 2-pyrazinecarboxaldehyde (10.8 mg, 0.1 mmol) followed by addition of scandium triflate (25 mg, 0.1 mmol) and sodium cyanoborohydride (6.2 mg, 0.1 mmol). The reaction mixture was shaken at RT for 48 h, and treated with 1.0 mL methanol for 30 min. Contents were filtered into a synthesis tube rack and the solvent was dried in a speedvac. The resulting residue was chromatographed using Prep HPLC (conditions: Xterra MS-C18 (30×50 mm); Eluted with 10% to 100% B, 6 min gradient. (A=100% water–0.1% TFA and B=acetonitrile with 0.1% TFA); Flow rate at 30 mL/min. UV detection at 220 nm) to give the title compound 23 (6.4 mg, 20%). HPLC: 99% at 1.47 min (retention time) (Conditions: Xterra MS-C18 (2.1× 50 mm); Eluted with 0% to 100% B, 2.75 min gradient. (A=100% water–0.1% TFA and B=acetonitrile with 0.1% TFA); Flow rate at 1 mL/min. UV detection at 220 nm) MS (ES): m/z 415.07 [M+H]$^+$.

Example 24-49

Additional compounds of the present invention were prepared by procedures described in Example 23. The compounds of Examples 24 to 49 have the following structure,

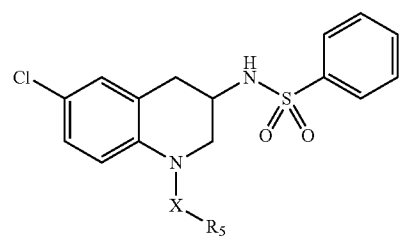

where XR$_5$, the compound name, retention time, molecular mass, and the procedure employed, are set forth in Table 3. The chromatography techniques used to determine the compound retention times of Table 3 are as follows: HPLC (purity) conditions: Xterra MS-C18 (2.1×50 mm); Eluted with 0% to 100% B, 2.75 min gradient. (A=100% water–0.1% TFA and B=acetonitrile with 0.1% TFA); Flow rate at 1 mL/min. UV detection at 220 nm). The molecular mass of the compounds listed in Table 3, where provided, were determined by MS (ES) by the formula m/z using Waters LCT Time of flight mass spec, with a mux 4-way source.

TABLE 3

| Ex. No. | XR$_5$ | Compound Name | Retention Time (min.)/m/z | See Ex. |
|---|---|---|---|---|
| 24 | —CH$_2$-(thiazol-4-yl) | N-(6-Chloro-1-(thiazol-4-ylmethyl)-1,2,3,4-tetrahydroquinolin-3-yl)benzenesulfonamide | 1.57 LCMS/ 420 [M + H]$^+$ | 23 |
| 25 | —CH$_2$-(thiozol-5-yl) | N-(6-Chloro-1-(thiozol-5-ylmethyl)-1,2,3,4-tetrahydroquinolin-3-yl)benzenesulfonamide | 1.39 LCMS/ 420 [M + H]$^+$ | 23 |

TABLE 3-continued

| Ex. No. | XR5 | Compound Name | Retention Time (min.)/m/z | See Ex. |
|---|---|---|---|---|
| 26 | 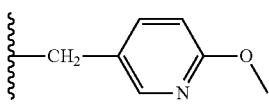 | N-(6-Chloro-1-((6-methoxypyridin-3-yl)methyl)-1,2,3,4-tetrahydroquinolin-3-yl)benzenesulfonamide | 1.59 LCMS/ 444 [M + H]$^+$ | 23 |
| 27 | 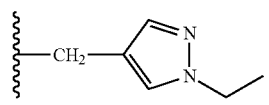 | N-(6-Chloro-1-((1-ethyl-1H-pyrazol-4-yl)methyl)-1,2,3,4-tetrahydroquinolin-3-yl)benzenesulfonamide | 1.49 LCMS/ 431 [M + H]$^+$ | 23 |
| 28 | 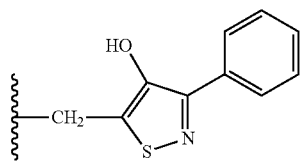 | N-(6-Chloro-1-((4-hydroxy-3-phenylisothiazol-5-yl)methyl)-1,2,3,4-tetrahydroquinolin-3-yl)benzenesulfonamide | 1.60 LCMS/ 512 [M + H]$^+$ | 23 |
| 29 | 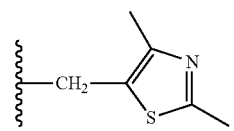 | N-(6-Chloro-1-((2,4-dimethylthiazol-5-yl)methyl)-1,2,3,4-tetrahydroquinolin-3-yl)benzenesulfonamide | 1.47 LCMS/ 448 [M + H]$^+$ | 23 |
| 30 | 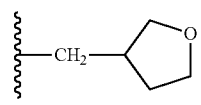 | N-(6-Chloro-1-((tetrahydrofuran-3-yl)methyl)-1,2,3,4-tetrahydroquinolin-3-yl)benzenesulfonamide | 1.44 LCMS/ 407 [M + H]$^+$ | 23 |
| 31 | 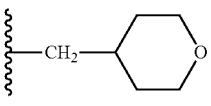 | N-(6-Chloro-1-((tetrahydro-2H-pyran-4-yl)methyl)-1,2,3,4-tetrahydroquinolin-3-yl)benzenesulfonamide | 1.50 LCMS/ 421 [M + H]$^+$ | 23 |
| 32 | 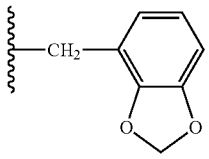 | N-(1-Benzo[d][1,3]dioxol-5-ylmethyl)-6-chloro-1,2,3,4-tetrahydroquinolin-3-yl)benzenesulfonamide | 1.68 LCMS/ 457 [M + H]$^+$ | 23 |
| 33 | 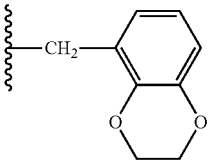 | N-(6-Chloro-1-((2,3-dihydrobenzo[b][1,4]dioxin-5-yl)methyl)-1,2,3,4-tetrahydroquinolin-3-yl)benzenesulfonamide | 1.71 LCMS/ 471 [M + H]$^+$ | 23 |
| 34 | 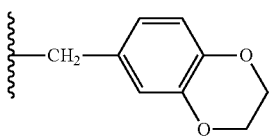 | N-(6-Chloro-1-((2,3-dihydrobenzo[b][1,4]dioxin-6-yl)methyl)-1,2,3,4-tetrahydroquinolin-3-yl)benzenesulfonamide | 1.77 LCMS/ 471 [M + H]$^+$ | 23 |
| 35 | 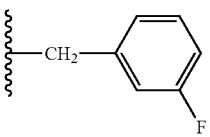 | N-(1-(3-Fluorobenzyl)-6-Chloro-1,2,3,4-tetrahydroquinolin-3-yl)benzenesulfonamide | 1.77 LCMS/ 431 [M + H]$^+$ | 23 |
| 36 | 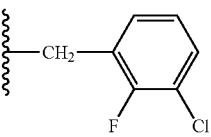 | N-(1-(3-Chloro-2-fluorobenzyl)-6-chloro-1,2,3,4-tetrahydroquinolin-3-yl)benzenesulfonamide | 1.84 LCMS/ 465 [M + H]$^+$ | 23 |

TABLE 3-continued

| Ex. No. | XR₅ | Compound Name | Retention Time (min.)/m/z | See Ex. |
|---|---|---|---|---|
| 37 | -CH₂-(3,5-difluorophenyl) | N-(1-(3,5-Difluorobenzyl)-6-Chloro-1,2,3,4-tetrahydroquinolin-3-yl)benzenesulfonamide | 1.95 LCMS/ 449 [M + H]⁺ | 23 |
| 38 | -CH₂-(2,4-difluorophenyl) | N-(1-(2,4-Difluorobenzyl)-6-chloro-1,2,3,4-tetrahydroquinolin-3-yl)benzenesulfonamide | 1.76 LCMS/ 449 [M + H]⁺ | 23 |
| 39 | -CH₂-(5-fluoro-2-methoxyphenyl) | N-(1-(5-Fluoro-2-methoxybenzyl)-6-chloro-1,2,3,4-tetrahydroquinolin-3-yl)benzenesulfonamide | 1.81 LCMS/ 461 [M + H]⁺ | 23 |
| 40 | -CH₂-(3-cyanophenyl) | N-(1-(3-Cyanobenzyl)-6-chloro-1,2,3,4-tetrahydroquinolin-3-yl)benzenesulfonamide | 1.62 LCMS/ 438 [M + H]⁺ | 23 |
| 41 | -CH₂-(2-cyanophenyl) | N-(1-(2-Cyanobenzyl)-6-chloro-1,2,3,4-tetrahydroquinolin-3-yl)benzenesulfonamide | 1.60 LCMS/ 438 [M + H]⁺ | 23 |
| 42 | -CH₂-(4-cyanomethylphenyl) | N-(1-(4-Cyanomethyl)benzyl)-6-chloro-1,2,3,4-tetrahydroquinolin-3-yl)benzenesulfonamide | 1.67 LCMS/ 452 [M + H]⁺ | 23 |
| 43 | -CH₂-(cyano(phenyl)) | N-(6-Chloro-1-(2-cyano-2-phenylethyl)-1,2,3,4-tetrahydroquinolin-3-yl)benzenesulfonamide | 1.67 LCMS/ 452 [M + H]⁺ | 23 |
| 44 | -CH₂-(4-(3-(dimethylamino)propoxy)phenyl) | N-(1-(4-(3-(Dimethylamino)propoxy)benzyl)-6-chloro-1,2,3,4-tetrahydroquinolin-3-yl)benzenesulfonamide | 1.28 LCMS/ 514 [M + H]⁺ | 23 |
| 45 | -CH₂-cyclohexyl | N-(6-Chloro-1-(cyclohexylmethyl)-1,2,3,4-tetrahydroquinolin-3-yl)benzenesulfonamide | 2.11 LCMS/ 419 [M + H]⁺ | 23 |

TABLE 3-continued

| Ex. No. | XR$_5$ | Compound Name | Retention Time (min.)/m/z | See Ex. |
|---|---|---|---|---|
| 46 | ⁓—CH$_2$—cyclopentyl | N-(6-Chloro-1-(cyclopentylmethyl)-1,2,3,4-tetrahydroquinolin-3-yl)benzenesulfonamide | 1.98 LCMS/ 405 [M + H]$^+$ | 23 |
| 47 | ⁓—CH$_2$—cyclopropyl | N-(6-Chloro-1-(cyclopropylmethyl)-1,2,3,4-tetrahydroquinolin-3-yl)benzenesulfonamide | 1.74 LCMS/ 377 [M + H]$^+$ | 23 |
| 48 | ⁓—CH$_2$—CH(CH$_3$)$_2$ | N-(6-Chloro-1-isopentyl-1,2,3,4-tetrahydroquinolin-3-yl)benzenesulfonamide | 2.04 LCMS/ 393 [M + H]$^+$ | 23 |
| 49 | ⁓—CH$_2$—CH$_2$CH$_3$ | N-(6-Chloro-1-butyl-1,2,3,4-tetrahydroquinolin-3-yl)benzenesulfonamide | 1.79 LCMS/ 379 [M + H]$^+$ | 23 |

Example 50

N-(1-Benzyl-6-chloro-1,2,3,4-tetrahydroquinolin-3-yl)benzenesulfonamide

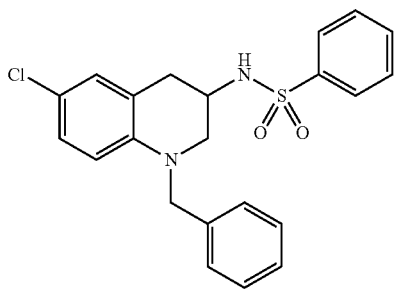

The title compound was synthesized as part of library using the following procedure in a parallel synthesis fashion using 48 well red and blue minireactors. Typical procedure: To a solution of 22B (14 mg, 0.05 mmol) in DCE (0.5 mL) at RT was added NMM (0.109 mL, 0.1 mmol), followed by addition of benzene sulfonylchloride (17.6 mg, 0.1 mmol) in DCE (0.5 uL). The reaction mixture was shaken at RT for 24 h, and treated with 100 mg of PS-Trisamine (4 mmol/g loading) for 2 h to remove excess sulfonyl chloride. Contents were filtered into a synthesis tube rack (STR) and the solvent was dried in a speed vac. The resulting residue was chromatographed using Prep HPLC (conditions: Xterra MS-C18 (30×50 mm); Eluted with 10% to 100% B, 6 min gradient. (A=100% water–0.1% TFA and B=acetonitrile with 0.1% TFA); Flow rate at 30 mL/min. UV detection at 220 nm) to give compound 50 (13.8 mg, 69%). HPLC: 99% at 1.74 min (retention time) (Conditions: Xterra MS-C18 (2.1×50 mm); Eluted with 0% to 100% B, 2.75 min gradient. (A=100% water–0.1% TFA and B=acetonitrile with 0.1% TFA); Flow rate at 1 mL/min. UV detection at 220 nm). MS (ES): m/z 413 [M+H]$^+$.

Example 51-86

Additional compounds were prepared by procedures described in Example 50. The compounds of example 51-86 have the following structure,

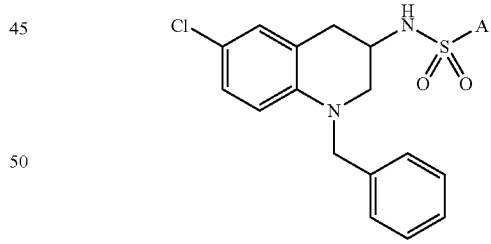

where the group A, the compound name, retention time, molecular mass, and the procedure employed, are set forth in Table 4. The chromatography techniques used to determine the compound retention times of Table 4 are as follows: HPLC (purity) conditions: Xterra MS-C18 (2.1×50 mm); Eluted with 0% to 100% B, 2.75 min gradient (A=100% water–0.1% TFA and B=acetonitrile with 0.1% TFA); Flow rate at 1 mL/min. UV detection at 220 nm). The molecular mass of the compounds listed in Table 4, where provided, were determined by MS (ES) by the formula m/z. using Waters LCT Time of flight mass spec, with a mux 4-way source.

TABLE 4

| Ex. No. | A | Compound Name | Retention Time (min.)/m/z | See Ex. |
|---|---|---|---|---|
| 51 | | N,N-Dimethylamino-1-sulfonic acid (1-benzyl-6-chloro-1,2,3,4-tetrahydroquinolin-3-yl)-amide | 1.63 LCMS/ 380 [M + H]$^+$ | 50 |
| 52 | | N-(1-Benzyl-6-chloro-1,2,3,4-tetrahydroquinolin-3-yl)ethanesulfonamide | 1.54 LCMS/ 365 [M + H]$^+$ | 50 |
| 53 | | N-(1-Benzyl-6-chloro-1,2,3,4-tetrahydroquinolin-3-yl)-2,2,2-trifluoroethanesulfonamide | 1.70 LCMS/ 419 [M + H]$^+$ | 50 |
| 54 | | N-(1-Benzyl-6-chloro-1,2,3,4-tetrahydroquinolin-3-yl)-2-(naphthalen-1-yl)ethanesulfonamide | 1.99 LCMS/ 491 [M + H]$^+$ | 50 |
| 55 | | N-(1-Benzyl-6-chloro-1,2,3,4-tetrahydroquinolin-3-yl)-4-propylbenzenesulfonamide | 2.04 LCMS/ 455 [M + H]$^+$ | 50 |
| 56 | | N-(1-Benzyl-6-chloro-1,2,3,4-tetrahydroquinolin-3-yl)-4-ethylbenzenesulfonamide | 1.97 LCMS/ 441 [M + H]$^+$ | 50 |
| 57 | | N-(1-Benzyl-6-chloro-1,2,3,4-tetrahydroquinolin-3-yl)-4-(2-cyanoethoxy)benzenesulfonamide | 1.67 LCMS/ 482 [M + H]$^+$ | 50 |
| 58 | | N-(1-Benzyl-6-chloro-1,2,3,4-tetrahydroquinolin-3-yl)-4-bromobenzenesulfonamide | 1.94 LCMS/ 492 [M + H]$^+$ | 50 |
| 59 | | N-(1-Benzyl-6-chloro-1,2,3,4-tetrahydroquinolin-3-yl)-2,5-dimethylbenzenesulfonamide | 1.94 LCMS/ 441 [M + H]$^+$ | 50 |
| 60 | | N-(1-Benzyl-6-chloro-1,2,3,4-tetrahydroquinolin-3-yl)-2-(trifluoromethoxy)benzenesulfonamide | 1.91 LCMS/ 497 [M + H]$^+$ | 50 |

TABLE 4-continued

| Ex. No. | A | Compound Name | Retention Time (min.)/m/z | See Ex. |
|---|---|---|---|---|
| 61 | 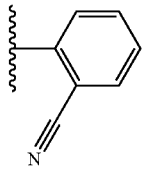 | N-(1-Benzyl-6-chloro-1,2,3,4-tetrahydroquinolin-3-yl)-2-cyanobenzenesulfonamide | 1.72 LCMS/ 438 [M + H]$^+$ | 50 |
| 62 | 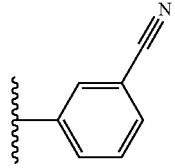 | N-(1-Benzyl-6-chloro-1,2,3,4-tetrahydroquinolin-3-yl)-3-cyanobenzenesulfonamide | 1.69 LCMS/ 438 [M + H]$^+$ | 50 |
| 63 | 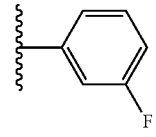 | N-(1-Benzyl-6-chloro-1,2,3,4-tetrahydroquinolin-3-yl)-3-fluorobenzenesulfonamide | 1.79 LCMS/ 431 [M + H]$^+$ | 50 |
| 64 | 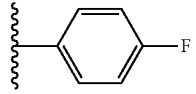 | N-(1-Benzyl-6-chloro-1,2,3,4-tetrahydroquinolin-3-yl)-4-fluorobenzenesulfonamide | 1.77 LCMS/ 431 [M + H]$^+$ | 50 |
| 65 | 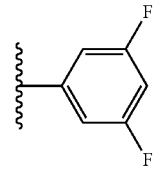 | N-(1-Benzyl-6-chloro-1,2,3,4-tetrahydroquinolin-3-yl)-3,5-difluorobenzenesulfonamide | 1.83 LCMS/ 449 [M + H]$^+$ | 50 |
| 66 | 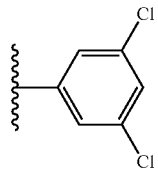 | N-(1-Benzyl-6-chloro-1,2,3,4-tetrahydroquinolin-3-yl)-3,5-dichlorobenzenesulfonamide | 2.06 LCMS/ 483 [M + H]$^+$ | 50 |
| 67 | 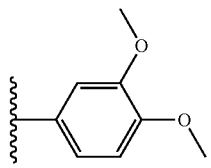 | N-(1-Benzyl-6-chloro-1,2,3,4-tetrahydroquinolin-3-yl)-3,4-dimethoxyl benzenesulfonamide | 1.66 LCMS/ 473 [M + H]$^+$ | 50 |
| 68 | 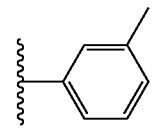 | N-(1-Benzyl-6-chloro-1,2,3,4-tetrahydroquinolin-3-yl)-3-methylbenzenesulfonamide | 1.83 LCMS/ 427 [M + H]$^+$ | 50 |
| 69 | 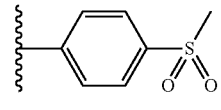 | N-(1-Benzyl-6-chloro-1,2,3,4-tetrahydroquinolin-3-yl)-4-methylsulfonyl) benzenesulfonamide | 1.6 LCMS/ 491 [M + H]$^+$ | 50 |
| 70 | 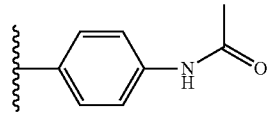 | N-(1-Benzyl-6-chloro-1,2,3,4-tetrahydroquinolin-3-yl)-4-acetamido) benzenesulfonamide | 1.52 LCMS/ 470 [M + H]$^+$ | 50 |

TABLE 4-continued

| Ex. No. | A | Compound Name | Retention Time (min.)/m/z | See Ex. |
|---|---|---|---|---|
| 71 | (4-(pyrrolidine-1-carbonyl)aminophenyl) | N-(1-Benzyl-6-chloro-1,2,3,4-tetrahydroquinolin-3-yl)-4-(pyrrolidine-1-carboxamido)benzenesulfonamide | 1.57 LCMS/ 525 [M + H]$^+$ | 50 |
| 72 | benzo[c][1,2,5]thiadiazol-4-yl | N-(1-Benzyl-6-chloro-1,2,3,4-tetrahydroquinolin-3-yl)benzo(c)[1,2,5]thiazole-4-sulfonamide | 1.76 LCMS/ 471 [M + H]$^+$ | 50 |
| 73 | 3-(5-methyl-1,3,4-oxadiazol-2-yl)phenyl | N-(1-Benzyl-6-chloro-1,2,3,4-tetrahydroquinolin-3-yl)-3-(5-methyl-1,3,4-oxadizol-2-yl)benzene sulfonamide | 1.62 LCMS/ 495 [M + H]$^+$ | 50 |
| 74 | 5-bromothiophen-2-yl | N-(1-Benzyl-6-chloro-1,2,3,4-tetrahydroquinolin-3-yl)-5-bromothiophene-2-sulfonamide | 1.92 LCMS/ 499 [M + H]$^+$ | 50 |
| 75 | 4,5-dibromothiophen-2-yl | N-(1-Benzyl-6-chloro-1,2,3,4-tetrahydroquinolin-3-yl)-4,5-dibromothiophene-2-sulfonamide | 2.06 LCMS/ 576 [M + H]$^+$ | 50 |
| 76 | 4,5-dichlorothiophen-2-yl | N-(1-Benzyl-6-chloro-1,2,3,4-tetrahydroquinolin-3-yl)-4,5-dichlorothiophene-2-sulfonamide | 2.05 LCMS/ 488 [M + H]$^+$ | 50 |
| 77 | 1-methyl-1H-imidazol-4-yl | N-(1-Benzyl-6-chloro-1,2,3,4-tetrahydroquinolin-3-yl)-1-methyl-1H-imidazole-4-sulfonamide | 1.4 LCMS/ 417 [M + H]$^+$ | 50 |
| 78 | 1,2-dimethyl-1H-imidazol-4-yl | N-(1-Benzyl-6-chloro-1,2,3,4-tetrahydroquinolin-3-yl)-1,2-dimethyl-1H-imidazole-4-sulfonamide | 1.44 LCMS/ 431 [M + H]$^+$ | 50 |
| 79 | 5-chloro-1,3-dimethyl-1H-pyrazol-4-yl | N-(1-Benzyl-6-chloro-1,2,3,4-tetrahydroquinolin-3-yl)-5-chloro-1,3-dimethyl-1H-pyrazole-4-sulfonamide | 1.67 LCMS/ 465 [M + H]$^+$ | 50 |
| 80 | 3,5-dimethylisoxazol-4-yl | N-(1-Benzyl-6-chloro-1,2,3,4-tetrahydroquinolin-3-yl)-3,5-dimethylisoxazole-4-sulfonamide | 1.74 LCMS/ 432 [M + H]$^+$ | 50 |

TABLE 4-continued

| Ex. No. | A | Compound Name | Retention Time (min.)/m/z | See Ex. |
|---|---|---|---|---|
| 81 | 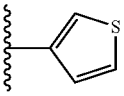 | N-(1-Benzyl-6-chloro-1,2,3,4-tetrahydroquinolin-3-yl)-thiophene-3-sulfonamide | 1.71 LCMS/ 419 [M + H]$^+$ | 50 |
| 82 | 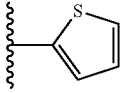 | N-(1-Benzyl-6-chloro-1,2,3,4-tetrahydroquinolin-3-yl)-thiophene-2-sulfonamide | 1.72 LCMS/ 419 [M + H]$^+$ | 50 |
| 83 | 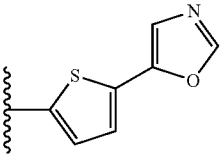 | N-(1-Benzyl-6-chloro-1,2,3,4-tetrahydroquinolin-3-yl)-5-(oxazol-5-yl)thiophene-2-sulfonamide | 1.69 LCMS/ 486 [M + H]$^+$ | 50 |
| 84 | 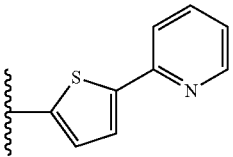 | N-(1-Benzyl-6-chloro-1,2,3,4-tetrahydroquinolin-3-yl)-5-(pyridin-2-yl)thiophene-2-sulfonamide | 1.85 LCMS/ 496 [M + H]$^+$ | 50 |
| 85 | 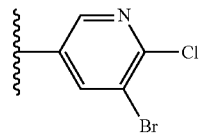 | N-(1-Benzyl-6-chloro-1,2,3,4-tetrahydroquinolin-3-yl)-5-bromo-6-chloro pyridine-3-sulfonamide | 1.92 LCMS/ 527 [M + H]$^+$ | 50 |
| 86 | 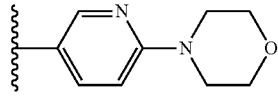 | N-(1-Benzyl-6-chloro-1,2,3,4-tetrahydroquinolin-3-yl)-6-morpholino chloro pyridine-3-sulfonamide | 1.67 LCMS/ 499 [M + H]$^+$ | 50 |

Example 87
(S)—N-(1-Benzyl-6-bromo-1,2,3,4-tetrahydroquinolin-3-yl)-benzenesulfonamide

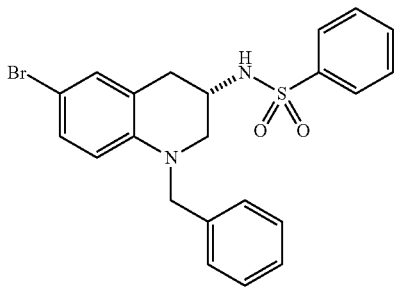

87A. N-(6-Bromo-1,2,3,4-tetrahydroquinolin-3-yl)-benzenesulfonamide

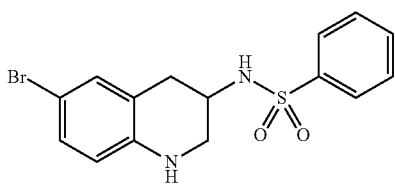

Compound 1A was treated with 4N HCl in dioxane, and the resulting product was reacted with benzene sulfonylchloride following the procedures described in Example 1D and 1G to give compound 87A.

87B. N-(1-benzyl-6-bromo-1,2,3,4-tetrahydroquinolin-3-yl)-benzene-sulfonamide

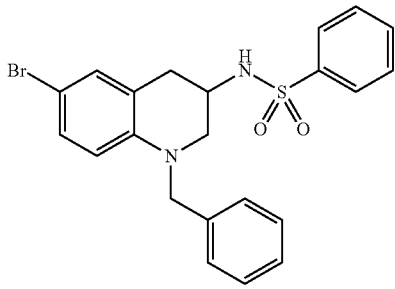

The title compound was prepared from 87A and benzaldehyde by procedures analogous to those described in Example 22A.

87C. (S)—N-(1-Benzyl-6-bromo-1,2,3,4-tetrahydroquinolin-3-yl)-benzene-sulfonamide The title compound was obtained via chiral chromatographic separation of racemic 87B using a Chiralpak AD column (5×50 cm, 20 μm chiral stationary phase) eluting with 30% isopropanol in heptane. HPLC: 99% at 8.01 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm).

MS (ES): m/z 458 [M+1]$^+$. Chiral HPLC 100% e.e.; retention time=17.97 min; Conditions: AD (4.6×250 mm); Eluted with 30% isopropanol in heptane for 30 min at 1 mL/min.

Alternatively, homochiral 87C can also be prepared from (S)-2-(tert-butyloxy carbonylamino)-3-(2-nitrophenyl)propanoic acid as described below starting from 87D.

87D. (S)-(2-Oxo-1,2,3,4-tetrahydroquinolin-3-yl)-carbamic acid tert-butyl ester

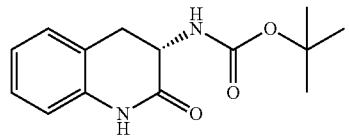

The title compound may be prepared either as described in US 2004/002495 or as follows: To a solution of (S)-2-(tert-butyloxycarbonylamino)-3-(2-nitrophenyl) propanoic acid (987 mg, 3.18 mmol) in MeOH (100 mL) was added 10% palladium on carbon (300 mg), and the mixture was stirred at RT under hydrogen at 80 psi for 24 h. Filtration and solvent evaporation under vacuum provided the title compound (800 mg) as a foam.

87E. (S)-(6-Bromo-2-oxo-1,2,3,4-tetrahydroquinolin-3-yl)-carbamic acid tert-butyl ester

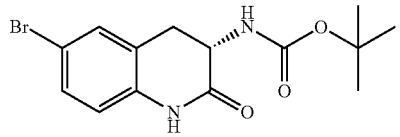

To a solution of 87D (750 mg, 2.42 mmol) in MeOH (12 mL) and $CH_2Cl_2$ (12 mL) stirring at RT under argon was added $CaCO_3$ (484 mg, 4.83 mmol) and benzyltrimethylammonium tribromide (1.885 g, 4.83 mmol). After 18 h, 10% aqueous $NaHSO_3$ (5 mL) was added to the reaction mixture, and stirring was continued for 30 min. Partial evaporation under vacuum was performed to remove nearly all of the organic solvents before the mixture was extracted twice with $CH_2Cl_2$. The combined extracts were washed with water, dried ($MgSO_4$), and evaporated under vacuum. The resulting residue was chromatographed on silica gel eluted with 25% $Et_2O$ in $CH_2Cl_2$ to obtain the title compound (746 mg) as a white foam.

87F. (S)-(1-Benzyl-6-bromo-2-oxo-1,2,3,4-tetrahydroquinolin-3-yl)-carbamic acid tert-butyl ester

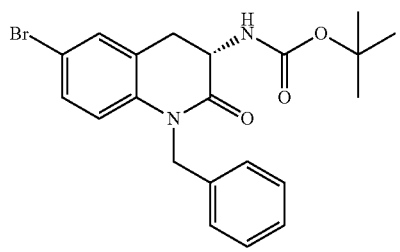

A stirring mixture of 87E (0.60 g, 1.76 mmol), $K_2CO_3$ (0.49 g, 3.52 mmol), and benzyl bromide (0.36 g, 2.11 mmol) in acetone (15 mL) was heated to reflux under argon for 16 h.

The mixture was then cooled to RT and the solvent was evaporated under vacuum. The resulting residue was partitioned between water and EtOAc. The EtOAc layer was washed with brine, dried (Na$_2$SO$_4$), and evaporated. The resulting crude product was chromatographed on silica gel eluted with 10-20% EtOAc in hexane (step-wise gradient) to obtain the title compound (0.72 g) as a solid.

87G. (S)-3-Amino-1-benzyl-6-bromo-2-oxo-1,2,3,4-tetrahydroquinoline, hydrochloric acid salt

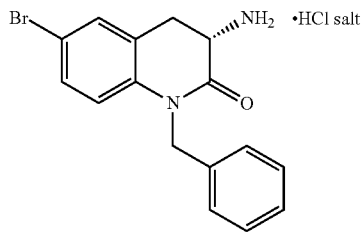

The title compound was prepared from 87F according to the procedures described in Example 1D.

87H. (S)—N-(1-Benzyl-6-bromo-2-oxo-1,2,3,4-tetrahydroquinolin-3-yl)-benzenesulfonamide

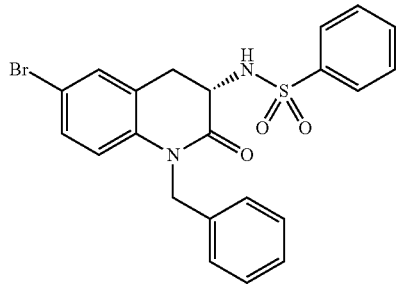

The title compound was prepared from 87G according to the procedures described in Example 1G.

87C. (S)—N-(1-Benzyl-6-bromo-1,2,3,4-tetrahydro-quinolin-3-yl)-benzene-sulfonamide The title compound was prepared from 87H according to the procedures described in Example 148I.

Example 88

(R)—N-(1-Benzyl-6-bromo-1,2,3,4-tetrahydroquinolin-3-yl)-benzenesulfonamide

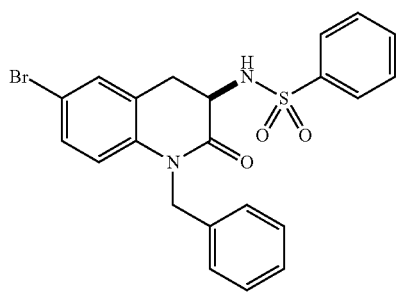

The title compound was obtained via chiral chromatographic separation of racemic 87B using a Chiralpak AD column (5×50 cm, 20 μm chiral stationary phase) eluting with 30% isopropanol in heptane.

Alternatively, the title compound can be prepared from commercially available (R)-2-(tert-butyloxycarbonylamino)-3-(2-nitrophenyl)propanoic acid according to the procedures described in Example 87. HPLC: 99% at 8.01 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 458 [M+1]$^+$. Chiral HPLC 100% e.e.; retention time=11.50 min; Conditions: AD (4.6×250 mm); Eluted with 30% isopropanol in heptane for 30 min at 1 mL/min.

Example 89

(S)N-(1-Benzyl-6-phenyl-1,2,3,4-tetrahydroquinolin-3-yl)-benzenesulfonamide

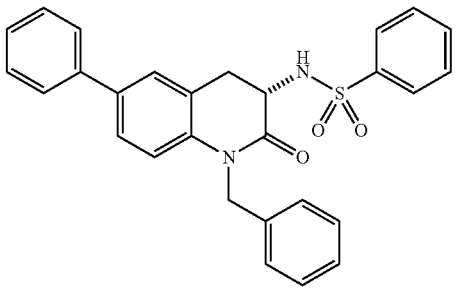

89A. (1-Benzyl-6-bromo-1,2,3,4-tetrahydroquinolin-3-yl)-carbamic acid tert-butyl ester

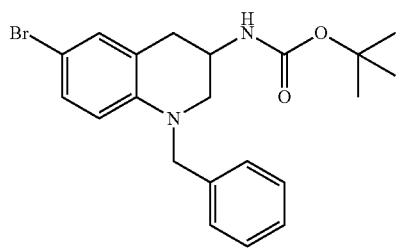

To a solution of 1B (1.636 g, 5 mmol) in DCE (16 mL) at RT was added benzaldehyde (1 mL, 10 mmol), followed by NaB(OAc)$_3$H (2.97 g, 14 mmol) and AcOH (0.6 mL, 10 mmol). The reaction mixture was stirred at RT for 16 h, then quenched with aqueous NaHCO$_3$ (40 mL) and extracted with CH$_2$Cl$_2$ (50 mL×3). The combined extracts were washed with brine, dried (Na$_2$SO$_4$), and concentrated. The resulting residue was chromatographed (silica gel) eluting with 0-20% of EtOAc in hexane to give the title compound (1.70 g, 81%) as a white foam.

89B. (1-Benzyl-6-phenyl-1,2,3,4-tetrahydroquinolin-3-yl)-carbamic acid tert-butyl ester

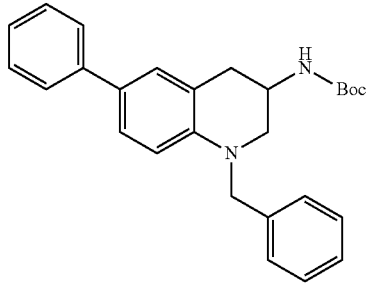

Compound 89A (150 mg, 0.36 mmol), phenylboronic acid (57 mg, 0.47 mmol) and 2N aqueous $Na_2CO_3$ (1.25 mL, 2.5 mmol) in a mixed solvent of toluene (1.5 mL) and EtOH (0.5 mL) were stirred at RT for 30 min while $N_2$ was allowed to bubble through the mixture, and then tetrakis(triphenylphosphine)-palladium (0) (30 mg) was added. The mixture was stirred at 90° C. under $N_2$ for 1 h. After cooling to RT, the mixture was extracted with EtOAc (15 mL×3), and organic extracts were washed with brine, dried ($Na_2SO_4$), and concentrated. The resulting residue was chromatographed (silica gel) eluting with EtOAc (10-50%) in hexane to give the title compound (80 mg, 67%) as a white foam.

89C. 1-Benzyl-6-phenyl-1,2,3,4-tetrahydroquinolin-3-ylamine, trifluoroacetic acid salt

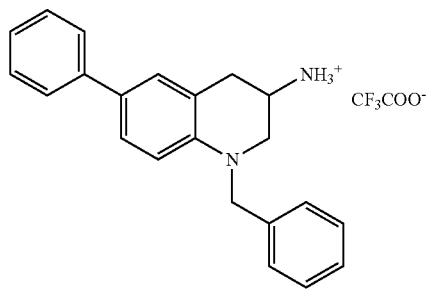

To a solution of compound 89B (44 mg, 0.106 mmol) in $CH_2Cl_2$ (0.5 mL) at RT was added trifluoroacetic acid (0.5 mL). After stirring at RT for 1.5 h, the reaction mixture was concentrated, and the resulting residue stripped with toluene, dried in vacuo to give the title compound as an oil (46 mg, 100%).

89D. N-(1-Benzyl-6-phenyl-1,2,3,4-tetrahydroquinolin-3-yl)-benzene-sulfonamide

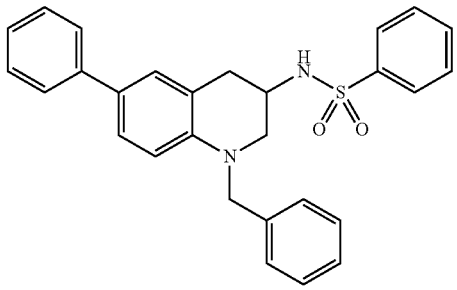

Compound 89D was prepared from 89C by procedures analogous to those described in Example 1G. HPLC: 96% at 8.3 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 455 $[M+1]^+$.

89E. (S)N-(1-Benzyl-6-phenyl-1,2,3,4-tetrahydroquinolin-3-yl)-benzene-sulfonamide The title compound was obtained via chiral chromatographic separation of racemic 89D using a Chiralpak AD column (5×50 cm, 20 μm chiral stationary phase) eluting with 20% isopropanol in heptane.

The title compound was also prepared using the following procedures: To a solution of 87C (510 mg, 1.11 mmol) in THF/MeOH (2:1, 15 mL) was added phenylboronic acid (272 mg, 2.22 mmol), followed by $K_2CO_3$ (613 mg, 4.44 mmol) and PXPd (30 mg, 0.056 mmol). The reaction mixture was stirred at 60° C. for 2 h, then additional amount of phenylboronic acid (54 mg, 0.44 mmol) and PXPd (16 mg, 0.028 mmol) were added. After 2 h at 60° C., same amount of phenylboronic acid and PXPd were added again to the reaction mixture to push completion of the reaction. After stirring at 60° C. for one more hour, the reaction was allowed to cool to RT and concentrated. The residue was partitioned between water and $CH_2Cl_2$, and the aqueous phase extracted with $CH_2Cl_2$ (50 mL×2). The combined organics were washed with brine, dried ($Na_2SO_4$) and concentrated. The residue was purified using chromatography (silica gel) eluting with EtOAc/hexane (0-60%) to afford the title compound (260 mg, 51%) as a white solid.

HPLC: 99% at 8.35 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 455 $[M+1]^+$.

Chiral HPLC: 100% e.e.; retention time=17.20 min; Conditions: AD (4.6×250 mm); Eluted with 30% isopropanol in heptane for 30 min at 1 mL/min.

Example 90

(R)N-(1-Benzyl-6-phenyl-1,2,3,4-tetrahydroquinolin-3-O-benzenesulfonamide

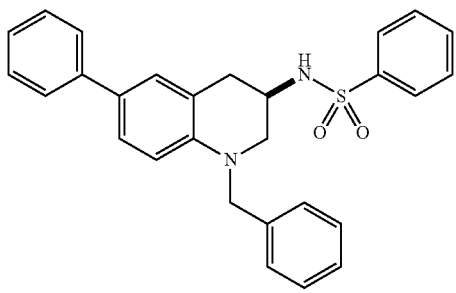

The title compound was obtained via chiral chromatographic separation of racemic 89D using a Chiralpad AD column (5×50 cm, 20 μm chiral stationary phase) eluting with 20% isopropanol in heptane.

The title compound was also prepared from 88 using the procedures analogous to those described in Example 89E.

HPLC: 99% at 8.35 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 455 [M+1]$^+$. Chiral HPLC: 100% e.e.; retention time=14.85 min; Conditions: AD (4.6×250 mm); Eluted with 30% isopropanol in heptane for 30 min at 1 mL/min.

Example 91

(R)—N-(1-Benzyl-6-(4-fluorophenyl)-1,2,3,4-tetrahydroquinolin-3-yl)benzenesulfonamide

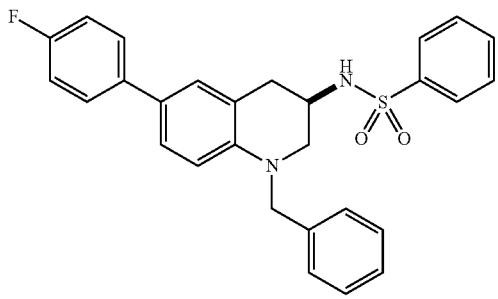

91A. N-(1-Benzyl-6-(4-fluorophenyl)-1,2,3,4-tetrahydroquinolin-3-yl)benzenesulfonamide

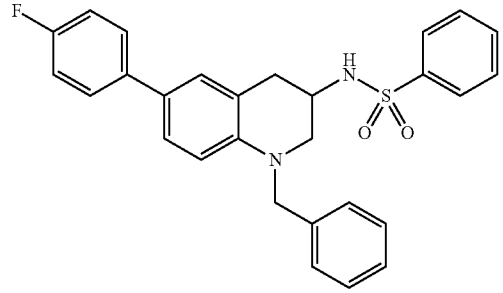

To a solution of 87B (3.648 g, 8.0 mmol) and 4-fluorobenzene boronic acid (2.24 g, 16.0 mmol) in a mixed solvent of MeOH-THF (80 mL, 1:1 ratio) was added K$_2$CO$_3$ (4.423 g, 32.0 mmol), followed by PXPd (215 mg, 0.40 mmol). The resulting suspension was vigorously stirred in a 70° oil bath for 35 min. After cooling down to RT, the dark brown solution was diluted with water (200 mL), and extracted with EtOAc (200 mL×2). The combined EtOAc extracts were washed with brine, dried (Na$_2$SO$_4$) and concentrated. The residue was chromatographed (silica gel) eluting with EtOAc/hexane (0-30%) to afford the title compound (2.977 g, 79%) as a light brown solid.

91B. (R)—N-(1-Benzyl-6-(4-fluorophenyl)-1,2,3,4-tetrahydroquinolin-3-yl)benzenesulfonamide The title compound was obtained via chiral chromatographic separation of racemic 91A using a Chiralpad AD column (5×50 cm, 20 μm chiral stationary phase) eluting with a mixed solvent (isopropanol-methanol-heptane=1:1:2)

The title compound can also be prepared from homochiral 88 using the procedures described in Example 89E. HPLC: 99% at 8.46 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 473 [M+1]$^+$. Chiral HPLC: 99% e.e.; retention time=10.02 min; Conditions: AD (4.6×250 mm); Eluted with 30% isopropanol in heptane for 30 min at 1 mL/min.

Example 92

(S) N-(1-Benzyl-6-(4-fluorophenyl)-1,2,3,4-tetrahydroquinolin-3-yl)-benzenesulfonamide

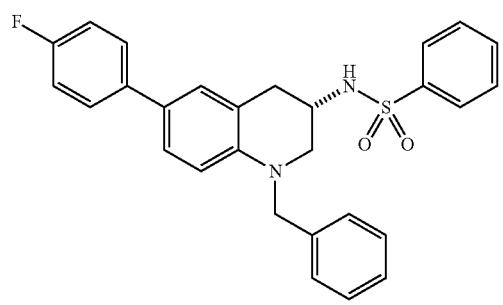

The title compound was obtained via chiral chromatographic separation of racemic 91A using a Chiralpad AD column (5×50 cm, 20 μm chiral stationary phase) eluting with a mixed solvent (isopropanol-methanol-heptane=1:1:2).

Alternatively, the title compound can be prepared from homochiral 87C using the procedures described in Example 89E. HPLC: 99% at 8.34 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 473 [M+1]$^+$. Chiral HPLC: 99% e.e.; retention time=17.84 min; Conditions: AD (4.6×250 mm); Eluted with 30% isopropanol in heptane for 30 min at 1 mL/min.

Example 93

N-(1-Benzyl-6-(2-oxopyridin-1(2H)-yl)-1,2,3,4-tetrahydroquinolin-3-yl)benzenesulfonamide

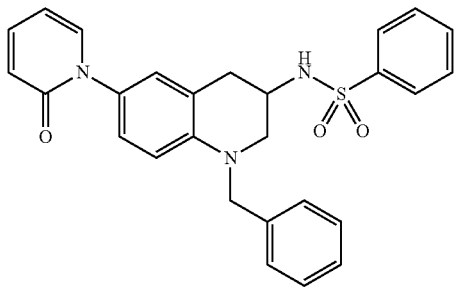

To a suspension of 87B (229 mg, 0.5 mmol), 2-hydroxypyridine (71.3 mg, 0.75 mmol), $K_2CO_3$ (138.2 mg, 1.0 mmol) and copper iodide (47.6 mg, 0.25 mmol) in DMF (i.o mL) was added N,N'-dimethylethylenediamine (27 μL, 025 mmol). The resulting blue suspension was shaken at 110° for 2 h. After cooling to RT, the reaction mixture was partitioned between EtOAc and water, and the aqueous layer was extracted with EtOAc (3×). The combined EtOAc extracts were washed with brine, dried ($Na_2SO_4$) and concentrated. The residue was chromatographed (silica gel) eluting with EtOAc/hexane (30-60%) to afford 93 (45 mg, 19%) as an off-white solid. HPLC: 99% at 6.72 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 472 [M+1]$^+$.

Example 94 to 108

Additional compounds were prepared by procedures analogous to those described in Example 89 and 93. The compounds of Examples 94 to 108 have the following structure,

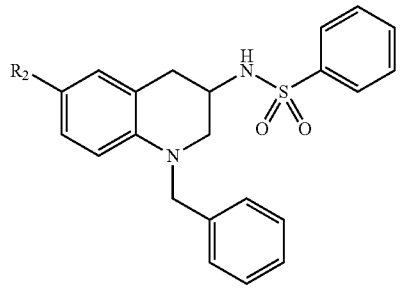

where the group $R_2$, the stereochemistry, the compound name, retention time, molecular mass, and the procedure employed, are set forth in Table 5. The chromatography techniques used to determine the compound retention times of Table 5 are as follows: HPLC (purity) conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm) (Note: retention time*=4 min gradient). LC-MS conditions: Phenom. Luna C18 (4.6×50 mm eluting with 10-90% MeOH/$H_2O$ over 4 minutes containing 0.1% TFA; 4 mL/min, monitoring at 220 nm. The molecular mass of the compounds listed in Table 5, where provided, were determined by MS (ES) by the formula m/z.

TABLE 5

| Ex. No. | $R_2$ | Compound Name | Retention Time (min.)/m/z | See Ex. |
|---|---|---|---|---|
| 94 | | N-(1-Benzyl-6-pyridin-2-yl-1,2,3,4-tetrahydroquinolin-3-yl)-benzenesulfonamide | 5.37 LCMS/ 456 [M + H]$^+$ | 89B |
| 95 | | N-(1-Benzyl-6-pyridin-3-yl-1,2,3,4-tetrahydroquinolin-3-yl)-benzenesulfonamide | 5.66 LCMS/ 456 [M + H]$^+$ | 89E |
| 96 | | N-(1-Benzyl-6-pyridin-4-yl-1,2,3,4-tetrahydroquinolin-3-yl)-benzenesulfonamide | 5.50 LCMS/ 456 [M + H]$^+$ | 89E |
| 97 | | N-[1-Benzyl-6-(3-fluorophenyl)-1,2,3,4-tetrahydroquinolin-3-yl]-benzenesulfonamide | 8.37 LCMS/ 473 [M + H]$^+$ | 89E |

TABLE 5-continued

| Ex. No. | R₂ | Compound Name | Retention Time (min.)/m/z | See Ex. |
|---|---|---|---|---|
| 98 | thiophen-2-yl | N-(1-Benzyl-6-thiophen-2-yl-1,2,3,4-tetrahydroquinolin-3-yl)-benzenesulfonamide | 8.26 LCMS/ 461 [M + H]⁺ | 89B |
| 99 | thiophen-3-yl | N-(1-Benzyl-6-thiophen-3-yl-1,2,3,4-tetrahydroquinolin-3-yl)-benzenesulfonamide | 8.18 LCMS/ 461 [M + H]⁺ | 89E |
| 100 | vinyl (=CH₂) | N-(1-Benzyl-6-vinyl-1,2,3,4-tetrahydroquinolin-3-yl)-benzenesulfonamide | 7.94 LCMS/ 405 [M + H]⁺ | 89B |
| 101 | allyl (-CH₂-CH=CH₂) | N-(6-Allyl-1-benzyl-1,2,3,4-tetrahydroquinolin-3-yl)-benzenesulfonamide | 8.28 LCMS/ 419 [M + H]⁺ | 89B |
| 102 | 4-(trifluoromethoxy)phenyl | N-(1-Benzyl-6-(4-(trifluoromethoxy)phenyl)-1,2,3,4-tetrahydroquinolin-3-yl)benzenesulfonamide | 4.32* LCMS/ 539 [M + H]⁺ | 89E |
| 103 | 6-methoxypyridin-3-yl | N-(1-Benzyl-6-(6-methoxypyridin-3-yl)-1,2,3,4-tetrahydroquinolin-3-yl)benzenesulfonamide | 3.90* LCMS/ 486 [M + H]⁺ | 89E |
| 104 | 4-(benzyloxy)-3-fluorophenyl | N-(1-Benzyl-6-(4-(benzyloxy)-3-fluorophenyl)-1,2,3,4-tetrahydroquinolin-3-yl)benzenesulfonamide | 4.39* LCMS/ 579 [M + H]⁺ | 89E |
| 105 | 2-oxopyrrolidin-1-yl | N-(1-Benzyl-6-(2-oxopyrrolidin-1-yl)-1,2,3,4-tetrahydroquinolin-3-yl)benzenesulfonamide | 6.85 LCMS/ 462 [M + H]⁺ | 93 |
| 106 | 2-oxopiperidin-1-yl | N-(1-Benzyl-6-(2-oxopiperidin-1-yl)-1,2,3,4-tetrahydroquinolin-3-yl)benzenesulfonamide | 6.98 LCMS/ 476 [M + H]⁺ | 93 |
| 107 | 1H-imidazol-1-yl | N-(1-Benzyl-6-(1H-imidazol-1-yl)-1,2,3,4-tetrahydroquinolin-3-yl)benzenesulfonamide | 5.21 LCMS/ 445 [M + H]⁺ | 93 |
| 108 | 1H-pyrazol-1-yl | N-(1-Benzyl-6-(1H-pyrazol-1-yl)-1,2,3,4-tetrahydroquinolin-3-yl)benzenesulfonamide | 7.18 LCMS/ 445 [M + H]⁺ | 93 |

Example 109

N-(1-Benzyl-6-(3-fluoro-4-hydroxyphenyl)-1,2,3,4-tetrahydroquinolin-3-yl)benzenesulfonamide

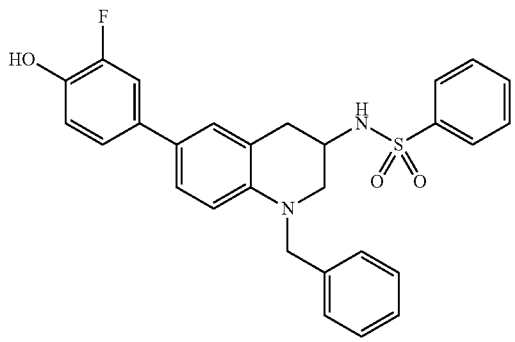

To a 2-neck round-bottom flask was added 104 (12 mg, 0.0207 mmol), EtOAc (2 ml), ethanol (2 ml), 5% Pd/C (5 mg). The resulting suspension was stirred under hydrogen balloon for 5 hours. The reaction mixture was filtered through a pad of Celite, and the filtrate concentrated in vacuo. The resulting residue was purified using prep HPLC (Conditions: Phenomenex Luna 5μ C18 21.2×100 mm); Eluted with 0% to 100% B, 10 min gradient (A=90% H$_2$O–10% MeOH and B=10% H$_2$O–90% MeOH); Flow rate at 20 mL/min, UV detection at 220 nm) to give the title compound (6 mg, 60%) as an off-white solid. HPLC: 99% at 3.777 min (retention time) (Conditions: YMC S5 ODS CombiScreen 4.6×50 mm); Eluted with 0% to 100% B, 4 min gradient (A=90% H$_2$O–10% MeOH–0.1% H$_3$PO$_4$ and B=10% H$_2$O–90% MeOH–0.1% H$_3$PO$_4$); Flow rate at 4 mL/min, UV detection at 220 nm). MS (ES): m/z=489 [M+1]$^+$.

Example 110

N-(1-Benzyl-6-(6-hydroxypyridin-3-yl)-1,2,3,4-tetrahydroquinolin-3-yl)benzenesulfonamide

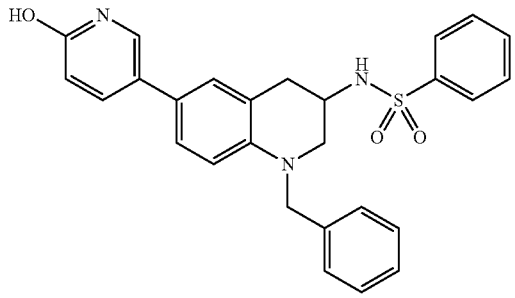

To a round-bottom flask was added 103 (10 mg, 0.0206 mmol), acetic acid (1 ml) and 40% HBr in H$_2$O. The reaction mixture was stirred at 90° C. for 10 hours. After cooling to RT, the reaction mixture was treated with 1N aqueous NaOH (10 ml), then extracted with EtOAc (2×10 ml). The combined organics were washed with water (5 ml), brine (10 ml), dried (MgSO4) and concentrated. The residue was purified using prep HPLC (Conditions: Phenomenex Luna 5μ C18 21.2×100 mm); Eluted with 0% to 100% B, 10 min gradient (A=90% H$_2$O–10% MeOH and B=10% H$_2$O–90% MeOH); Flow rate at 20 mL/min, UV detection at 220 nm) to give the title compound (4 mg, 42%) as a white solid. HPLC: 99% at 3.410 min (retention time) (Conditions: YMC S5 ODS CombiScreen 4.6×50 mm); Eluted with 0% to 100% B, 4 min gradient (A=90% H$_2$O–10% MeOH–0.1% H$_3$PO$_4$ and B=10% H$_2$O–90% MeOH–0.1% H$_3$PO$_4$); Flow rate at 4 mL/min, UV detection at 220 nm). MS (ES): m/z=472 [M+1]$^+$.

Example 111

(R)—N-(1-Benzyl-6-(4-fluorophenyl)-1,2,3,4-tetrahydroquinolin-3-yl)-3-hydroxybenzenesulfonamide

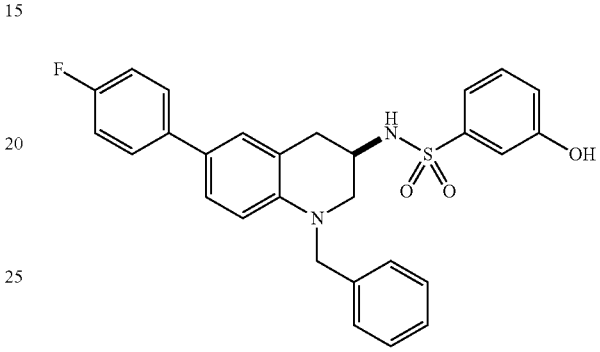

111A. 1-Benzyl-6-(4-fluorophenyl)-1,2,3,4-tetrahydroquinolin-3-amine, trifluoroacetic acid salt

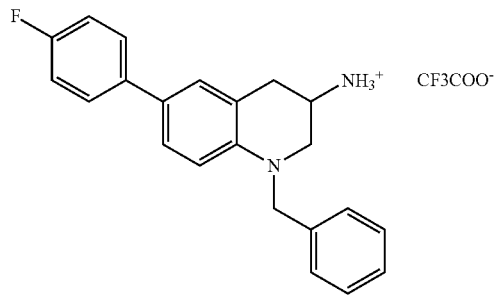

Compound 111A was prepared from 89A and 4-fluorophenylboronic acid, then N-boc deprotection by procedures analogous to those described in 89B and 89C.

111B. N-(1-Benzyl-6-(4-fluorophenyl)-1,2,3,4-tetrahydroquinolin-3-yl)-3-methoxybenzenesulfonamide

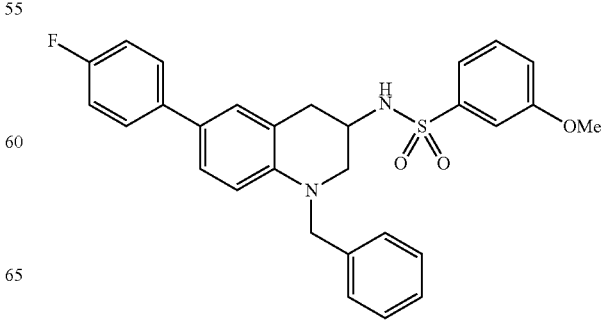

Compound 111B was prepared from 111A and 3-methoxyphenylsulfonyl chloride by procedures analogous to those described in 1G.

111C. (R)—N-(1-Benzyl-6-(4-fluorophenyl)-1,2,3,4-tetrahydroquinolin-3-yl)-3-hydroxybenzenesulfonamide To a solution of 111B (3.9 g, 7.8 mmol) in $CH_2Cl_2$ (100 mL) at −78° C. was added $BBr_3$ (1.47 mL, 15.5 mmol). The reaction solution was stirred at −78° C. for 15 min and at 0° C. for 2 h. The reaction was quenched with methanol (100 mL) and the solvents were removed in vacuo. The residue was redissolved in methanol (100 mL) and glacial acetic acid (1 mL). The mixture was heated to reflux for 1 h and the solvents were removed in vacuo. The residue was chromatographed (silica gel) eluting with EtOAc/hexanes (0-100%) over 20 min. The fractions containing product were combined and evaporated to give 2.5 g of product as a yellow solid. Chiral separation of 0.7 g of product was performed using Chiracel AD column 5×50 cm, flow rate: 40 mL/min; UV detection at 256 nm; solvent: 50% heptane, 25% methanol, 25% isopropanol to afford (R)-isomer (240 mg beige solid) and (S)-isomer (235 mg light yellow solid). HPLC: 4.06 min, column: 4 6×50 mm Phenomenex LUNA C-18 (S-5); flow rate 2.5 mL/min; gradient: 0-100% B over 4 min, hold 100% B for 1 min. Solvent A: (90% $H_2O$–10% MeOH–0.1% $H_3PO_4$ and Solvent B (10% $H_2O$–90% MeOH–0.1% $H_3PO_4$); MS (ES): m/z=489 $[M+1]^+$.

Example 112

(R)—N-(1-Benzyl-6-(4-fluorophenyl)-1,2,3,4-tetrahydroquinolin-3-yl)-3-(dihydrogen phosphate)benzenesulfonamide

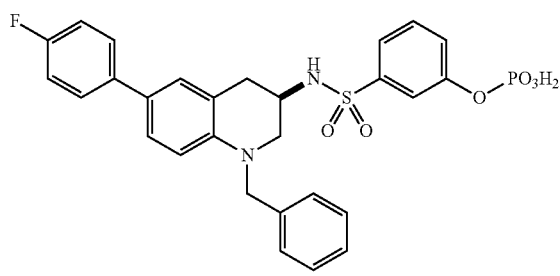

To a solution of 111C (0.1 g, 0.22 mmol) in acetonitrile (2.2 mL) at −10° C. was added carbon tetrachloride (0.1 mL, 1.1 mmol), diisopropylethylamine (0.08 mL, 0.46 mmol), and 4-N,N-dimethylaminopyridine (3 mg, 0.02 mmol). Dibenzyl phosphite (0.085 g, 0.32 mmol) was added dropwise to the reaction solution, and the temperature was maintained at −10° C. for 45 min. The reaction was quenched with 1 mL of 0.5 M aqueous $KH_2PO_4$ and the mixture was stirred at RT. The mixture was diluted with EtOAc (10 mL) and the layers were separated. The organic layer was washed with water (10 mL), brine (10 mL), dried ($MgSO_4$), filtered, and concentrated in vacuo. The residue was purified via flash chromatography (silica gel) eluting with 0-60% ethyl acetate/hexanes to give 67 mg of a yellow oil. The yellow oil (67 mg, 0.1 mmol) was stirred in $CH_2Cl_2$ (0.5 mL) and trifluoroacetic acid (0.5 mL) for 2 h and the solvents were evaporated in vacuo. The residue was purified via preparative reverse-phase HPLC (column: 21×100 mm Phenomenex LUNA C-18 (S-5); flow rate 20 mL/min; gradient: 40-100% B over 12 min, hold 100% B for 8 min. Solvent A: 10% methanol/water+0.1% TFA. Solvent B: 90% methanol/water+0.1% TFA) to give the title compound (56 mg) as a grey solid. HPLC: 4.77 min, column: 4.6×50 mm Phenomenex LUNA C-18 (S-5); flow rate 2.5 mL/min; gradient: 0-100% B over 4 min, hold 100% B for 1 min. Solvent A: 10% methanol/water+0.2% $H_3PO_4$. Solvent B: 90% methanol/water+0.2% $H_3PO_4$. MS (ES): m/z=568 $[M+1]^+$.

Example 113

N-(1-(3-Cyanobenzyl)-6-(4-fluorophenyl)-1,2,3,4-tetrahydroquinolin-3-ylbenzenesulfonamide

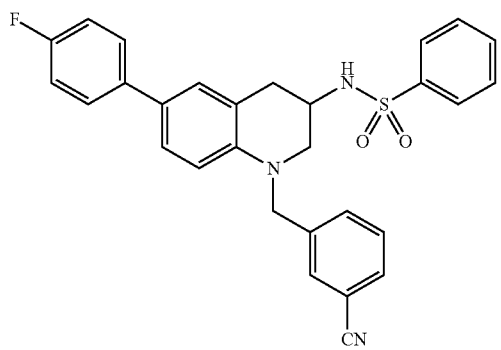

113A. N-(6-(4-Fluorophenyl)-1,2,3,4-tetrahydroquinolin-3-yl)benzene sulfonamide

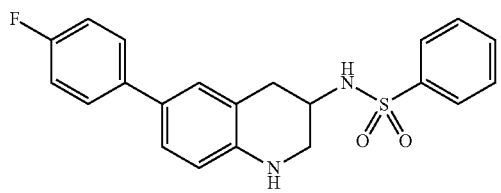

Compound 113A was prepared from 87A and 4-fluorophenylboronic acid by procedures analogous to those described in 89E.

113B. N-(1-(3-Cyanobenzyl)-6-(4-fluorophenyl)-1,2,3,4-tetrahydroquinolin-3-yl)benzenesulfonamide Compound 113B was prepared from 113A and 3-cyanobenzaldehyde by procedures analogous to those described in 22A. HPLC: 96% at 6.25 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 498 $[M+1]^+$.

Example 114-141

Additional compounds were prepared by procedures analogous to those described in Example 113. The compounds of Examples 114 to 141 have the following structure,

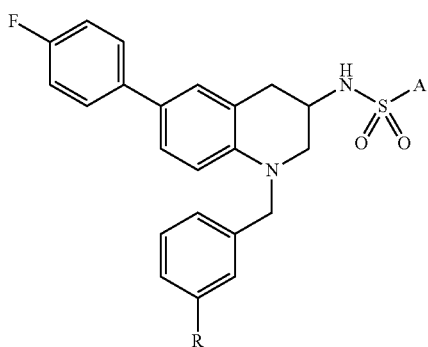

where the group A and group R, the compound name, retention time, molecular mass, and the procedure employed, are set forth in Table 6. The chromatography techniques used to determine the compound retention times of Table 6 are as follows: HPLC (purity) conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). (Note: retention time*=4 min gradient). LC-MS conditions: Phenom. Luna C18, 4.6×50 mm eluting with 10-90% MeOH/$H_2O$ over 4 minutes containing 0.1% TFA; 4 mL/min, monitoring at 220 nm. The molecular mass of the compounds listed in Table 6, where provided, were determined by MS (ES) by the formula m/z.

TABLE 6

| Ex. No. | R | A | Compound Name | Retention Time (min.)/m/z | See Ex. |
|---|---|---|---|---|---|
| 114 | H | | N-(1-Benzyl-6-(4-fluorophenyl)-1,2,3,4-tetrahydroquinolin-3-yl)-2-acetamido-4-methyl thiazole-5-sulfonamide | 3.33* LCMS/ 551 [M + H]⁺ | 111B |
| 115 | H | | N-(1-Benzyl-6-(4-fluorophenyl)-1,2,3,4-tetrahydroquinolin-3-yl)-3,5-dimethylisoxazole-4-sulfonamide | 3.69* LCMS/ 492 [M + H]⁺ | 111B |
| 116 | H | | N-(1-Benzyl-6-(4-fluorophenyl)-1,2,3,4-tetrahydroquinolin-3-yl)-1-methyl-1H-imidazole-4-sulfonamide | 3.32* LCMS/ 477 [M + H]⁺ | 111B |
| 117 | H | | N-(1-Benzyl-6-(4-fluorophenyl)-1,2,3,4-tetrahydroquinolin-3-yl)-5-chloro-1,2-dimethyl-1H-imidazole-4-sulfonamide | 3.64* LCMS/ 525 [M + H]⁺ | 111B |
| 118 | H | | N-(1-Benzyl-6-(4-fluorophenyl)-1,2,3,4-tetrahydroquinolin-3-yl)-1,2-dimethyl-1H-imidazole-4-sulfonamide | 3.30* LCMS/ 491 [M + H]⁺ | 111B |
| 119 | H | | N-(1-Benzyl-6-(4-fluorophenyl)-1,2,3,4-tetrahydroquinolin-3-yl)-5-(oxazol-5-yl)-thiophene-2-sulfonamide | 4.25* LCMS/ 546 [M + H]⁺ | 111B |

TABLE 6-continued

| Ex. No. | R | A | Compound Name | Retention Time (min.)/m/z | See Ex. |
|---|---|---|---|---|---|
| 120 | H | (thiophene-isoxazole) | N-(1-Benzyl-6-(4-fluorophenyl)-1,2,3,4-tetrahydroquinolin-3-yl)-5-(isoxazole-3-yl)thiophene-2-sulfonamide | 3.68* LCMS/ 546 [M + H]⁺ | 111B |
| 121 | H | (5-chlorothiophene) | N-(1-Benzyl-6-(4-fluorophenyl)-1,2,3,4-tetrahydroquinolin-3-yl)-5-chlorothiophene-2-sulfonamide | 3.51* LCMS/ 513 [M + H]⁺ | 111B |
| 122 | H | (5-methyl-2-(trifluoromethyl)furan) | N-(1-Benzyl-6-(4-fluorophenyl)-1,2,3,4-tetrahydroquinolin-3-yl)-5-methyl-2-(trifluoromethyl)furan-3-sulfonamide | 3.55* LCMS/ 545 [M + H]⁺ | 111B |
| 123 | H | (pyridin-2-yl) | N-(1-Benzyl-6-(4-fluorophenyl)-1,2,3,4-tetrahydroquinolin-3-yl)pyridine-2-sulfonamide | 7.96 LCMS/ 474 [M + H]⁺ | 111B |
| 124 | H | (pyridin-3-yl) | N-(1-Benzyl-6-(4-fluorophenyl)-1,2,3,4-tetrahydroquinolin-3-yl)pyridine-3-sulfonamide | 7.97 LCMS/ 474 [M + H]⁺ | 111B |
| 125 | H | (5-CF₃ pyridin-2-yl) | N-(1-Benzyl-6-(4-fluorophenyl)-1,2,3,4-tetrahydroquinolin-3-yl)-5-(trifluoromethyl)pyridine-2-sulfonamide | 4.30* LCMS/ 576 [M + H]⁺ | 111B |
| 126 | H | (3-fluorophenyl) | N-(1-Benzyl-6-(4-fluorophenyl)-1,2,3,4-tetrahydroquinolin-3-yl)-3-fluorobenzene sulfonamide | 8.40 LCMS/ 491 [M + H]⁺ | 111B |
| 127 | H | (3-chlorophenyl) | N-(1-Benzyl-6-(4-fluorophenyl)-1,2,3,4-tetrahydroquinolin-3-yl)-3-chlorobenzene sulfonamide | 8.60 LCMS/ 508 [M + H]⁺ | 111B |
| 128 | H | (3-methylphenyl) | N-(1-Benzyl-6-(4-fluorophenyl)-1,2,3,4-tetrahydroquinolin-3-yl)-3-methylbenzene sulfonamide | 8.54 LCMS/ 487 [M + H]⁺ | 111B |
| 129 | H | (3-cyanophenyl) | N-(1-Benzyl-6-(4-fluorophenyl)-1,2,3,4-tetrahydroquinolin-3-yl)-3-cyanobenzene sulfonamide | 8.17 LCMS/ 498 [M + H]⁺ | 111B |

TABLE 6-continued

| Ex. No. | R | A | Compound Name | Retention Time (min.)/m/z | See Ex. |
|---|---|---|---|---|---|
| 130 | H | 3,5-difluorophenyl | N-(1-Benzyl-6-(4-fluorophenyl)-1,2,3,4-tetrahydroquinolin-3-yl)-3,5-difluorobenzene sulfonamide | 8.60 LCMS/ 509 [M + H]⁺ | 111B |
| 131 | H | benzyl | N-(1-Benzyl-6-(4-fluorophenyl)-1,2,3,4-tetrahydroquinolin-3-yl)(phenyl)methane sulfonamide | 8.37 LCMS/ 487 [M + H]⁺ | 111B |
| 132 | H | pyridin-3-ylmethyl | N-(1-Benzyl-6-(4-fluorophenyl)-1,2,3,4-tetrahydroquinolin-3-yl)(pyridin-3-yl)methane sulfonamide | 7.43 LCMS/ 488 [M + H]⁺ | 111B |
| 133 | H | pyridin-4-ylmethyl | N-(1-Benzyl-6-(4-fluorophenyl)-1,2,3,4-tetrahydroquinolin-3-yl)(pyridin-4-yl)methane sulfonamide | 7.17 LCMS/ 488 [M + H]⁺ | 111B |
| 134 | H | pyridin-2-ylmethyl | N-(1-Benzyl-6-(4-fluorophenyl)-1,2,3,4-tetrahydroquinolin-3-yl)(pyridin-2-yl)methane sulfonamide | 7.17 LCMS/ 488 [M + H]⁺ | 111B |
| 135 | H | styryl | N-(1-Benzyl-6-(4-fluorophenyl)-1,2,3,4-tetrahydroquinolin-3-yl)-2-phenylethene sulfonamide | 8.55 LCMS/ 499 [M + H]⁺ | 111B |
| 136 | Cl | phenyl | N-(1-(3-Chlorobenzyl)-6-(4-fluorophenyl)-1,2,3,4-tetrahydroquinolin-3-yl)benzenesulfonamide | 7.05 LCMS/ 507 [M + H]⁺ | 113 |
| 137 | F | phenyl | N-(1-(3-Fluorobenzyl)-6-(4-fluorophenyl)-1,2,3,4-tetrahydroquinolin-3-yl)benzenesulfonamide | 6.79 LCMS/ 491 [M + H]⁺ | 113 |
| 138 | CH₃ | phenyl | N-(1-(3-Methylbenzyl)-6-(4-fluorophenyl)-1,2,3,4-tetrahydroquinolin-3-yl)benzenesulfonamide | 7.67 LCMS/ 487 [M + H]⁺ | 113 |
| 139 | OCH₃ | phenyl | N-(1-(3-Methoxylbenzyl)-6-(4-fluorophenyl)-1,2,3,4-tetrahydroquinolin-3-yl)benzenesulfonamide | 7.13 LCMS/ 503 [M + H]⁺ | 113 |

TABLE 6-continued

| Ex. No. | R | A | Compound Name | Retention Time (min.)/m/z | See Ex. |
|---|---|---|---|---|---|
| 140 | Cl | ![3,5-difluorophenyl] | N-(1-(3-Chlorobenzyl)-6-(4-fluorophenyl)-1,2,3,4-tetrahydroquinolin-3-yl))-3,5-difluorobenzene sulfonamide | 4.4* LCMS/ 543 [M + H]+ | 113 |
| 141 | Cl | ![3-cyanophenyl] | N-(1-(3-Chlorobenzyl)-6-(4-fluorophenyl)-1,2,3,4-tetrahydroquinolin-3-yl))-3-cyanobenzene sulfonamide | 4.2* LCMS/ 533 [M + H]+ | 113 |

Example 142

3-Benzenesulfonylamino-1-benzyl-1,2,3,4-tetrahydroquinoline-6-carboxylic acid amide

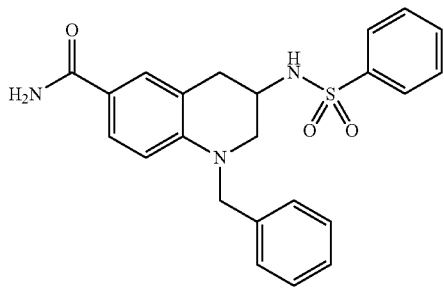

To a solution of racemate 5 (100 mg, 0.25 mmol) in MeOH (2 mL) at RT was added 1N aqueous NaOH (0.13 mL), followed by 30% hydrogen peroxide (0.1 mL). The mixture was stirred at 65° C. for 24 h, cooled to RT and concentrated. The residue was partitioned between H$_2$O and CH$_2$Cl$_2$, and the separated CH$_2$Cl$_2$ layer was concentrated. The crude product was purified using preparative HPLC (YMC S5 ODS 20×100 mm) eluting with MeOH (50-80%) in H$_2$O for 8 min, and then 80% MeOH in H$_2$O for 7 min to give the title compound (64 mg, 62%) as a white solid. HPLC: 99% at 6.05 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 422 [M+H]+.

Example 143

3-Benzenesulfonylamino-1-benzyl-1,2,3,4-tetrahydroquinoline-6-carboxylic acid

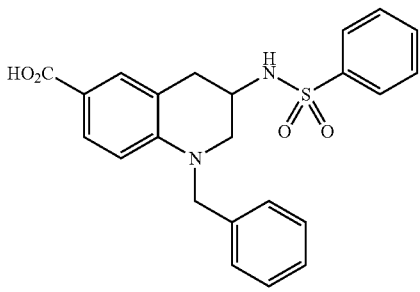

To a solution of racemate 5 (188 mg, 0.47 mmol) in EtOH (4 mL) at RT was added 20% aqueous NaOH (2 mL). The mixture was stirred at 80° C. for 60 h, cooled to RT, adjusted to pH 7 with 1N aqueous HCl and extracted with CH$_2$Cl$_2$ (15 mL×3). The combined CH$_2$Cl$_2$ extracts were washed with brine, dried (Na$_2$SO$_4$), and concentrated. The crude product was purified using preparative HPLC as described in 142 to give the title compound (84 mg, 43%) as a white solid. HPLC: 99% at 6.61 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 423 [M+H]+.

Example 144

N-[1-Benzyl-6-(morpholine-4-carbonyl)-1,2,3,4-tetrahydroquinolin-3-yl]-benzenesulfonamide

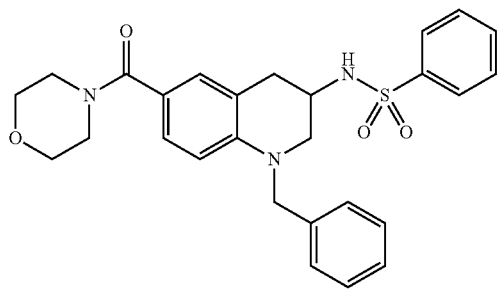

To a solution of compound 143 (74 mg, 0.175 mmol) in anhydrous DMF (2 mL) was added morpholine (27 mg, 0.31 mmol), followed by EDAC (72 mg, 0.375 mmol), HOBt (58 mg, 0.3765 mmol) and NMM (89 mg, 0.88 mmol). The mixture was stirred at RT for 2 h, then partitioned between H$_2$O (20 mL) and EtOAc (20 mL). The aqueous layer was extracted with EtOAc (15 mL×2) and the combined EtOAc extracts were washed with brine, dried (Na$_2$SO$_4$) and concentrated. The crude product was chromatographed (silica gel) eluting with EtOAc-hexane to give the title compound (65 mg, 75%) as a white solid. HPLC: 99% at 6.58 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 492 [M+H]+.

Example 145

N-[1-Benzyl-6-(piperidine-1-carbonyl)-1,2,3,4-tetrahydrquinolin-3-yl]-benzenesulfonamide

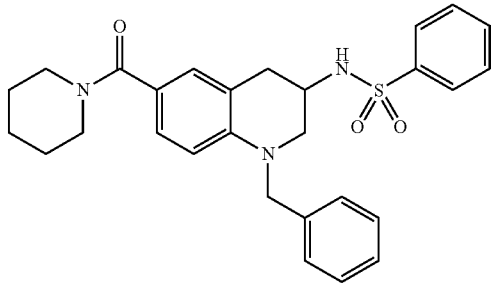

The title compound was prepared from 143 and piperidine by procedure analogous to those described in Example 144. HPLC: 99% at 7.37 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 490 $[M+H]^+$.

Example 146

N-[1-Benzyl-6-(pyrrolidine-1-carbonyl)-1,2,3,4-tetrahydroquinolin-3-yl]-benzenesulfonamide

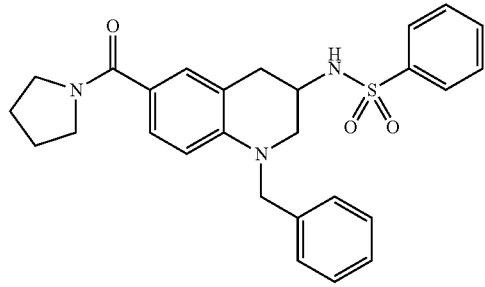

The title compound was prepared from 143 and pyrrolidine by procedure analogous to those described in Example 144. HPLC: 99% at 7.01 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 476 $[M+H]^+$.

Example 147

N-(1-Benzyl-6-(4-fluorophenyl)-4-(trifluoromethyl)-1,2,3,4-tetrahydroquinolin-3-ylbenzenesulfonamide

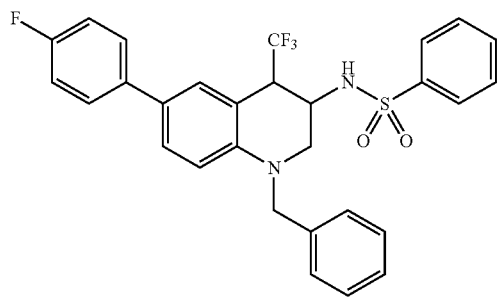

147A.
6-Chloro-4-(trifluoromethyl)-3-aminoquinoline

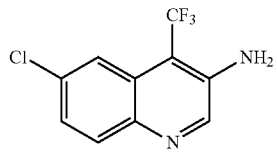

To a solution of 6-chloro-3-nitro-4-(trifluoromethyl) quinoline (5.53 g, 20 mmol) (prepared according to the procedures described by Tarby, C. M., in WO 2003062238) in EtOAc (100 mL) was added $SnCl_2.2H_2O$ (18 g, 80 mmol). The resulting mixture was stirred at RT for 18 h, then at 80° C. for 6 h. After cooling to RT, saturated aqueous $K_2CO_3$ (5 mL) was added. The reaction mixture was stirred at RT for 30 min, and then solid $K_2CO_3$ (16.6 g, 120 mmol) was added stirring was continued at RT for 4 more hours. EtOAc (200 mL) was added, the resulting mixture was filtered, and the filtrate concentrated in vacuo to give the title compound (4.8 g, 97% yield) as an off-white solid.

147B. 6-(4-Fluorophenyl)-4-(trifluoromethyl)-3-aminoquinoline

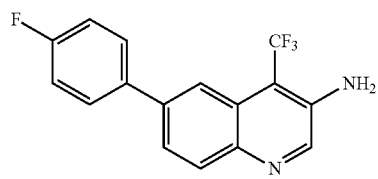

The title compound was prepared from 147A using the procedures analogous to those described in Example 89E.

147C. 6-(4-Fluorophenyl)-4-(trifluoromethyl)-1,2,3,4-tetrahydroquinolin-3-amine

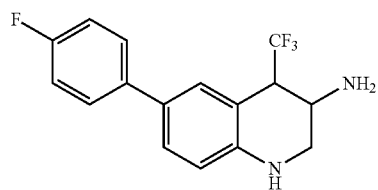

To a solution of 147B (400 mg, 1.3 mmol) in EtOAc (5 mL)-MeOH (15 mL) was bubbled with $N_2$ for 15 min, then palladium hydroxide (20 weight % palladium on carbon) (200 mg) was added. The resulting suspension was subjected to hydrogenation under 80 psi of pressure for 16 h., then filtered. The filtrate was concentrated. The residue was chromatographed (silica gel) eluting with 20% EtOAc in hexane (100 mL), 50% EtOAc in hexane (100 mL), 100% ETOAc (100 mL), 5% MeOH in EtOAc (150 mL) to give title compound (62 mg, 15% yield) as a white foam.

147D. N-(6-(4-Fluorophenyl)-4-(trifluoromethyl)-1,2,3,4-tetrahydroquinolin-3-yl)benzenesulfonamide

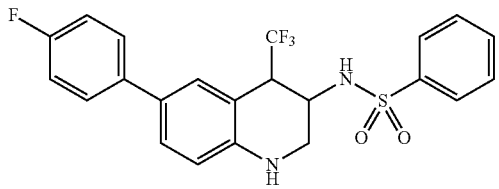

The title compound was prepared from 147C using the procedures analogous to those described in Example 1G.

147E. N-(1-Benzyl-6-(4-fluorophenyl)-4-(trifluoromethyl)-1,2,3,4-tetrahydroquinolin-3-yl)benzenesulfonamide The title compound was prepared from 147D using the procedures analogous to those described in Example 22A. HPLC: 99% at 8.30 min (retention time) (Conditions: Zorbax SB C18 (4.6×75 mm); Eluted with 0% to 100% B, 8 min gradient (A=90% $H_2O$–10% MeOH–0.1% $H_3PO_4$ and B=10% $H_2O$–90% MeOH–0.1% $H_3PO_4$); Flow rate at 2.5 mL/min, UV detection at 220 nm). MS (ES): m/z 541 $[M+1]^+$.

Example 148

N-(1-Benzyl-6-(4-fluorophenyl)-3-methyl-1,2,3,4-tetrahydroquinolin-3-yl)benzenesulfonamide

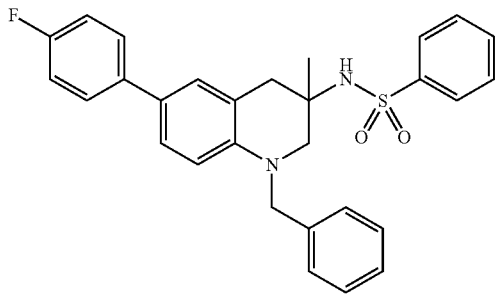

148A. Ethyl-3-methyl-2-oxo-1,2,3,4-tetrahydroquinoline-3-carboxylate

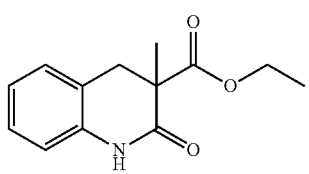

The title compound was prepared following the procedures described by Turconi, M., et al., in Bioorganic & Medicinal Chemistry, 2, 1375-1383 (1994).

148B. Ethyl 6-bromo-3-methyl-2-oxo-1,2,3,4-tetrahydroquinoline-3-carboxylate

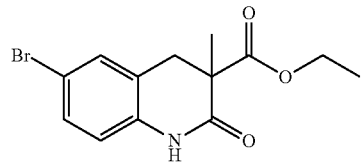

The title compound was prepared from 148A using the procedures analogous to those described in Example 87E.

148C. 6-Bromo-3-methyl-2-oxo-1,2,3,4-tetrahydroquinoline-3-carboxylic acid

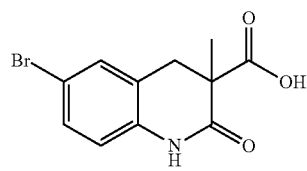

The title compound was prepared from 148B using the procedures analogous to those described in Example 149D.

148D. Benzyl-6-bromo-3-methyl-2-oxo-1,2,3,4-tetrahydroquinolin-3-ylcarbamate

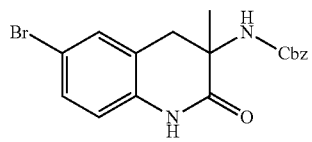

The title compound was prepared from 148C using the procedures analogous to those described in Example 149E.

148E. Benzyl 1-benzyl-6-bromo-3-methyl-2-oxo-1,2,3,4-tetrahydroquinolin-3-ylcarbamate

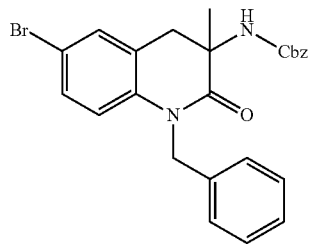

The title compound was prepared from 148D using the procedures analogous to those described in Example 87F.

148F. Benzyl 1-benzyl-6-(4-fluorophenyl)-3-methyl-2-oxo-1,2,3,4-tetrahydro quinolin-3-ylcarbamate

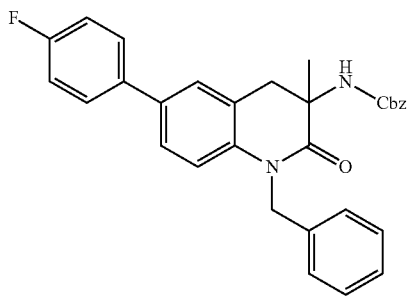

The title compound was prepared from 148E using the procedures analogous to those described in Example 89E.

148G. 1-Benzyl-6-(4-fluorophenyl)-3-methyl-2-oxo-1,2,3,4-tetrahydroquinolin-3-amine

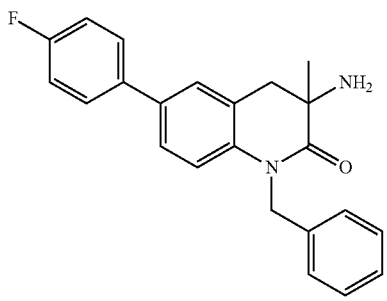

To a solution of 148F (340 mg, 0.69 mmol) in MeOH (8 mL) was added 5% palladium on carbon (200 mg). The resulting suspension was hydrogenated under hydrogen balloon for 1 h., then filtered. The filtrate was concentrated to give title compound (235 mg, 94% yield) as an off-white foam.

148H. N-(1-benzyl-6-(4-fluorophenyl)-3-methyl-2-oxo-1,2,3,4-tetrahydro quinolin-3-yl)benzenesulfonamide

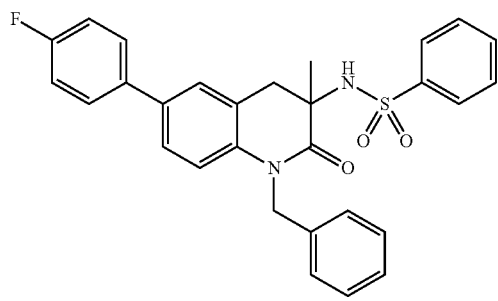

The title compound was prepared from 148G using the procedures analogous to those described in Example 1G.

148I. N-(1-benzyl-6-(4-fluorophenyl)-3-methyl-1,2,3,4-tetrahydroquinolin-3-yl)benzenesulfonamide

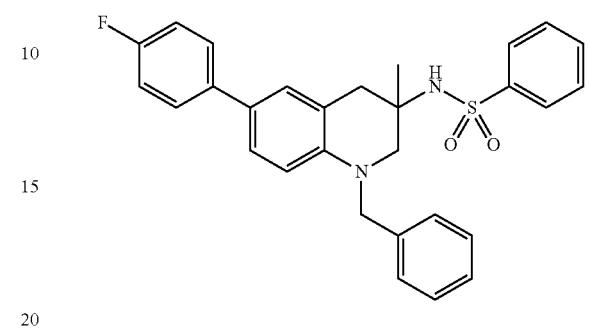

To compound 148H ((75 mg, 0.15 mmol) was added BH$_3$THF (1M, 1.5 mL, 1.5 mmol) at RT under Argon. After addition, the reaction was stirred at RT for 24 h, then quenched by carefully adding MeOH (1 mL). The resulting mixture was stirred at RT for 2 h, then partitioned between saturated aqueous Na$_2$CO$_3$ (10 mL) and EtOAc. The aqueous layer was extracted with EtOAc (15 mL×3) and the combined EtOAc extracts washed with brine, dried (Na$_2$SO$_4$), and concentrated. The resulting residue was chromatographed (silica gel) eluting with EtOAc (0-40%) in hexane to give the title compound as an off-white solid (40 mg, 55%). HPLC: 99% at 8.50 min (retention time) (Conditions: Zorbax SB C18 (4.6× 75 mm); Eluted with 0% to 100% B, 8 min gradient (A=90% H$_2$O–10% MeOH–0.1% H$_3$PO$_4$ and B=10% H$_2$O–90% MeOH–0.1% H$_3$PO$_4$), Flow rate at 2.5 mL/min, UV detection at 220 nm). MS (ES): m/z 487 [M+H]$^+$.

Example 149

(S)—N-(1)-Benzyl-6-(trifluoromethyl)-1,2,3,4-tetrahydroquinolin-3-yl)benzenesulfonamide

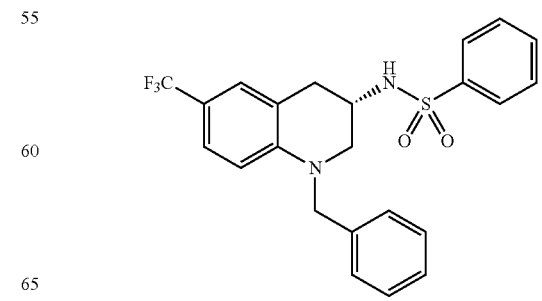

149A. Ethyl 4-chloro-6-(trifluoromethyl)quinoline-3-carboxylate

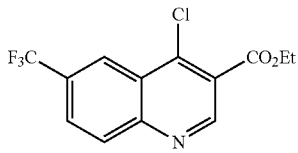

The title compound was prepared from ethyl 4-hydroxy-6-(trifluoromethyl) quinoline-3-carboxylate according to the procedures described in U.S. Pat. No. 4,343,804.

149B. Ethyl 6-(trifluoromethyl)-1,2,3,4-tetrahydroquinoline-3-carboxylate

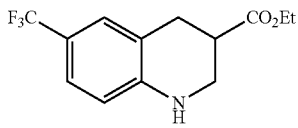

The title compound was prepared from 149A using the procedures analogous to those described in Example 1A.

149C. Ethyl 1-benzyl-6-(trifluoromethyl)-1,2,3,4-tetrahydroquinoline-3-carboxylate

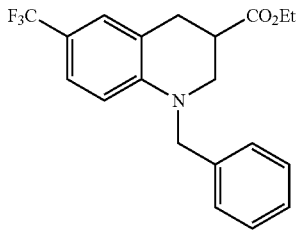

The title compound was prepared from 149B using the procedures analogous to those described in Example 22A.

149D. 1-Benzyl-6-(trifluoromethyl)-1,2,3,4-tetrahydroquinoline-3-carboxylic acid

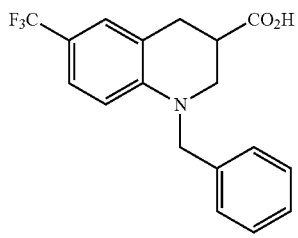

To a solution of 149C (825 mg, 2.27 mmol) in a mixed solvent of MeOH-THF-H$_2$O (20 mL at ratio of 2:2:1) was added lithium hydroxide monohydrate (400 mg, 11.35 mmol). The mixture was stirred at RT for 2 h, then extracted with ether (20 mL). The aqueous layer was acidified to pH 4-5 using 3N aqueous HCl, then extracted with CH$_2$Cl$_2$ (3×). The combined CH$_2$Cl$_2$ extracts were washed with water, brine, dried (Na$_2$SO$_4$), and concentrated in vacuo to afford compound 149D as light yellow foam (735 mg, 97%).

149E. Benzyl 1-benzyl-6-(trifluoromethyl)-1,2,3,4-tetrahydroquinolin-3-ylcarbamate

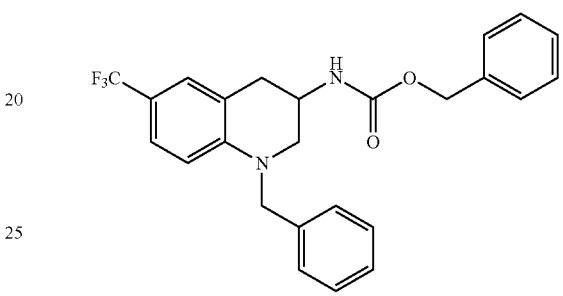

To a solution of 149D (345 mg, 1.029 mmol) in dioxane (3.5 mL) was added diphenylphosphoryl azide (244 μL, 1.133 mmol) and triethylamine (170 μL, 1.236 mmol). The reaction mixture was stirred at RT for 20 min, then benzylalcohol (130 μL, 1.236 mmol) was added. The reaction was heated at 100° C. for 7 h. After cooling to RT, the reaction mixture was concentrated in vacuo, and the residue partitioned between EtOAc and water. The separated organic layer was washed with brine, dried (Na$_2$SO$_4$), and concentrated in vacuo. The residue was chromatographed (silica gel) eluting with EtOAc/hexane 0-40% to afford 149E as a clear oil (390 mg, 86%).

149F. 1-Benzyl-6-(trifluoromethyl)-1,2,3,4-tetrahydroquinolin-3-amine

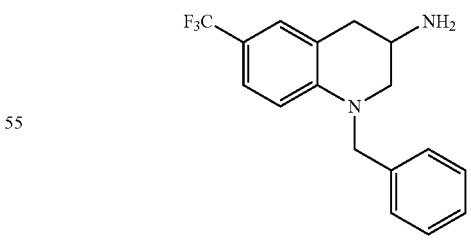

A suspension of 149E (740 mg, 1.682 mmol) and 5% Pd/C (Degussa type, 300 mg) in a mixed solvent of MeOH-THF (20 mL, 1:1 ratio) was hydrogenated ar RT under hydrogen balloon for 1 h. After filtration to remove the catalyst, the filtrate was concentrated and the residue dried in vacuo to afford compound 149F as a clear oil (465 mg, 90%).

149G. N-(1-Benzyl-6-(trifluoromethyl)-1,2,3,4-tetrahydroquinolin-3-yl)benzenesulfonamide

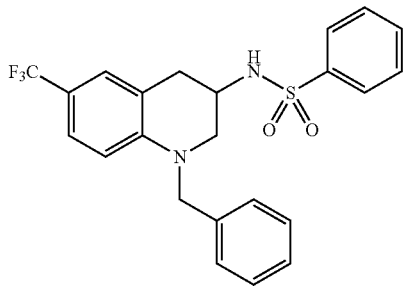

The title compound was prepared from 149F using the procedures analogous to those described in Example 1G.

149H. (S)—N-(1-Benzyl-6-(trifluoromethyl)-1,2,3,4-tetrahydroquinolin-3-yl)benzenesulfonamide The title compound was separated from 149G using a Chiralpak AD column (5×50 cm, 20 μm chiral stationary phase) eluting with 30% isopropanol in heptane.

HPLC: 99% at 7.81 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 447 [M+1]$^+$. Chiral HPLC 99% e.e.; retention time=10.1 min; Conditions: AD (4.6×250 mm); Eluted with 30% isopropanol in heptane for 30 min at 1 mL/min.

Example 150

(R)—N-(1-Benzyl-6-(trifluoromethyl)-1,2,3,4-tetrahydroquinolin-3-yl)benzenesulfonamide

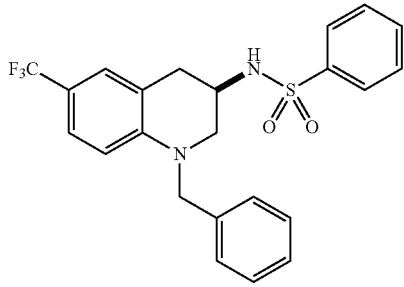

The title compound was obtained via chiral chromatographic separation of racemic 149G using a Chiralpak AD column (5×50 cm, 20 μm chiral stationary phase) eluting with 30% isopropanol in heptane. HPLC: 99% at 7.82 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 447 [M+1]$^+$. Chiral HPLC 99% e.e.; retention time=5.49 min; Conditions: AD (4.6×250 mm); Eluted with 30% isopropanol in heptane for 30 min at 1 mL/min.

Example 151

N-(1-Benzyl-7-(trifluoromethyl)-1,2,3,4-tetrahydroquinolin-3-yl)benzenesulfonamide

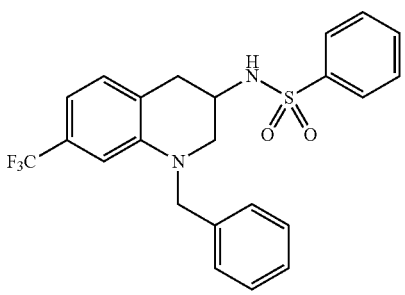

The title compound was prepared from ethyl 4-hydroxy-7-(trifluoromethyl) quinoline-3-carboxylate by the procedures analogous to those described in Example 149. HPLC: 97% at 7.75 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 447 [M+1]$^+$.

Example 152

N-(1-Benzyl-7-chloro-1,2,3,4-tetrahydroquinolin-3-yl)-3,5-difluorobenzenesulfonamide

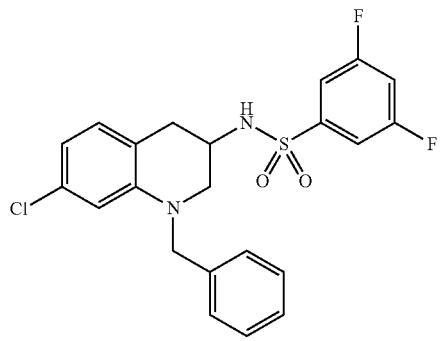

152A. 2-Amino-3-(4-chloro-2-nitrophenyl)propanoic acid

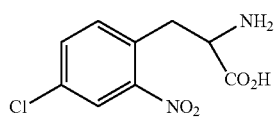

The title compound was prepared from 4-chloro-2-nitrobenzyl chloride and diethylacetamidomalonate according to the procedures described by Davis, A. L.; et al, in *Arch. Biochem. Biophys.*, 102, 48 (1963).

152B.
3-Amino-7-chloro-3,4-dihydroquinolin-2(1H)-one

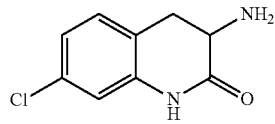

To a solution of 152A (1.0 g, 4.1 mmol) in 50% aqueous EtOH (40 mL), 10% Pt/C (100 mg) was added under argon and the mixture was hydrogenated at 35 psi for 1 h. The reaction mixture was filtered via a pad of celite and the filtrate was concentrated. The residue was dissolved in conc. HCl (10 mL) and stirred at RT for 6 h. The mixture was then concentrated and dissolved in 100 mL of saturated aqueous sodium bicarbonate. The white solid was filtered and dried to afford 0.44 g of 152B.

152C. 7-Chloro-N-(1,2,3,4-tetrahydroquinolin-3-yl)-3,5-difluoro-benzene-sulfonamide

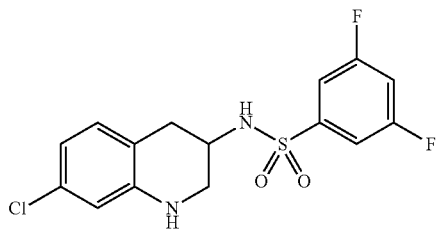

To a solution of 152B (50 mg, 0.22 mmol) in 1 mL THF, lithium aluminum hydride (81 mg, 2.2 mmol) was added and the mixture refluxed under argon for 16 h. Excess LAH was quenched with MeOH and the mixture partitioned between saturated aqueous NaHCO$_3$ and EtOAc. The organic layer was separated, washed with water, brine, dried (MgSO$_4$) and evaporated to afford 21 mg of a colorless gum. To a solution of this material in 1 mL of DCM was added triethylamine (0.24 mL, 0.96 mmol), followed by 3,5-difluorobenzene-sulfonylchloride (20.4 mg, 0.09 mmol). The mixture was stirred at RT for 1.5 h, then concentrated in vacuo. The residue was taken into EtOAc (30 mL), washed with water, brine, dried (MgSO$_4$) and concentrated to give 37 mg of 152C.

152D. N-(1-Benzyl-7-chloro-1,2,3,4-tetrahydro-quinolin-3-yl)-3,5-difluoro-benzenesulfonamide The title compound was prepared from 152C and 3-chlorobenzaldehyde by procedures analogous to those described in Example 22A. HPLC: 99% at 4.20 min (retention time) (Conditions: Phenom Prime S5, C18 (4.6×50 mm); Eluted with 0% to 100% B, 4 min gradient (A=90% H$_2$O–10% MeOH–0.1% TFA and B=10% H$_2$O–90% MeOH–0.1% TFA); Flow rate at 4.0 mL/min, UV detection at 220 nm). MS (ES): m/z 484 [M+H]$^+$.

Example 153

N-(6-Cyano-1-phenyl-1,2,3,4-tetrahydroquinolin-3-yl)benzenesulfonamide

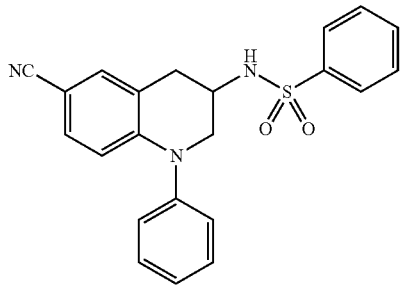

153A. N-(6-Cyano-1,2,3,4-tetrahydroquinolin-3-yl)-benzenesulfonamide

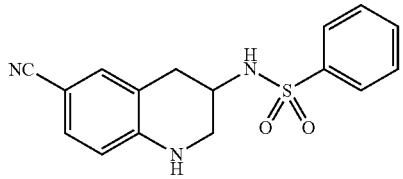

Compound 153A was prepared from 1D by procedures analogous to those described in Example 1G.

153B. N-(6-Cyano-1-phenyl-1,2,3,4-tetrahydro-quinolin-3-yl)-benzene-sulfonamide

To a s mixture of 153A (235 mg, 0.75 mmol), Pd(OAc)$_2$ (8.4 mg, 0.0375 mmol), BINAP (25.7 mg, 0.041 mmol), bromobenzene (94.2 mg, 0.6 mmol) in toluene (1.5 mL) was added KOtBu (98 mg, 0.88 mmol) at RT under argon. The resulting mixture was stirred at 100° C. under argon for 16 h. After cooling to RT, residue was diluted with 5% citric acid, then extracted with EtOAc (3×10 mL). The combined EtOAc extracts were washed with brine, dried (Na$_2$SO$_4$), and concentrated. The resulting residue was chromatographed (silica gel) eluting with EtOAc (50-90%) in hexane to give the title compound as a white foam (25 mg, 8.6%). HPLC: 99% at 6.9 min (retention time) (Conditions: Zorbax SB C18 (4.6×75 mm); Eluted with 0% to 100% B, 8 min gradient (A=90% H$_2$O–10% MeOH–0.1% H$_3$PO$_4$ and B=10% H$_2$O–90%

MeOH–0.1% H₃PO₄); Flow rate at 2.5 mL/min, UV detection at 220 nm). MS (ES): m/z 390 [M+1]⁺.

Example 154

N-(1-(3-Chlorophenyl)-6-cyano-1,2,3,4-tetrahydro-quinolin-3-yl)-benzene-sulfonamide

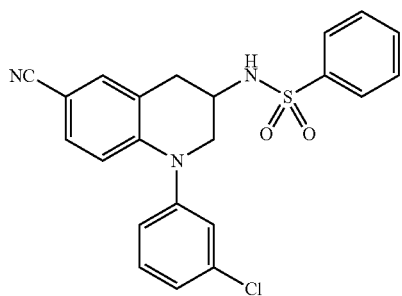

154A. N-(6-Cyano-1,2,3,4-tetrahydroquinolin-3-yl)-N-(2-(trimethylsilyl)ethoxy)methyl)-benzenesulfonamide

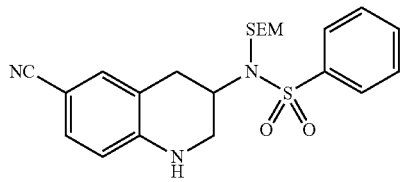

To a solution of 153A (627 mg, 2 mmol) in DMF (5 mL) at RT was added NaH (96 mg, 2.4 mmol) in portions. After addition, the reaction was stirred at RT for 30 min, and then 2-(trimethylsilyl)ethoxymethyl chloride (0.37 mL, 2.10 mmol) was added dropwise. After addition, the reaction was stirred at RT for 1 h, then quenched carefully with water. The mixture was extracted with EtOAc (3×30 mL), and the combined extracts washed with brine, dried (Na₂SO₄), and concentrated. The resulting residue was chromatographed (silica gel) eluting with EtOAc (0-60%) in hexane to give the title compound as a white powder (620 mg, 70%).

154B. N-(1-(3-Chlorophenyl)-6-cyano-1,2,3,4-tetrahydroquinolin-3-yl)-N-(2-(trimethylsilyl)ethoxy)methyl)-benzenesulfonamide

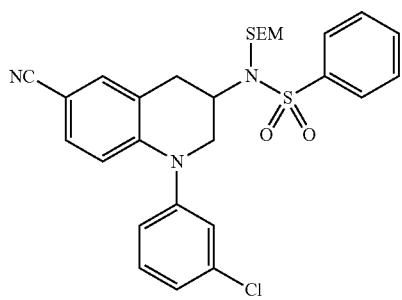

The title compound was prepared from 154A and 1-chloro-3-iodobenzene by procedures analogous to those described in Example 153B.

154C. N-(1-(3-Chlorophenyl)-6-cyano-1,2,3,4-tetrahydroquinolin-3-yl)-benzene-sulfonamide To a solution of 154B (100 mg, 0.18 mmol) in THF (1 mL) at RT was added 1.0 M solution of tetrabutylammonium fluoride in THF (2 mL, 2 mmol). The resulting solution was stirred at RT under argon for 24 h. The reaction was diluted with water, then extracted with EtOAc (3×15 mL). The combined EtOAc extracts were washed with 1.0 M aqueous HCl, saturated aqueous NaHCO₃, brine, dried (Na₂SO₄), and concentrated. The resulting residue was chromatographed (silica gel) eluting with EtOAc (0-50%) in hexane to give the title compound as a white foam (25 mg, 33%). HPLC: 99% at 7.3 min (retention time) (Conditions: Zorbax SB C18 (4.6×75 mm); Eluted with 0% to 100% B, 8 min gradient (A=90% H₂O–10% MeOH–0.1% H₃PO₄ and B=10% H₂O–90% MeOH–0.1% H₃PO₄); Flow rate at 2.5 mL/min, UV detection at 220 nm). MS (ES): m/z 424 [M+1]⁺.

Example 155

(S)-Piperidine-1-sulfonic acid (1-benzyl-6-cyano-1,2,3,4-tetrahydroquinolin-3-yl)-amide

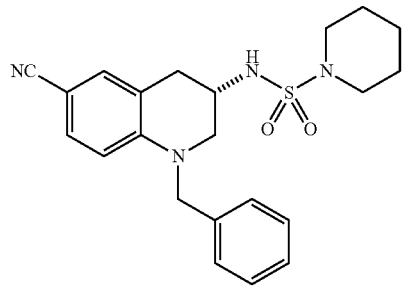

155A. (S)-Piperidine-1-sulfonic acid-(6-cyano-1,2,3,4-tetrahydroquinolin-3-yl)-amide

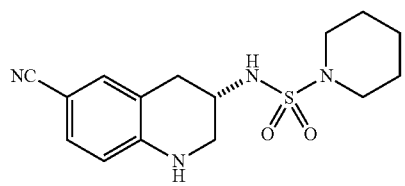

Using procedures analogous to those described in Example 1G, compound 155A was prepared from 1F and piperidine-1-sulfonyl chloride (prepared according to the procedures described by Padma, D. K.; Bhat, V. Subrahmanya; Murthy, A. R. Vasudeva, in *J. Fluorine Chem.*, EN. 20, 425-438 (1982)).

155B. (S)-Piperidine-1-sulfonic acid-(1-benzyl-6-cyano-1,2,3,4-tetrahydro-quinolin-3-yl)amide The title compound was prepared from 155A and benzaldehyde by procedures analogous to those described in Example 22A. HPLC: 99% at 7.2 min (retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 411 [M+1]$^+$. Chiral HPLC 100% e.e.; retention time=29.7 min; Conditions: AD (4.6×250 mm); Eluted with 25% isopropanol in hexane for 60 min at 1 mL/min.

Example 156

Morpholine-4-sulfonic acid[1-(3-chloro-benzyl)-6-cyano-1,2,3,4-tetrahydro-quinolin-3-yl]-amide

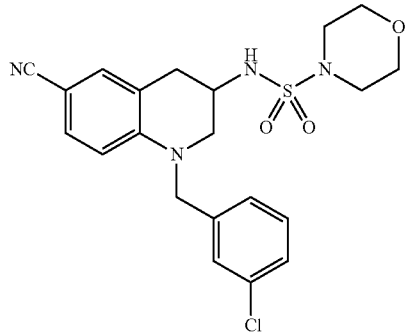

156A. Morpholine-4-sulfonic acid-(6-cyano-1,2,3,4-tetrahydroquinolin-3-yl)-amide

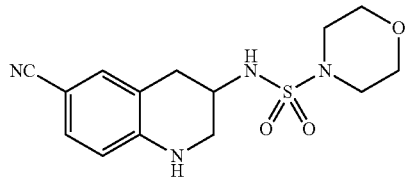

Using procedures analogous to those described in Example 1F, compound 156A was prepared from 1D and morpholine-4-sulfonyl chloride (prepared following the procedures described by Antonio Vandi et al, in *J. Org. Chem.* 26, 3478-3480, (1961)).

156B. Morpholine-4-sulfonic acid-[1-(3-chloro-benzyl)-6-cyano-1,2,3,4-tetrahydroquinolin-3-yl]-amide The title compound was prepared from 156A and 3-chlorobenzaldehyde by procedures analogous to those described in Example 22A. HPLC: 99% at 6.7 min(retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 447 [M+1]$^+$.

Example 157

N-(1-Benzyl-6-cyano-1,2,3,4-tetrahydroquinolin-3-yl)-2-oxooxazolidine-3-sulfonamide

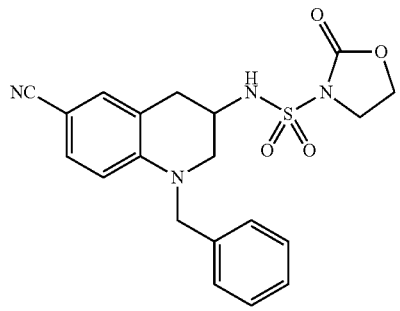

157A. 3-Amino-1-benzyl-1,2,3,4-tetrahydroquinoline-6-carbonitrile

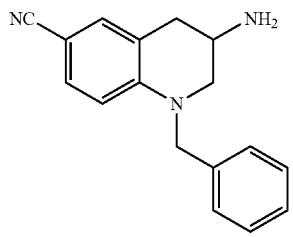

157A was prepared from 1C and benzaldehyde by procedures analogous to those described in Example 22A, followed by removal of N-Boc protecting group according to the procedures described in Example 22B.

157B. N-(1-Benzyl-6-cyano-1,2,3,4-tetrahydroquinolin-3-yl)-2-oxooxazolidine-3-sulfonamide The title compound was prepared from 157A according to the procedures described by Ducry, L., et al., in *Helv. Chim Acta,* 82, 2432-2447, (1999). HPLC: 99% at 6.11 min(retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 413 [M+1]$^+$.

Example 158

N-(1-Benzyl-6-cyano-1,2,3,4-tetrahydroquinolin-3-yl)-cyclohexylamino-3-sulfonamide

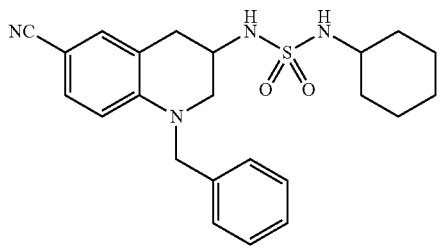

To a solution of 157B (41.2 mg, 0.1 mmol) in acetonitril (0.5 mL) was added cyclohexylamine (14 μL, 0.12 mmol), followed by diisopropylethylamine (120 μL) the mixture was shaken at 80° for 16 h. After cooling to RT, the reaction mixture was partitioned between EtOAc and water. The separated organic layer was washed with saturated aqueous ammonium chloride (2×), dried (Na$_2$SO$_4$) and concentrated. The residue was chromatographed (silica gel) eluding with EtOAc/hexane (0-60%) to afford the title compound (28 mg, 66%) as a white solid. HPLC: 99% at 7.34 min(retention time) (Conditions: Zorbax SB C18 (4.6×75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 425 [M+1]$^+$.

Example 159

N-(1-Benzyl-6-cyano-1,2,3,4-tetrahydroquinolin-3-yl)-anilinyl-3-sulfonamide

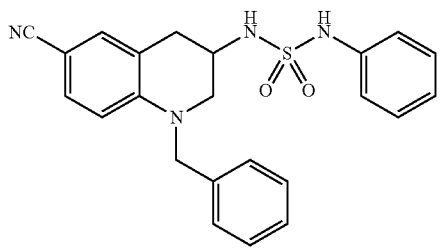

The title compound was prepared from 157B with aniline according to the procedures described in 158. HPLC: 99% at 6.92 min(retention time) (Conditions: Zorbax SB C18 (4.6× 75 mm); Eluted with 0% to 100% B, 8 min gradient. (A=90% H$_2$O–10% MeOH–0.1% H$_3$PO$_4$ and B=10% H$_2$O–90% MeOH–0.1% H$_3$PO$_4$); Flow rate at 2.5 mL/min. UV detection at 220 nm). MS (ES): m/z 419 [M+1]$^+$.

Example 160

(S)—N-(1-Benzoyl-6-cyano-1,2,3,4-tetrahydroquinolin-3-yl)-benzene-sulfonamide

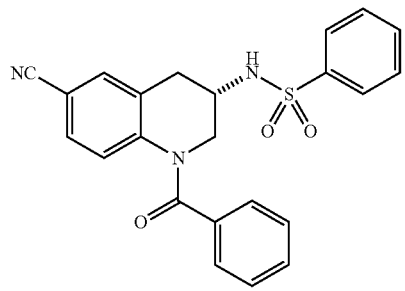

To a solution of 1G (62 mg, 0.2 mmol) in CH$_2$Cl$_2$ (1 mL) was added pyridine (0.049 mL, 0.6 mmol), followed by addition of benzoyl chloride (42 mg, 0.3 mmol). The resulting mixture was stirred at RT under argon for 6 h, then loaded on a silica gel cartridge (10 g), eluting with EtOAc (25-50%) in hexane to give the title compound as a white solid (72 mg, 88%). m.p. 174-175° C., HPLC: 99% at 3.01 min (retention time, Phenom. Luna C18, 4.6×50 mm eluting with 10-90% MeOH/H$_2$O over 4 minutes containing 0.1% TFA; 4 mL/min, monitoring at 220 nm). MS (ES): m/z=418 [M+1]$^+$. Chiral HPLC 100% e.e.; retention time=34.8 min; Conditions: OD (4.6×250 mm); Eluted with 40% isopropanol in hexane at 1 mL/min.

Example 161

(S)—N-[1-(3-Chloro-benzoyl)-6-cyano-1,2,3,4-tetrahydroquinolin-3-yl]-benzenesulfonamide

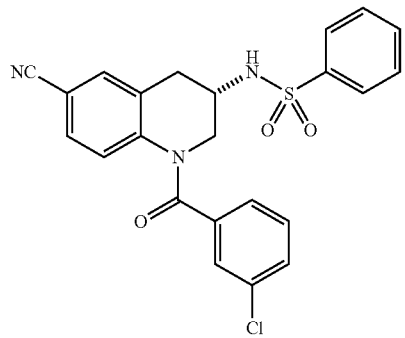

The title compound was prepared from 1G and 3-chlorobenzoyl chloride by procedures analogous to those described in Example 160. HPLC: 100% at 6.3 min(retention time) (Conditions: Zorbax SB C18 (4.6×75 mm); Eluted with 0% to 100% B, 8 min gradient (A=90% H$_2$O–10% MeOH–0.1% H$_3$PO$_4$ and B=10% H$_2$O–90% MeOH–0.1% H$_3$PO$_4$); Flow rate at 2.5 mL/min, UV detection at 220 nm). MS (ES): m/z 452 [M+1]$^+$. Chiral HPLC 100% e.e.; retention time=50.4 min; Conditions: AD (4.6×250 mm); Eluted with 25% isopropanol in hexane for 70 min at 1 mL/min.

Example 162

N-[1-(3-Chloro-benzyl)-1,2,3,4-tetrahydroquinolin-3-yl]-benzenesulfonamide

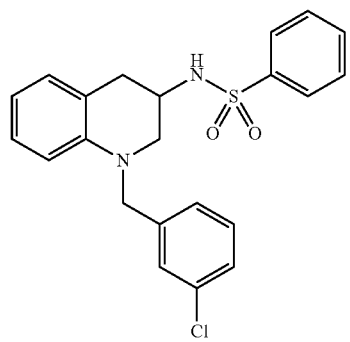

162A. N-(2-Oxo-1,2,3,4-tetrahydroquinolin-3-yl)-benzenesulfonamide

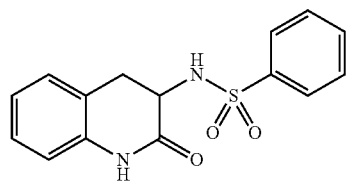

To a suspension of 3-amino-3,4-dihydro-1H-quinolin-2-one (177.6 mg, 0.59 mmol) (prepared according to the procedures by Davis, A. L.; et al, *Arch. Biochem. Biophys.*, 102, 48 (1963)) in $CH_3CN$ (5 mL) was added DIPEA (0.24 mL, 1.44 mmol), followed by addition of benzene sulfonylchloride (0.09 mL, 0.71 mmol). The mixture was stirred at RT for 1.5 h, then concentrated in vacuo. The residue was taken into EtOAc (30 mL), washed with water, brine, dried ($MgSO_4$) and concentrated. The residue was chromatographed (silica gel) eluting with EtOAc (50-90%) in hexane to give the title compound (140 mg, 78%).

162B. N-(1,2,3,4-Tetrahydroquinolin-3-yl)-benzenesulfonamide

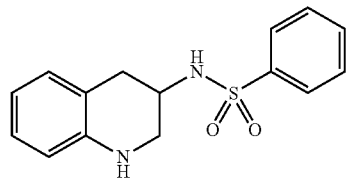

To a solution of LAH (1.0 mL, 1.0 M solution in $Et_2O$) cooled at 0° C. was added dropwise a solution of 162A (120 mg, 0.4 mmol) in THF (5 mL) in 5 min. After addition, the reaction mixture was stirred at RT for 4 h, then quenched by slow addition of EtOAc (2.0 mL), followed by water (15 mL). The mixture was extracted with EtOAc (2×20 mL). The combined EtOAc extracts were washed with water, brine, dried ($MgSO_4$) and concentrated. The residue was chromatographed (silica gel) eluting with EtOAc (30-60%) in hexane to give the title compound (84 mg, 73%).

162C. N-[1-(3-Chlorobenzyl)-1,2,3,4-tetrahydroquinolin-3-yl]-benzene-sulfonamide The title compound was prepared from 162B and 3-chlorobenzaldehyde by procedures analogous to those described in Example 22A. HPLC: 99% at 3.94 min (retention time) (Conditions: Phenom Prime S5, C18 (4.6×50 mm); Eluted with 0% to 100% B, 4 min gradient (A=90% $H_2O$–10% MeOH–0.1% TFA and B=10% $H_2O$–90% MeOH–0.1% TFA); Flow rate at 4.0 mL/min, UV detection at 220 nm). MS (ES): m/z 413 $[M+H]^+$.

Example 163

N-(1-Benzoyl-8-chloro-6-cyano-1,2,3,4-tetrahydroquinolin-3-yl)-benzenesulfonamide

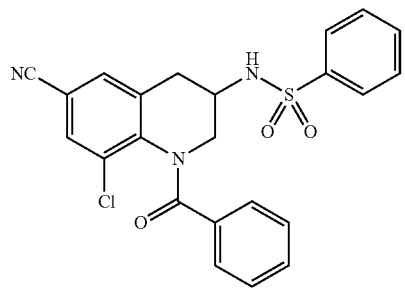

163A. N-(8-chloro-6-cyano-1,2,3,4-tetrahydroquinolin-3-yl)-benzene-sulfonamide

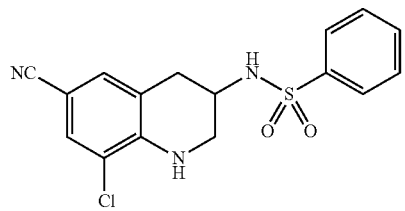

To a suspension of racemate 1G (313.4 mg, 1 mmol) in a mixed solvent of acetic acid (3 mL), THF (3 mL) and $CH_2Cl_2$ (3 mL) at RT was added benzyltrimethyl-ammonium tetrachloroiodate (419 mg, 1 mmol). After addition, the mixture was stirred at RT for 30 min to become a clear yellow solution which was concentrated in vacuo. The residue was triturated with $CH_2Cl_2$ and $H_2O$ and the resultant solid filtered and washed with $CH_2Cl_2$ and $H_2O$, dried in vacuo to give the title compound as an off-white solid (204 mg, 59%).

163B. N-(1-Benzoyl-8-chloro-6-cyano-1,2,3,4-tetrahydroquinolin-3-yl)-benzenesulfonamide To a solution of compound 163A (164 mg, 0.472 mmol) in pyridine (1 mL) and $CH_2Cl_2$ (1 mL) at RT was added benzoyl chloride (82 µL, 0.71 mmol), and the mixture was then stirred at 50° C. for 16 h. After cooling to RT, the reaction was concentrated in vacuo and the resultant residue was taken into MeOH (4 mL), and Et₃N (1 mL) added. The reaction was stirred at 70° C. for 1 h. After cooling to RT, the reaction was concentrated. The residue was diluted with 10% aqueous citric acid, then extracted with EtOAc (3×15 mL). The combined EtOAc extracts were concentrated. The resulting residue was purified using preparative HPLC (YMC S5 ODS 20×100 mm) eluting with MeOH (50-80%) in H₂O for 8 min, and then 80% MeOH in H₂O for 7 min to give the title compound (60 mg, 28%) as a white solid. HPLC: 99% at 6.2 min (retention time) (Conditions: Zorbax SB C18 (4.6×75 mm); Eluted with 0% to 100% B, 8 min gradient. (A=90% H₂O–10% MeOH–0.1% H₃PO₄ and B=10% H₂O–90% MeOH–0.1% H₃PO₄); Flow rate at 2.5 mL/min. UV detection at 220 nm). MS (ES): m/z 452 [M+H]⁺.

Example 164

N-(1-Benzoyl-8-bromo-6-cyano-1,2,3,4-tetrahydroquinolin-3-yl)-benzenesulfonamide

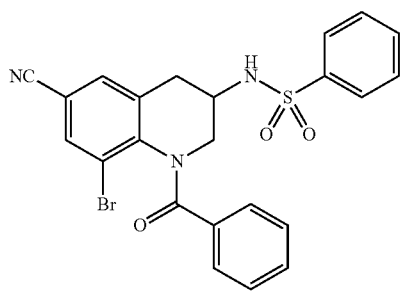

164A. N-(8-Bromo-6-cyano-1,2,3,4-tetrahydroquinolin-3-yl)-benzene-sulfonamide

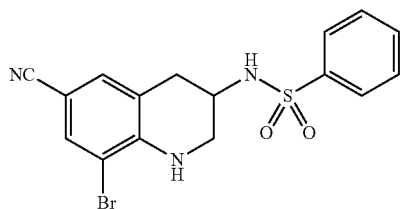

To a suspension of racemate 1G (323 mg, 1.03 mmol) in mixed solvents of MeOH (3 mL), CH₂Cl₂ (3 mL) and THF (3 mL) at RT was added CaCO₃ (103 mg, 1.03 mmol), followed by benzyltriethylammonium tribromide (445 mg, 1.03 mmol). After addition, the mixture was stirred at RT for 45 min. The resultant precipitate was collected by filtration, washed with 0.2 N aqueous HCl, H₂O, then dried to provide the title compound (311 mg, 77%) as a white solid.

164B. N-(1-Benzoyl-8-bromo-6-cyano-1,2,3,4-tetrahydroquinolin-3-yl)-benzenesulfonamide The title compound was prepared from 164A by procedures analogous to those described in Example 163B. HPLC: 99% at 6.3 min (retention time) (Conditions: Zorbax SB C18 (4.6×75 mm); Eluted with 0% to 100% B, 8 min gradient. (A=90% H₂O–10% MeOH–0.1% H₃PO₄ and B=10% H₂O–90% MeOH–0.1% H₃PO₄); Flow rate at 2.5 mL/min. UV detection at 220 nm). MS (ES): m/z 496 [M+H]⁺.

Example 165

N-(1-Benzyl-8-chloro-6-cyano-1,2,3,4-tetrahydroquinolin-3-yl)-benzenesulfonamide

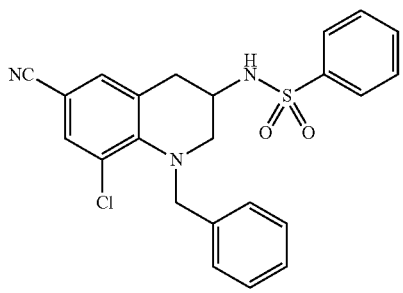

165A. N-(1-Benzyl-6-cyano-1,2,3,4-tetrahydroquinolin-3-yl)-benzene-sulfonamide

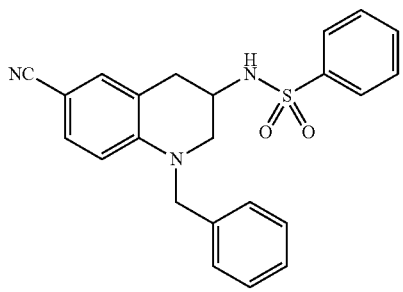

Compound 165A was prepared from racemate 1G and benzaldehyde by procedures analogous to those described in Example 22A.

165B. N-(1-Benzyl-8-chloro-6-cyano-1,2,3,4-tetrahydroquinolin-3-yl)-benzenesulfonamide To a solution of compound 165A (121 mg, 0.3 mmol) in acetic acid (2 mL) at RT was added benzyltrimethylammonium tetrachloroiodate (125.7 mg, 0.3 mmol). The reaction mixture was stirred at RT for 30 min, and then concentrated under reduced pressure. The resultant residue was partitioned between saturated aqueous NaHCO₃ solution and CH₂Cl₂. The separated aqueous layer was extracted with CH₂Cl₂ (15 mL×2). The combined CH₂Cl₂ extracts were washed with brine, dried (Na₂SO₄) and concentrated. The residue was purified using preparative HPLC (YMC S5 ODS 20×100 mm) eluting with MeOH (50-80%) in H₂O for 8 min, and then 80% MeOH in H₂O for 7 min to give the title compound (108 mg, 82%) as a white solid. HPLC: 99% at 7.65 min (retention time) (Conditions: Zorbax SB C18 (4.6×75 mm); Eluted with 0% to 100% B, 8 min gradient. (A=90% H₂O–10% MeOH–

0.1% $H_3PO_4$ and B=10% $H_2O$–90% MeOH–0.1% $H_3PO_4$); Flow rate at 2.5 mL/min. UV detection at 220 nm). MS (ES): m/z 438 [M+H]$^+$.

Example 166

N-(1-Benzyl-8-bromo-6-cyano-1,2,3,4-tetrahydroquinolin-3-yl)-benzenesulfonamide

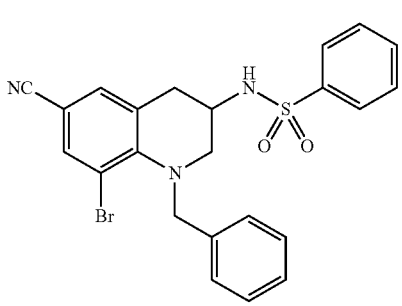

The title compound was prepared from 165A by procedures analogous to those described in Example 164A. HPLC: 99% at 7.73 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 483 [M+H]$^+$.

Example 167

N-(1-Benzenesulfonyl-6-bromo-1,2,3,4-tetrahydroquinolin-3-yl)-benzenesulfonamide

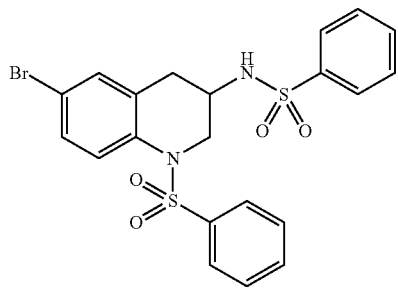

To a solution of compound 87A (98 mg, 0.299 mmol) in pyridine (3 mL) was added benzenesulfonyl chloride (0.042 mL, 0.33 mmol). The mixture was stirred at RT overnight, then concentrated. The residue was chromatographed (10 g silica gel) eluting with EtOAc (0-60%) in hexane to give the title compound (140 mg, 93%) as a white foam. HPLC: 99% at 7.06 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 529 [M+Na]$^+$.

Example 168

N-(1-Benzenesulfonyl-6-phenyl-1,2,3,4-tetrahydroquinolin-3-yl)-benzenesulfonamide

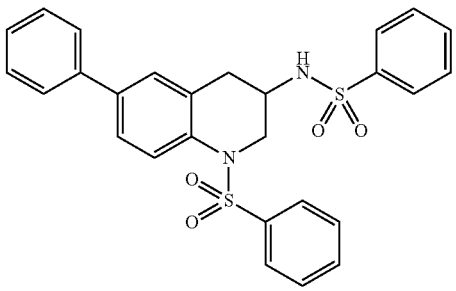

To a solution of compound 167 (51 mg, 0.1 mmol) in THF-MeOH (1:1) (2 mL) was added benzeneboronic acid (24 mg, 0.2 mmol), followed by $K_2CO_3$ (55 mg, 0.4 mmol) and PXPd (3.2 mg, 0.006 mmol). The mixture was heated at 62° C. overnight. After cooling to RT, the reaction was concentrated and MeOH (2 mL) added. The resulting suspension was filtered and the filtrate purified using preparative HPLC (Phenomenex Luna, 5μ, 30×100 mm column), eluting with 80-90% MeOH/$H_2O$ to give the title compound (42 mg, 85%) as a white foam. HPLC: 99% at 7.443 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 505 [M+1]$^+$.

Example 169

N-(1-Benzyl-6-phenoxy-1,2,3,4-tetrahydroquinolin-3-yl)benzenesulfonamide

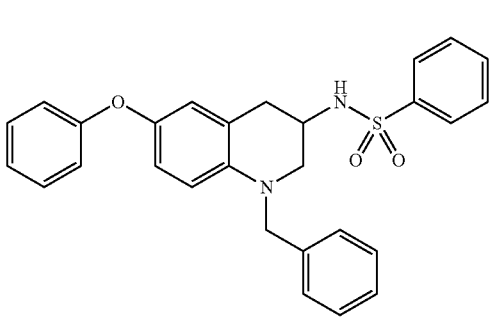

A suspension of 87B (55 mg, 0.12 mmol), phenol (33.9 mg, 0.36 mmol), $K_2CO_3$ (50 mg, 0.36 mmol) and copper iodide (17.1 mg, 0.09 mmol) in DMF (1.0 mL) was heated at 200° C. in a sealed tube with stirring for 16 h. After cooling to RT, the reaction mixture was filtered, the filtrate purified using preparative HPLC (YMC S5 ODS 20×100 mm) eluting with MeOH (70-100%) in $H_2O$ for 8 min, and then 100% MeOH in $H_2O$ for 7 min to give the title compound (4 mg) as a light brownish solid. HPLC: 91% at 6.99 min (retention time)

(Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 471 [M+H]$^+$.

Example 170

N-(8-Phenoxy-6-phenyl-1,2,3,4-tetrahydroquinolin-3-yl)benzenesulfonamide

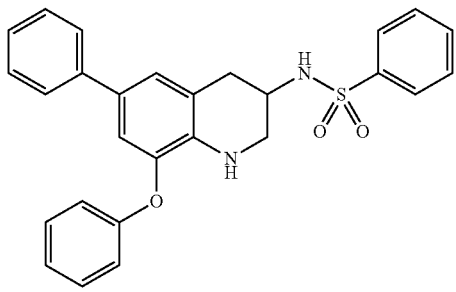

170A. N-(6-Phenyl-1,2,3,4-tetrahydroquinolin-3-yl)benzenesulfonamide

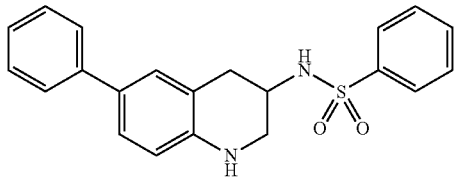

Compound 170A was prepared from 87A and phenylboronic acid by procedures analogous to those described in Example 91A.

170B. N-(8-Bromo-6-phenyl-1,2,3,4-tetrahydroquinolin-3-yl)benzenesulfonamide

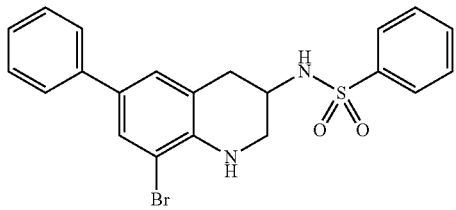

Compound 170B was prepared from 170A by procedures analogous to those described in Example 1B.

170C. N-(8-Phenoxy-6-phenyl-1,2,3,4-tetrahydroquinolin-3-yl)benzene sulfonamide

The title compound was prepared as an off-white powder from 170B by procedures described in Example 169. HPLC: 98% at 8.07 min (retention time) (Conditions: Zorbax SB C18 (4.6×75 mm); Eluted with 0% to 100% B, 8 min gradient. (A=90% $H_2O$–10% MeOH–0.1% $H_3PO_4$ and B=10% $H_2O$–90% MeOH–0.1% $H_3PO_4$); Flow rate at 2.5 mL/min. UV detection at 220 nm). MS (ES): m/z 457 [M+H]$^+$.

Example 171

N-(1-Benzyl-6-(4-fluorophenyl)-1,2,3,4-tetrahydroquinolin-3-yl)-2-oxo-2-phenylacetamide

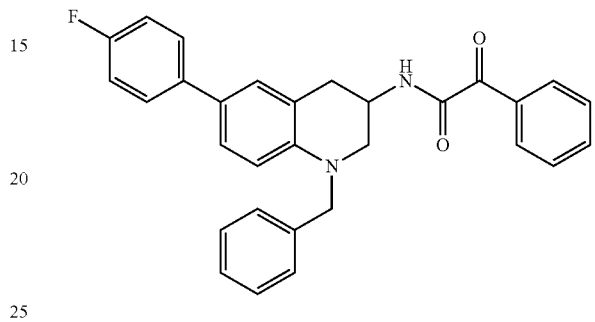

To a solution of 35 mg (0.06 mmol) of 89C in $CH_2Cl_2$ (0.6 mL) was added EDAC (13 mg, 0.07 mmol), HOBt (11 mg, 0.07 mmol), DIPEA (0.03 mL, 0.18 mmol) and benzoylformic acid (11 mg, 0.07 mmol). The reaction was stirred at RT overnight, and the solution was loaded directly onto silica gel column for purification. The product was purified via flash chromatography using EtOAc/hexanes to give 13 mg of a yellow oil. HPLC: 4.24 min, column: 4.6×50 mm Phenomenex LUNA C-18 (S-5); flow rate 2.5 mL/min; gradient: 0-100% B over 4 min, hold 100% B for 1 min. Solvent A: 10% MeOH-90% $H_2O$-0.2% $H_3PO_4$. Solvent B: 90% MeOH-10% $H_2O$-0.2% $H_3PO_4$. MS (ES): m/z 465 [M+1]$^+$.

Example 172

Ethyl 2-(1-benzyl-6-(4-fluorophenyl)-1,2,3,4-tetrahydroquinolin-3-ylamino)-2-oxoacetate

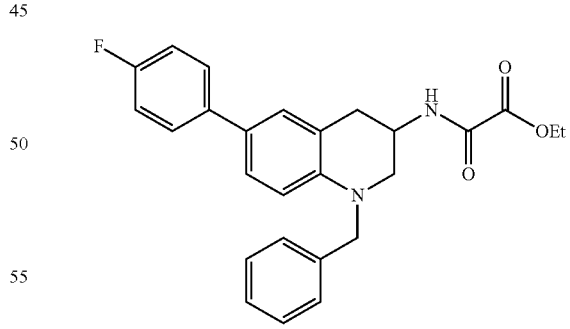

To a solution of 89C (60 mg, 0.11 mmol) in $CH_2Cl_2$ (1.5 mL) and added $Et_3N$ (0.06 mL, 0.44 mmol), followed by ethyl chlorooxoacetate (0.024 mL, 0.22 mmol). The reaction was stirred at RT for 1 h and the solution was loaded directly onto silica gel column for purification. The product was purified via flash chromatography using EtOAc/hexanes to give 40 mg of the title compound as a yellow solid. HPLC: 4.10 min, column: 4 6×50 mm Phenomenex LUNA C-18 (S-5); flow rate 2.5 mL/min; gradient: 0-100% B over 4 min, hold 100%

B for 1 min. Solvent A: 10% MeOH-90% $H_2O$-0.2% $H_3PO_4$. Solvent B: 90% MeOH-10% $H_2O$-0.2% $H_3PO_4$. MS (ES): m/z 433 [M+1]$^+$.

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μl. 5 ug of membranes were brought up to a final volume of 95 μl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25×PBS, 30 μl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 4000 nM. As determined by the assay described above, the CB-1 receptor binding $K_i$ values of the preferred working examples fall within the range of 0.01 nM to 4000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to preincubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities & Combinations

A. Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinson's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., *Am. J. Physiol. Endocrinol. Metab.*, 284: E966-E971 (2003)), AZ-242 (tesaglitazar; Astra-Zeneca; as described in B. Ljung, et. al., *J. Lipid Res.*, 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al, *J. Med. Chem.*, 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al, *J. Med. Chem.*, 20, 243-249 (1977), the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fabric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, Cl-1011 is effective in the prevention and regression of aortic fatty streak area in hamsters", Nicolosi et al, *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al, *Bioorg. Med. Chem. Lett*, 6 (1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al, *Curr. Med. Chem.*, 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA: cholesterol acyltransferase (ACAT). 7. Development of a series of substituted N-phenyl-N'-[(1-phenylcyclopentyl)-methyl]ureas with enhanced hypocholesterolemic activity", Stout et al, *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ideal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equal, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levodopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to S 39", *J. Immunol. Methods* (Netherlands), 188 (1), pp. 1-7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine,* 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula I of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of Formula I:

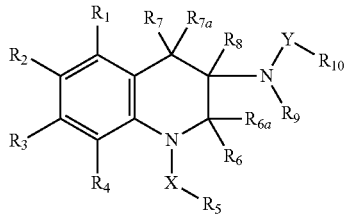

Formula I or a pharmaceutically acceptable salt or stereoisomer thereof, wherein:

$R_1$ is selected from the group consisting of hydrogen, alkyl, halo and CN;

$R_2$ is selected from the group consisting of hydrogen, alkyl, alkenyl, alkynyl, acyl, halo, $CF_3$, CN, nitro, phenyl, thienyl, pyridinyl, oxopyridinyl, oxopyrrolidinyl, oxopiperidinyl, imidazolyl, pyrazolyl and $OR_{11}$, $NR_{12}R_{12a}$, wherein phenyl, thienyl, pyridinyl, oxopyridinyl, oxopyrrolidinyl, oxopiperidinyl, imidazolyl and pyrazolyl may each be optionally substituted;

$R_3$ is selected from the group consisting of hydrogen, alkyl, halo and CN;

$R_4$ is selected from the group consisting of hydrogen, alkyl, halo and CN;

$R_5$ is selected from the group consisting of alkyl, cycloalkyl, phenyl, thienyl, pyrazinyl, pyridinyl, pyrazolyl, tetrahydrofuranyl, tetrahydropyranyl, thiazolyl and isothiazolyl, wherein alkyl, cycloalkyl, phenyl, thienyl, pyrazinyl, pyridinyl, pyrazolyl, tetrahydrofuranyl, tetrahydropyranyl, thiazolyl and isothiazolyl may each optionally be substituted;

$R_6$ and $R_{6a}$ are each independently selected from the group consisting of hydrogen and alkyl; $R_7$ and $R_{7a}$ are each independently selected from the group consisting of hydrogen and alkyl;

$R_8$ is hydrogen;

$R_9$ is selected from the group consisting of hydrogen and alkyl;

$R_{10}$ is selected from the group consisting of alkyl, alkenyl, alkoxy, cycloalkyl, thienyl, imidazolyl, pyrazolyl, thiazolyl, isothiazolyl, oxazolidinonyl, furanyl, isooxazolyl, piperidinyl, morpholinyl, phenyl, pyridinyl, benzothiadiazolyl and $NR_{12}R_{12a}$, wherein alkyl, alkenyl, alkoxy, cycloalkyl, thienyl, imidazolyl, pyrazolyl, thiazolyl, isothiazolyl, oxazolidinonyl, furanyl, isooxazolyl, piperidinyl, morpholinyl, phenyl, pyridinyl, benzothiadiazolyl may each optionally be substituted;

$R_{11}$ is phenyl;

$R_{12}$ and $R_{12a}$ are each independently selected from the group consisting of hydrogen, alkyl, and cycloalkyl and phenyl;

or $R_{12}$ and $R_{12a}$ taken together form morpholine, piperidine or pyrrolidine;

X is selected from the group consisting of $(CR_{14}R_{14a})_n$, CO and $S(O)_2$;

Y is selected from the group consisting of $S(O)_2$, $SO_2N(R_{15})$ and $C(O)C(O)$;

$R_{14}$ and $R_{14a}$ are each hydrogen;

$R_{15}$ is selected from the group consisting of hydrogen and alkyl;

or $R_{15}$ and $R_{10}$ taken together can form morpholine, piperidine or oxazolidinone;

n is an integer of 0, 1 or 2; and provided that when Y is $S(O)_2$ and $R_5$ is other than alkyl, $R_{10}$ is not optionally substituted phenyl.

2. The compound of claim 1 or a pharmaceutically acceptable salt or stereoisomer, wherein:

$R_1$ is hydrogen;

$R_2$ is selected from the group consisting of hydrogen, halo, CN and optionally substituted phenyl;

$R_3$ is hydrogen;

$R_4$ is hydrogen;

$R_5$ is selected from the group consisting of alkyl and optionally substituted phenyl;

$R_6$ and $R_{6a}$ are each hydrogen;

$R_7$ and $R_{7a}$ are each hydrogen;

$R_8$ is hydrogen;

$R_9$ is hydrogen; and

X is $CH_2$.

3. The compound of claim 2 or a pharmaceutically acceptable salt or stereoisomer, wherein:

Y is selected from the group consisting of $S(O)_2$ and $SO_2N(R_{15})$.

4. The compound of claim 3 or a pharmaceutically acceptable salt or stereoisomer, wherein:

Y is $S(O)_2$.

5. The compound of claim 1 or a pharmaceutically acceptable salt or stereoisomer thereof, wherein the compound is selected from the group consisting of:

Pyridine-3-sulfonic acid[1-(3-chlorobenzyl)-6-cyano-1,2,3,4-tetrahydroquinolin-3-yl)-amide;

Pyridine-2-sulfonic acid[1-(3-chlorobenzyl)-6-cyano-1,2,3,4-tetrahydroquinolin-3-yl)-amide;

Thiophene-2-sulfonic acid[1-(3-chlorobenzyl)-6-cyano-1,2,3,4-tetrahydroquinolin-3-yl)-amide;

N-(6-Chloro-1-isopentyl-1,2,3,4-tetrahydroquinolin-3-yl)benzenesulfonamide;

N-(6-Chloro-1-butyl-1,2,3,4-tetrahydroquinolin-3-yl)benzenesulfonamide;

N,N-Dimethylamino-1-sulfonic acid (1-benzyl-6-chloro-1,2,3,4-tetrahydroquinolin-3-yl)-amide;

N-(1-Benzyl-6-chloro-1,2,3,4-tetrahydroquinolin-3-yl)ethanesulfonamide;

N-(1-Benzyl-6-chloro-1,2,3,4-tetrahydroquinolin-3-yl)-2,2,2-trifluoroethanesulfonamide;

N-(1-Benzyl-6-chloro-1,2,3,4-tetrahydroquinolin-3-yl)-2-(naphthalen-1-yl)ethanesulfonamide;

N-(1-Benzyl-6-chloro-1,2,3,4-tetrahydroquinolin-3-yl)benzo(c)[1,2,5]thiazole-4-sulfonamide;

N-(1-Benzyl-6-chloro-1,2,3,4-tetrahydroquinolin-3-yl)-5-bromothiophene-2-sulfonamide;

N-(1-Benzyl-6-chloro-1,2,3,4-tetrahydroquinolin-3-yl)-4,5-dibromothiophene-2-sulfonamide;

N-(1-Benzyl-6-chloro-1,2,3,4-tetrahydroquinolin-3-yl)-4,5-dichlorothiophene-2-sulfonamide;

N-(1-Benzyl-6-chloro-1,2,3,4-tetrahydroquinolin-3-yl)-1-methyl-1H-imidazole-4-sulfonamide;

N-(1-Benzyl-6-chloro-1,2,3,4-tetrahydroquinolin-3-yl)-1,2-dimethyl-1H-imidazole-4-sulfonamide;

N-(1-Benzyl-6-chloro-1,2,3,4-tetrahydroquinolin-3-yl)-5-chloro-1,3-dimethyl-1H-pyrazole-4-sulfonamide;

N-(1-Benzyl-6-chloro-1,2,3,4-tetrahydroquinolin-3-yl)-3,5-dimethylisoxazole-4-sulfonamide;

N-(1-Benzyl-6-chloro-1,2,3,4-tetrahydroquinolin-3-yl)-thiophene-3-sulfonamide;
N-(1-Benzyl-6-chloro-1,2,3,4-tetrahydroquinolin-3-yl)-thiophene-2-sulfonamide;
N-(1-Benzyl-6-chloro-1,2,3,4-tetrahydroquinolin-3-yl)-5-(oxazol-5-yl)thiophene-2-sulfonamide;
N-(1-Benzyl-6-chloro-1,2,3,4-tetrahydroquinolin-3-yl)-5-(pyridin-2-yl)thiophene-2-sulfonamide;
N-(1-Benzyl-6-chloro-1,2,3,4-tetrahydroquinolin-3-yl)-5-bromo-6-chloro pyridine-3-sulfonamide;
N-(1-Benzyl-6-chloro-1,2,3,4-tetrahydroquinolin-3-yl)-6-morpholino chloro pyridine-3-sulfonamide;
N-(1-Benzyl-6-(4-fluorophenyl)-1,2,3,4-tetrahydroquinolin-3-yl)-2-acetamido-4-methyl thiazole-5-sulfonamide;
N-(1-Benzyl-6-(4-fluorophenyl)-1,2,3,4-tetrahydroquinolin-3-yl)-3,5-dimethylisoxazole-4-sulfonamide;
N-(1-Benzyl-6-(4-fluorophenyl)-1,2,3,4-tetrahydroquinolin-3-yl)-1-methyl-1H-imidazole-4-sulfonamide;
N-(1-Benzyl-6-(4-fluorophenyl)-1,2,3,4-tetrahydroquinolin-3-yl)-5-chloro-1,2-dimethyl-1H-imidazole-4-sulfonamide;
N-(1-Benzyl-6-(4-fluorophenyl)-1,2,3,4-tetrahydroquinolin-3-yl)-1,2-dimethyl-1H-imidazole-4-sulfonamide;
N-(1-Benzyl-6-(4-fluorophenyl)-1,2,3,4-tetrahydroquinolin-3-yl)-5-(oxazol-5-yl)-thiophene-2-sulfonamide;
N-(1-Benzyl-6-(4-fluoro phenyl)-1,2,3,4-tetrahydroquinolin-3-yl)-5-(isoxazole-3-yl)thiophene-2-sulfonamide;
N-(1-Benzyl-6-(4-fluorophenyl)-1,2,3,4-tetrahydroquinolin-3-yl)-5-chlorothiophene-2-sulfonamide;
N-(1-Benzyl-6-(4-fluorophenyl)-1,2,3,4-tetrahydroquinolin-3-yl)-5-methyl-2-(trifluoromethyl)furan-3-sulfonamide;
N-(1-Benzyl-6-(4-fluorophenyl)-1,2,3,4-tetrahydroquinolin-3-yl)pyridine-2-sulfonamide;
N-(1-Benzyl-6-(4-fluorophenyl)-1,2,3,4-tetrahydroquinolin-3-yl)pyridine-3-sulfonamide;
N-(1-Benzyl-6-(4-fluorophenyl)-1,2,3,4-tetrahydroquinolin-3-yl)-5-(trifluomethyl)pyridine-2-sulfonamide;
N-(1-Benzyl-6-(4-fluorophenyl)-1,2,3,4-tetrahydroquinolin-3-yl)(phenyl)methanesulfonamide;
N-(1-Benzyl-6-(4-fluorophenyl)-1,2,3,4-tetrahydroquinolin-3-yl)(pyridin-3-yl)methanesulfonamide;
N-(1-Benzyl-6-(4-fluorophenyl)-1,2,3,4-tetrahydroquinolin-3-yl)(pyridin-4-yl)methanesulfonamide;
N-(1-Benzyl-6-(4-fluorophenyl)-1,2,3,4-tetrahydroquinolin-3-yl)(pyridin-2-yl)methanesulfonamide;
N-(1-Benzyl-6-(4-fluorophenyl)-1,2,3,4-tetrahydroquinolin-3-yl)-2-phenylethene sulfonamide;
(S)-Piperidine-1-sulfonic acid (1-benzyl-6-cyano-1,2,3,4-tetrahydroquinolin-3-yl)-amide;
Morpholine-4-sulfonic acid [1-(3-chloro-benzyl)-6-cyano-1,2,3,4-tetrahydro-quinolin-3-yl]-amide;
N-(1-Benzyl-6-cyano-1,2,3,4-tetrahydroquinolin-3-yl)-2-oxooxazolidine-3-sulfonamide;
N-(1-Benzyl-6-cyano-1,2,3,4-tetrahydroquinolin-3-yl)-cyclohexylamino-3-sulfonamide;
N-(1-Benzyl-6-cyano-1,2,3,4-tetrahydroquinolin-3-yl)-anilinyl-5-sulfonamide;
N-(1-Benzyl-6-(4-fluorophenyl)-1,2,3,4-tetrahydroquinolin-3-yl)-2-oxo-2-phenylacetamide; and
Ethyl 2-(1-benzyl-6-(4-fluorophenyl)-1,2,3,4-tetrahydroquinolin-3-ylamino)-2-oxoacetate.

6. A pharmaceutical composition comprising a compound of claim 1 in an amount sufficient to treat obesity or to induce smoking cessation and a pharmaceutically acceptable carrier or diluent.

7. A pharmaceutical composition comprising a combination of a composition according to claim 6 and an additional anti-obesity agent selected from the group consisting of melanocortin receptor (MC4R) agonists; melanin-concentrating hormone receptor (MCHR) antagonists; growth hormone secretagogue receptor (GHSR) antagonists; galanin receptor modulators; orexin antagonists; CCK agonists; GLP-1 agonists and other Pre-proglucagon-derived peptides; NPY1 or NPY5 antagonists; NPY2 and NPY4 modulators; corticotropin releasing factor agonists; histamine receptor-3 (H3) modulators; aP2 inhibitors; PPAR gamma modulators; PPAR delta modulators; acetyl-CoA carboxylase (ACC) inhibitors; 11-β-HSD-1 inhibitors; adiponectin receptor modulators; beta 3 adrenergic agonists; thyroid receptor beta modulator; lipase inhibitors, serotonin receptor agonists, monoamine reuptake inhibitors or releasing agents, anorectic agents, topiramate; ciliary neurotrophic factor, brain-derived neurotrophic factor; leptin and leptin receptor modulators, SR-141716 and SLV-319 (ibipinabant); appetite suppressants; anti-diabetic agents; anti-hyperlipidemia agents; hypolipidemic agents selected from the group consisting of mevastatin; lovastatin; mevinolin; pravastatin; simvastatin fluvastatin; cerivastatin; atorvastatin; pitavastatin; nisvastatin; itavastatin; rosuvastatin; visastatin; SC-45355; dichloroacetate; imidazole analogs of mevalonolactone; 3-carboxy-2-hydroxy-propane-phosphonic acid derivatives; 2,3-disubstituted pyrrole, furan and thiophene derivatives; naphthyl analogs of mevalonolactone; octahydronaphthalenes; quinoline and pyridine derivatives; and phosphinic acid compounds; hypocholesterolemic agents; lipid-modulating agents selected from a phytoestrogen compound selected from isolated soy bean protein, soy protein concentrate, soy flour, isoflavone, genistein, daidzein, glycitein or equol, or phytosterols, phytostanol and tocotrienol; a beta-lactam cholesterol absorption inhibitor; an HDL upregulator selected from an LXR agonist, a PPAR α-agonist and an FXR agonist; an LDL catabolism promoter; a sodium-proton exchange inhibitor; an LDL-receptor inducer; steroidal glycoside; an anti-oxidant selected from beta-carotene, ascorbic acid, α-tocopherol, retinol, Vitamin C antihomocysteine agent, folic acid, a folate, Vitamin B6, Vitamin B12 and Vitamin E; isoniazid; a cholesterol absorption inhibitor; an HMG-CoA synthase inhibitor; a lanosterol demethylase inhibitor; a PPAR δ agonist for treating dyslipidemia; a sterol regulating element binding protein-I selected from a sphingolipid, ceramide, neutral sphingomyelenase or fragment thereof; cholesterol-lowering agents; lipid-lowering agents; HDL-raising agent, anti-hypertensive agents selected from beta adrenergic blockers; L-type channel blockers selected from diltiazem, verapamil, nifedipine, amlodipine and mybefradil; T-type calcium channel blockers selected from diltiazem, verapamil, nifedipine, amlodipine and mybefradil; diuretics selected from chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride and spironolactone; renin inhibitors; ACE inhibitors selected from captopril, zofenopril, fosinopril, enalapril, ceranopril, cilazopril, delapril, pentopril, quinapril, ramipril and lisinopril; AT-1 receptor antagonists selected from losartan, irbesartan and valsartan; ET receptor antagonists selected from sitaxsentan and atrsentan; Dual ET/AII antagonists; neutral endopeptidase inhibitors; vasopepsidase inhibitors and dual NEP-ACE inhibitors selected from omapatrilat and gemopatrilat; and nitrates.

8. A pharmaceutical combination according to claim 7 wherein the anti-diabetic agent is an oral antihyperglycemic agent selected from the group consisting of biguanides, metformin, phenformin, metformin HCl and pharmaceutically acceptable salts of the foregoing.

9. A method for treatment of obesity which comprises administering to a mammalian species in need of treatment a therapeutically effective amount of a compound as defined in claim 1.

* * * * *

UNITED STATES PATENT AND TRADEMARK OFFICE
CERTIFICATE OF CORRECTION

PATENT NO. : 8,119,808 B2  Page 1 of 1
APPLICATION NO. : 12/984628
DATED : February 21, 2012
INVENTOR(S) : Chongqing Sun et al.

It is certified that error appears in the above-identified patent and that said Letters Patent is hereby corrected as shown below:

On the Title Page:

Item (56), References Cited, under "OTHER PUBLICATIONS":

Column 2, line 1, change "Tamura, S.Y. et el.," to -- Tamura, S.Y. et al. --.

Column 2, line 2, change "es" to -- as --.

Column 2, Trillou reference, move "Tamura, S.Y. et al., "Novel Benzo-Fused Lactam Scaffolds as Factor Xa Inhibitors", Bioorganic & Medicinal Chemistry Letters, vol. 9 No. 17, pp. 2753-2758 (1999)." to next line as a separate paragraph.

In the Claims:

Column 113, line 41, change "$R_2$" to -- $R_7$ --.

Signed and Sealed this
Twenty-fourth Day of July, 2012

David J. Kappos
*Director of the United States Patent and Trademark Office*